(12) United States Patent
Faucher et al.

(10) Patent No.: US 9,012,506 B2
(45) Date of Patent: *Apr. 21, 2015

(54) CROSS-LINKED FATTY ACID-BASED BIOMATERIALS

(75) Inventors: Keith M. Faucher, Milford, NH (US); Hui Tang, Acton, MA (US); Joseph Ferraro, Londonderry, NH (US); Paul Martakos, Pelham, NH (US); Steve A. Herweck, Nashua, NH (US); Theodore Karwoski, Hollis, NH (US); Scott E. Corbeil, Litchfield, NH (US)

(73) Assignee: Atrium Medical Corporation, Merrimack, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/325,546

(22) Filed: Dec. 1, 2008

(65) Prior Publication Data
US 2009/0181937 A1    Jul. 16, 2009

Related U.S. Application Data

(63) Continuation-in-part of application No. 11/237,264, filed on Sep. 28, 2005, now Pat. No. 8,795,703, and a continuation-in-part of application No. 11/236,908, filed on Sep. 28, 2005, now Pat. No. 8,263,102, and a (Continued)

(51) Int. Cl.
*A61K 31/20* (2006.01)
*A61K 31/225* (2006.01)

(Continued)

(52) U.S. Cl.
CPC ............ *A61K 31/225* (2013.01); *A61K 31/355* (2013.01); *A61L 29/08* (2013.01); *A61L 29/16* (2013.01); *A61L 31/08* (2013.01); *A61L 31/16* (2013.01); *A61L 2300/22* (2013.01)

(58) Field of Classification Search
USPC ......................................................... 514/558
See application file for complete search history.

(56) References Cited

U.S. PATENT DOCUMENTS 2,368,306 A    1/1945    Kiefer et al.
2,986,540 A    5/1961    Posnansky (Continued)

FOREIGN PATENT DOCUMENTS

EP    0 471 566    2/1992
EP    0610731    8/1994

(Continued)

OTHER PUBLICATIONS

Jonasson, Lena et al., Cyclosporin A inhibits smooth muscle proliferation in the vascular response to Injury, Proc, Natl. Acad. Sci. vol. 85, pp. 2303-2306, 1988.*

(Continued)

*Primary Examiner* — Sean Basquill
*Assistant Examiner* — Andrew S Rosenthal
(74) *Attorney, Agent, or Firm* — Morse, Barnes-Brown & Pendleton, P.C.; Sean D. Detweiler, Esq.

(57) ABSTRACT

Fatty acid-derived biomaterials, methods of making the biomaterials, and methods of using them as drug delivery carriers are described. The fatty acid-derived biomaterials can be utilized alone or in combination with a medical device for the release and local delivery of one or more therapeutic agents. Methods of forming and tailoring the properties of said biomaterials and methods of using said biomaterials for treating injury in a mammal are also provided.

48 Claims, 24 Drawing Sheets

Related U.S. Application Data continuation-in-part of application No. 11/582,135, filed on Oct. 16, 2006, now Pat. No. 8,124,127.

(60) Provisional application No. 61/104,568, filed on Oct. 10, 2008, provisional application No. 60/613,808, filed on Sep. 28, 2004, provisional application No. 60/727,312, filed on Oct. 15, 2005, provisional application No. 60/613,745, filed on Sep. 28, 2004.

(51) Int. Cl.
*A61K 31/355* (2006.01)
*A61L 29/08* (2006.01)
*A61L 29/16* (2006.01)
*A61L 31/08* (2006.01)
*A61L 31/16* (2006.01)

(56) References Cited

U.S. PATENT DOCUMENTS

| | | | |
|---|---|---|---|
| 3,464,413 | A | 9/1969 | Goldfarb et al. |
| 3,556,294 | A | 1/1971 | Walck et al. |
| 3,567,820 | A | 3/1971 | Sperti |
| 3,803,109 | A | 4/1974 | Nemoto et al. |
| 3,967,728 | A | 7/1976 | Gordon et al. |
| 4,308,120 | A | 12/1981 | Pennewiss et al. |
| 4,323,547 | A | 4/1982 | Knust et al. |
| 4,557,925 | A | 12/1985 | Lindahl et al. |
| 4,664,114 | A | 5/1987 | Ghodsian |
| 4,813,210 | A | 3/1989 | Masuda et al. |
| 4,814,329 | A | 3/1989 | Harsanyi et al. |
| 4,847,301 | A | 7/1989 | Murray |
| 4,880,455 | A | 11/1989 | Blank |
| 4,883,667 | A | 11/1989 | Eckenhoff |
| 4,886,787 | A | 12/1989 | De Belder et al. |
| 4,894,231 | A | 1/1990 | Moreau et al. |
| 4,895,724 | A | 1/1990 | Cardinal et al. |
| 4,911,707 | A | 3/1990 | Heiber et al. |
| 4,938,763 | A | 7/1990 | Dunn et al. |
| 4,941,308 | A | 7/1990 | Grabenkort et al. |
| 4,952,419 | A | 8/1990 | De Leon |
| 4,968,302 | A | 11/1990 | Schluter et al. |
| 5,017,229 | A | 5/1991 | Burns et al. |
| 5,132,115 | A | 7/1992 | Wolter et al. |
| 5,147,374 | A | 9/1992 | Fernandez |
| 5,151,272 | A | 9/1992 | Engstrom et al. |
| 5,171,148 | A | 12/1992 | Wasserman et al. |
| 5,176,956 | A | 1/1993 | Jevne et al. |
| 5,179,174 | A | 1/1993 | Elton |
| 5,254,105 | A | 10/1993 | Haaga |
| 5,356,432 | A | 10/1994 | Rutkow et al. |
| 5,368,602 | A | 11/1994 | de la Torre |
| 5,371,109 | A | 12/1994 | Engstrom et al. |
| 5,380,328 | A | 1/1995 | Morgan |
| 5,387,658 | A | 2/1995 | Schroder et al. |
| 5,403,283 | A | 4/1995 | Luther |
| 5,447,940 | A | 9/1995 | Harvey et al. |
| 5,464,650 | A | 11/1995 | Berg et al. |
| 5,480,653 | A | 1/1996 | Aguadisch et al. |
| 5,509,899 | A | 4/1996 | Fan et al. |
| 5,579,149 | A | 11/1996 | Moret et al. |
| 5,580,923 | A | 12/1996 | Yeung et al. |
| 5,591,230 | A | 1/1997 | Horn et al. |
| 5,593,441 | A | 1/1997 | Lichtenstein et al. |
| 5,612,074 | A | 3/1997 | Leach |
| 5,614,284 | A | 3/1997 | Kranzler et al. |
| 5,627,077 | A | 5/1997 | Dyllick-Brenzinger et al. |
| 5,637,113 | A | 6/1997 | Tartaglia et al. |
| 5,665,115 | A | 9/1997 | Cragg |
| 5,695,525 | A | 12/1997 | Mulhauser et al. |
| 5,700,286 | A | 12/1997 | Tartaglia et al. |
| 5,736,152 | A | 4/1998 | Dunn |
| 5,753,259 | A | 5/1998 | Engstrom et al. |
| 5,760,081 | A | 6/1998 | Leaf et al. |
| 5,766,246 | A | 6/1998 | Mulhauser et al. |
| 5,766,710 | A | 6/1998 | Turnlund et al. |
| 5,789,465 | A | 8/1998 | Harvey et al. |
| 5,817,343 | A | 10/1998 | Burke |
| 5,824,082 | A | 10/1998 | Brown |
| 5,837,313 | A | 11/1998 | Ding et al. |
| 5,843,919 | A | 12/1998 | Burger |
| 5,874,470 | A | 2/1999 | Nehne et al. |
| 5,879,359 | A | 3/1999 | Dorigatti et al. |
| 5,898,040 | A | 4/1999 | Shalaby et al. |
| 5,906,831 | A | 5/1999 | Larsson et al. |
| 5,931,165 | A | 8/1999 | Reich et al. |
| 5,955,502 | A | 9/1999 | Hansen et al. |
| 5,986,043 | A | 11/1999 | Hubbell et al. |
| 6,005,004 | A | 12/1999 | Katz et al. |
| 6,010,766 | A | 1/2000 | Braun et al. |
| 6,010,776 | A | 1/2000 | Exsted et al. |
| 6,015,844 | A | 1/2000 | Harvey et al. |
| 6,028,164 | A | 2/2000 | Loomis |
| 6,040,330 | A | 3/2000 | Hausheer et al. |
| 6,056,970 | A | 5/2000 | Greenawalt et al. |
| 6,077,698 | A | 6/2000 | Swan et al. |
| 6,083,950 | A | 7/2000 | Anand et al. |
| 6,090,809 | A | 7/2000 | Anand et al. |
| 6,093,792 | A | 7/2000 | Gross et al. |
| 6,117,911 | A | 9/2000 | Grainger et al. |
| 6,120,789 | A | 9/2000 | Dunn |
| 6,132,765 | A | 10/2000 | DiCosmo et al. |
| 6,146,358 | A | 11/2000 | Rowe |
| 6,152,944 | A | 11/2000 | Holman et al. |
| 6,176,863 | B1 | 1/2001 | Kugel et al. |
| 6,193,746 | B1 | 2/2001 | Strecker |
| 6,197,357 | B1 | 3/2001 | Lawton et al. |
| 6,203,551 | B1 | 3/2001 | Wu |
| 6,206,916 | B1 | 3/2001 | Furst |
| 6,211,315 | B1 | 4/2001 | Larock et al. |
| 6,228,383 | B1 | 5/2001 | Hansen et al. |
| 6,229,032 | B1 | 5/2001 | Jacobs et al. |
| 6,245,811 | B1 | 6/2001 | Horrobin et al. |
| 6,254,634 | B1 | 7/2001 | Anderson et al. |
| 6,262,109 | B1 | 7/2001 | Clark et al. |
| 6,273,913 | B1 | 8/2001 | Wright et al. |
| 6,284,268 | B1 | 9/2001 | Mishra et al. |
| 6,299,604 | B1 | 10/2001 | Ragheb et al. |
| 6,326,360 | B1 | 12/2001 | Kanazawa et al. |
| 6,331,568 | B1 | 12/2001 | Horrobin |
| 6,342,254 | B1 | 1/2002 | Soudant et al. |
| 6,346,110 | B2 | 2/2002 | Wu |
| 6,358,556 | B1 | 3/2002 | Ding et al. |
| 6,364,893 | B1 | 4/2002 | Sahatjian et al. |
| 6,368,658 | B1 | 4/2002 | Schwarz et al. |
| 6,369,039 | B1 | 4/2002 | Palasis et al. |
| 6,387,379 | B1 | 5/2002 | Goldberg et al. |
| 6,410,587 | B1 | 6/2002 | Grainger et al. |
| 6,444,318 | B1 | 9/2002 | Guire et al. |
| 6,451,373 | B1 | 9/2002 | Hossainy et al. |
| 6,465,525 | B1 | 10/2002 | Guire et al. |
| 6,471,980 | B2 | 10/2002 | Sirhan et al. |
| 6,479,683 | B1 | 11/2002 | Abney et al. |
| 6,491,938 | B2 | 12/2002 | Kunz |
| 6,500,453 | B2 | 12/2002 | Brey et al. |
| 6,503,556 | B2 | 1/2003 | Harish et al. |
| 6,525,145 | B2 | 2/2003 | Gavaert et al. |
| 6,527,801 | B1 | 3/2003 | Dutta |
| 6,534,693 | B2 | 3/2003 | Fischell et al. |
| 6,548,081 | B2 | 4/2003 | Sadozai et al. |
| 6,565,659 | B1 | 5/2003 | Pacetti et al. |
| 6,569,441 | B2 | 5/2003 | Kunz et al. |
| 6,599,323 | B2 | 7/2003 | Melican et al. |
| 6,610,035 | B2 | 8/2003 | Yang et al. |
| 6,610,068 | B1 | 8/2003 | Yang |
| 6,630,151 | B1 | 10/2003 | Tarletsky et al. |
| 6,630,167 | B2 | 10/2003 | Zhang |
| 6,632,822 | B1 | 10/2003 | Rickards et al. |
| 6,641,611 | B2 | 11/2003 | Jayaraman |
| 6,645,547 | B1 | 11/2003 | Shekalim |
| 6,663,880 | B1 | 12/2003 | Roorda et al. |
| 6,669,735 | B1 | 12/2003 | Pelissier |
| 6,670,355 | B2 | 12/2003 | Azrolan et al. |
| 6,677,342 | B2 | 1/2004 | Wolff et al. |

(56) References Cited

U.S. PATENT DOCUMENTS

| | | |
|---|---|---|
| 6,677,386 B1 | 1/2004 | Giezen et al. |
| 6,685,956 B2 | 2/2004 | Chu et al. |
| 6,730,064 B2 | 5/2004 | Ragheb et al. |
| 6,753,071 B1 | 6/2004 | Pacetti |
| 6,761,903 B2 | 7/2004 | Chen et al. |
| 6,764,509 B2 | 7/2004 | Chinn et al. |
| 6,776,796 B2 | 8/2004 | Falotico et al. |
| 6,794,485 B2 | 9/2004 | Shalaby et al. |
| 6,833,004 B2 | 12/2004 | Ishii et al. |
| 6,852,330 B2 | 2/2005 | Bowman et al. |
| 6,875,230 B1 | 4/2005 | Morita et al. |
| 6,884,428 B2 | 4/2005 | Binette et al. |
| 6,887,270 B2 | 5/2005 | Miller et al. |
| 6,899,729 B1 | 5/2005 | Cox et al. |
| 6,918,927 B2 | 7/2005 | Bates et al. |
| 6,996,952 B2 | 2/2006 | Gupta et al. |
| 7,070,858 B2 | 7/2006 | Shalaby et al. |
| 7,101,381 B2 | 9/2006 | Ford et al. |
| 7,152,611 B2 | 12/2006 | Brown et al. |
| 7,323,189 B2 | 1/2008 | Pathak |
| 7,415,811 B2 | 8/2008 | Gottlieb |
| 8,124,127 B2 | 2/2012 | Faucher et al. |
| 8,263,102 B2 | 9/2012 | Labrecque et al. |
| 8,367,099 B2 | 2/2013 | Herweck et al. |
| 8,501,229 B2 | 8/2013 | Faucher et al. |
| 8,722,077 B2 | 5/2014 | Labrecque et al. |
| 2001/0025034 A1 | 9/2001 | Arbiser |
| 2001/0025196 A1 | 9/2001 | Chinn et al. |
| 2001/0051595 A1 | 12/2001 | Lyons et al. |
| 2002/0002154 A1 | 1/2002 | Guivarc'h et al. |
| 2002/0007209 A1 | 1/2002 | Scheerder et al. |
| 2002/0012741 A1 | 1/2002 | Heinz et al. |
| 2002/0026899 A1 | 3/2002 | McLaughlin et al. |
| 2002/0026900 A1 | 3/2002 | Huang et al. |
| 2002/0032414 A1 | 3/2002 | Ragheb et al. |
| 2002/0055701 A1 | 5/2002 | Fischell et al. |
| 2002/0098278 A1 | 7/2002 | Bates et al. |
| 2002/0116045 A1 | 8/2002 | Eidenschink |
| 2002/0120333 A1 | 8/2002 | Keogh et al. |
| 2002/0122877 A1 | 9/2002 | Harish et al. |
| 2002/0142089 A1 | 10/2002 | Koike et al. |
| 2002/0193829 A1 | 12/2002 | Kennedy et al. |
| 2003/0003125 A1 | 1/2003 | Nathan et al. |
| 2003/0004564 A1 | 1/2003 | Elkins et al. |
| 2003/0055403 A1 | 3/2003 | Nestenborg et al. |
| 2003/0065292 A1 | 4/2003 | Darouiche et al. |
| 2003/0065345 A1 | 4/2003 | Weadock |
| 2003/0069632 A1 | 4/2003 | De Scheerder et al. |
| 2003/0072784 A1 | 4/2003 | Williams |
| 2003/0077272 A1 | 4/2003 | Pathak |
| 2003/0077310 A1 | 4/2003 | Pathak et al. |
| 2003/0077452 A1 | 4/2003 | Guire et al. |
| 2003/0083740 A1 | 5/2003 | Pathak |
| 2003/0086958 A1 | 5/2003 | Arnold et al. |
| 2003/0094728 A1 | 5/2003 | Tayebi |
| 2003/0108588 A1 | 6/2003 | Chen et al. |
| 2003/0130206 A1 | 7/2003 | Koziak et al. |
| 2003/0152609 A1 | 8/2003 | Fischell et al. |
| 2003/0175408 A1 | 9/2003 | Timm et al. |
| 2003/0176915 A1 | 9/2003 | Wright et al. |
| 2003/0181975 A1* | 9/2003 | Ishii et al. .................. 623/1.42 |
| 2003/0191179 A1 | 10/2003 | Joshi-Hangal et al. |
| 2003/0204168 A1 | 10/2003 | Bosma et al. |
| 2003/0204618 A1 | 10/2003 | Foster et al. |
| 2003/0207019 A1 | 11/2003 | Shekalim et al. |
| 2003/0220297 A1 | 11/2003 | Berstein et al. |
| 2004/0006296 A1 | 1/2004 | Fischell et al. |
| 2004/0014810 A1 | 1/2004 | Horrobin |
| 2004/0018228 A1 | 1/2004 | Fischell et al. |
| 2004/0039441 A1 | 2/2004 | Rowland et al. |
| 2004/0071756 A1 | 4/2004 | Fischell et al. |
| 2004/0072849 A1 | 4/2004 | Schreiber et al. |
| 2004/0073284 A1 | 4/2004 | Bates et al. |
| 2004/0117007 A1 | 6/2004 | Whitbourne et al. |
| 2004/0133275 A1 | 7/2004 | Mansmann |
| 2004/0137066 A1 | 7/2004 | Jayaraman |
| 2004/0137179 A1 | 7/2004 | Matsuda et al. |
| 2004/0142094 A1 | 7/2004 | Narayanan |
| 2004/0146546 A1 | 7/2004 | Gravett et al. |
| 2004/0156879 A1 | 8/2004 | Muratoglu et al. |
| 2004/0161464 A1 | 8/2004 | Domb |
| 2004/0167572 A1 | 8/2004 | Roth et al. |
| 2004/0170685 A1 | 9/2004 | Carpenter et al. |
| 2004/0192643 A1 | 9/2004 | Pressato et al. |
| 2004/0215219 A1 | 10/2004 | Eldridge et al. |
| 2004/0224003 A1 | 11/2004 | Schultz |
| 2004/0230176 A1 | 11/2004 | Shanahan et al. |
| 2004/0234574 A9 | 11/2004 | Sawhney et al. |
| 2004/0241211 A9 | 12/2004 | Fischell |
| 2004/0256264 A1 | 12/2004 | Israelsson et al. |
| 2005/0010078 A1 | 1/2005 | Jamiolkowski et al. |
| 2005/0084514 A1 | 4/2005 | Shebuski et al. |
| 2005/0095267 A1 | 5/2005 | Campbell et al. |
| 2005/0106209 A1 | 5/2005 | Ameri et al. |
| 2005/0112170 A1 | 5/2005 | Hossainy et al. |
| 2005/0113849 A1 | 5/2005 | Popadiuk et al. |
| 2005/0129787 A1 | 6/2005 | Murad |
| 2005/0158361 A1 | 7/2005 | Dhondt et al. |
| 2005/0159809 A1 | 7/2005 | Hezi-Yamit et al. |
| 2005/0165476 A1* | 7/2005 | Furst et al. .................. 623/1.42 |
| 2005/0165477 A1 | 7/2005 | Anduiza et al. |
| 2005/0182485 A1 | 8/2005 | Falotico et al. |
| 2005/0187376 A1 | 8/2005 | Pacetti |
| 2005/0203635 A1 | 9/2005 | Hunter et al. |
| 2005/0203636 A1 | 9/2005 | McFetridge |
| 2005/0232971 A1 | 10/2005 | Hossainy et al. |
| 2005/0249775 A1 | 11/2005 | Falotico et al. |
| 2005/0283229 A1 | 12/2005 | Dugan et al. |
| 2006/0008501 A1 | 1/2006 | Dhont et al. |
| 2006/0036311 A1 | 2/2006 | Nakayama et al. |
| 2006/0058881 A1 | 3/2006 | Trieu |
| 2006/0067974 A1 | 3/2006 | Labrecque |
| 2006/0067975 A1 | 3/2006 | Labrecque et al. |
| 2006/0067976 A1 | 3/2006 | Ferraro et al. |
| 2006/0067977 A1 | 3/2006 | Labrecque et al. |
| 2006/0067983 A1 | 3/2006 | Swanick et al. |
| 2006/0068674 A1 | 3/2006 | Dixit et al. |
| 2006/0078586 A1 | 4/2006 | Ferraro |
| 2006/0083768 A1 | 4/2006 | Labrecque et al. |
| 2006/0088596 A1 | 4/2006 | Labrecque |
| 2006/0093643 A1 | 5/2006 | Stenzel |
| 2006/0110457 A1 | 5/2006 | Labrecque |
| 2006/0121081 A1 | 6/2006 | Labrecque et al. |
| 2006/0124056 A1 | 6/2006 | Behnisch et al. |
| 2006/0134209 A1 | 6/2006 | Labhasetwar et al. |
| 2006/0158361 A1 | 7/2006 | Chou |
| 2006/0204738 A1 | 9/2006 | Dubrow et al. |
| 2006/0210701 A1 | 9/2006 | Chappa et al. |
| 2006/0240069 A1 | 10/2006 | Utas et al. |
| 2006/0246105 A1 | 11/2006 | Molz et al. |
| 2007/0015893 A1 | 1/2007 | Hakuta et al. |
| 2007/0071798 A1 | 3/2007 | Herweck |
| 2007/0084144 A1 | 4/2007 | Labrecque |
| 2007/0093894 A1 | 4/2007 | Darouiche |
| 2007/0141112 A1 | 6/2007 | Falotico et al. |
| 2007/0202149 A1 | 8/2007 | Faucher et al. |
| 2007/0212411 A1 | 9/2007 | Fawzy et al. |
| 2007/0264460 A1 | 11/2007 | Del Tredici |
| 2007/0275074 A1 | 11/2007 | Holm et al. |
| 2007/0280986 A1 | 12/2007 | Gil et al. |
| 2007/0286891 A1 | 12/2007 | Kettlewell et al. |
| 2007/0299538 A1 | 12/2007 | Roeber |
| 2008/0038307 A1 | 2/2008 | Hoffmann |
| 2008/0044481 A1 | 2/2008 | Harel |
| 2008/0045557 A1 | 2/2008 | Grainger et al. |
| 2008/0086216 A1 | 4/2008 | Wilson et al. |
| 2008/0109017 A1 | 5/2008 | Herweck |
| 2008/0113001 A1 | 5/2008 | Herweck |
| 2008/0118550 A1 | 5/2008 | Martakos et al. |
| 2008/0206305 A1 | 8/2008 | Herweck |
| 2008/0279929 A1 | 11/2008 | Devane et al. |
| 2008/0286440 A1 | 11/2008 | Scheer |
| 2009/0011116 A1 | 1/2009 | Herweck |
| 2009/0047414 A1 | 2/2009 | Corbeil |

(56) References Cited

U.S. PATENT DOCUMENTS

| | | | |
|---|---|---|---|
| 2009/0208552 | A1 | 8/2009 | Faucher et al. |
| 2010/0183697 | A1 | 7/2010 | Swanick et al. |
| 2010/0209473 | A1 | 8/2010 | Dhont et al. |
| 2010/0233232 | A1 | 9/2010 | Swanick |
| 2012/0016038 | A1 | 1/2012 | Faucher et al. |
| 2012/0213839 | A1 | 8/2012 | Faucher et al. |

FOREIGN PATENT DOCUMENTS

| | | |
|---|---|---|
| EP | 0623354 | 11/1994 |
| EP | 0730864 | 9/1996 |
| EP | 0790822 | 8/1997 |
| EP | 0873133 | 10/1998 |
| EP | 0917561 | 5/1999 |
| EP | 1140243 | 10/2001 |
| EP | 1181943 | 2/2002 |
| EP | 1270024 | 1/2003 |
| EP | 1273314 | 1/2003 |
| EP | 1364628 | 11/2003 |
| EP | 1520795 | 4/2005 |
| EP | 1557183 | 7/2005 |
| EP | 2083875 | 8/2009 |
| EP | 1 402 906 | 6/2011 |
| KR | 20080025986 | 3/2008 |
| WO | WO 86/00912 | 7/1984 |
| WO | WO 90/01969 | 3/1990 |
| WO | WO 95/26715 | 10/1995 |
| WO | WO 97/02042 | 1/1997 |
| WO | WO 97/09367 | 3/1997 |
| WO | WO 97/13528 | 4/1997 |
| WO | WO 98/30206 | 7/1998 |
| WO | WO 98/54275 | 12/1998 |
| WO | WO 99/25336 | 5/1999 |
| WO | WO 00/40278 | 7/2000 |
| WO | WO 00/62830 | 10/2000 |
| WO | WO 01/24866 | 4/2001 |
| WO | WO 01/26585 | 4/2001 |
| WO | WO 01/37808 | 5/2001 |
| WO | WO 01/60586 | 8/2001 |
| WO | WO 01/66036 | 9/2001 |
| WO | WO 01/76649 | 10/2001 |
| WO | WO 02/49535 | 6/2002 |
| WO | WO 02/100455 | 12/2002 |
| WO | WO 03/000308 | 1/2003 |
| WO | WO 03/015748 | 2/2003 |
| WO | WO 03/028622 | 4/2003 |
| WO | WO 03/037397 | 5/2003 |
| WO | WO 03/037398 | 5/2003 |
| WO | WO 03/039612 | 5/2003 |
| WO | WO-03/039612 A1 | 5/2003 |
| WO | WO 03/041756 | 5/2003 |
| WO | WO 03039612 A1 * | 5/2003 |
| WO | WO 03/070125 | 8/2003 |
| WO | WO 03/092741 | 11/2003 |
| WO | WO 03/092779 | 11/2003 |
| WO | WO 2004/004598 | 1/2004 |
| WO | WO 2004/006976 | 1/2004 |
| WO | WO 2004/006978 | 1/2004 |
| WO | WO 2004/028583 | 4/2004 |
| WO | WO 2004/091684 | 10/2004 |
| WO | WO 2005/000165 | 1/2005 |
| WO | WO 2005/016400 | 2/2005 |
| WO | WO 2005/053767 | 6/2005 |
| WO | WO 2005/073091 | 8/2005 |
| WO | WO 2005/116118 | 12/2005 |
| WO | WO 2006/024488 | 3/2006 |
| WO | WO 2006/036967 | 4/2006 |
| WO | WO 2006/102374 | 9/2006 |
| WO | WO 2007/047028 | 4/2007 |
| WO | WO 2008/057328 | 5/2008 |
| WO | WO 2012/009707 | 1/2012 |

OTHER PUBLICATIONS

Uchida, M.; Kurosawa, M.; Osada, Y. "Swelling Process and Order-Disorder Transition of Hydrogel Containing Hydrophobic Ionizable Groups" Macromolecules 1995,28, 4583-4586.*

Guler, O. Kemal et al., Some Emperical equations for oxypolymerization of linseed oil, Progress in Organic Coatings, 51 (2004), pp. 365-371.*

Edible Oils. (http://www.chempro.in/fattyacid.htm) accessed Apr. 14, 2014.*

Güler, Ö. Kemal et al., "Some empirical equations for oxypolymerization of linseed oil," *Progress in Organic Coatings*, vol. 51:365-371 (2004).

Jonasson, Lena et al., "Cyclosporon A inhibits smooth muscle proliferation in the vascular response to injury," *Proc. Natl. Acad. Sci. USA*, vol. 85:2303-2306 (1988).

Ogunniyi, D.S., "Castor oil: A vital industrial raw material," *Bioresource Technology*, vol. 97:1086-1091 (2006).

Redman, L.V. et al., "The Drying Rates of Raw Paint Oil—A Comparison," *The Journal of Industrial and Engineering Chemistry*, vol. 5(8):630-636 (1913).

International Preliminary Report on Patentability for Application No. PCT/US08/85386, dated Feb. 4, 2009.

International Search Report for Application No. PCT/US09/37364, dated Aug. 27, 2009.

Li, Shengqiao, A paper entitled, "Evaluation of the Biocompatibility and Drug Delivery Capabilities of Biological Oil Based Stent Coatings," by Li, Shengqiao of the Katholieke Universiteit Leuven.

Ackman, R.G., "Fish Oils", *Bailey's Industrial Oil and Fat Products*, 6th Edition, 279-317 (2005).

Andes, et al. "Antiproliferative Strategies for the Treatment of Vascular Proliferative Disease", *Current Vascular Pharmacology*, 1)1): 85-98 (2003).

Jorge, N., "Grasas y Aceites", 48(1): 17-24, (1997).

Lipids, Chapter 19, pp. 1-12 (2002).

Polymerization Merriam-Webster Online Dictionary, retrieved from <www.merriam-webster.com> on Dec. 13, 2009; Merriam-Webster's Inc. 2009; pp. 1.

Winter, et al., "Physical and Chemical Gelation" *Encyclopedia of Materials—Science and Technology*, vols. 1-11: 6691-6999 (2001).

International Search Report for PCT/US2011/44292, dated Dec. 6, 2011.

Supplementary European Search Report for Application No. EP 12004057, dated Apr. 10, 2013.

International Search Report for International Application PCT/US2013/044653, dated Sep. 4, 2013.

Notice of Allowance for U.S. Appl. No. 11/525,390 (listed on SB/08 as US-2007/0071798), mailed Oct. 4, 2012.

Advisory Action for U.S. Appl. No. 12/581,582 (listed on SB-08 as U.S. Publication No. 2010-0183697), dated Nov. 14, 2012.

Notice of Allowance for U.S. Appl. No. 11/525,390 (listed on SB-08 as U.S. Publication No. US-2007-0071798), dated Nov. 20, 2012.

Notice of Allowance for U.S. Appl. No. 11/525,390 (listed on SB/08 as US-2007/0071798), mailed Nov. 30, 2012.

Non-Final Office Action for U.S. Appl. No. 13/404,487 (listed on SB-08 as US 2012-0213839), dated Dec. 20, 2012.

Non-Final Office Action for U.S. Appl. No. 13/184,512 (listed on SB-08 as 2012-0016038), dated Jan. 31, 2013.

Non-Final Office Action for U.S. Appl. No. 11/978,840 (listed on SB-08 as U.S. No. US-2008-0118550), dated Feb. 19, 2013.

Non-Final Office Action for U.S. Appl. No. 13/682,991 (listed on SB-08 as U.S. Publication No. US-2013-0074452), dated Mar. 18, 2013.

Notice of Allowance for U.S. Appl. No. 13/404,487 (listed on SB-08 as U.S. Publication No. US-2012-0213839), dated Apr. 2, 2013.

Non-Final Office Action for U.S. Appl. No. 11/236,943 (listed on SB-08 as U.S. Publication No. US-2006-0067975), dated Apr. 22, 2013.

Final Office Action for U.S. Appl. No. 13/184,512 (listed on SB-08 as U.S. Publication No. U.S. 2012-0016038), date Jun. 25, 2013.

(56) References Cited

OTHER PUBLICATIONS

Non-Final Office Action for U.S. Appl. No. 11/237,264 (listed on SB-08 as U.S. Publication No. US-2006-0067983), dated Jul. 3, 2013.
Non-Final Office Action for U.S. Appl. No. 13/593,656 (listed on SB-08 as U.S. Publication No. US-2012-03115219), dated Jul. 15, 2013.
Notice of Allowance for U.S. Appl. No. 13/682,991 (listed on SB-08 as U.S. Publication No. US 2013-0074452), dated Aug. 1, 2013.
Notice of Allowance for U.S. Appl. No. 11/978,840 (listed on SB-08 as U.S. Publication No. US-2008-0118550), dated Aug. 6, 2013.
Mallegol, "Long-Term Behavior of Oil-Based Varnishes and Paints Photo-and Thermooxidation of Cured Linseed Oil", *Journal of the American Oil Chemists' Society*, 77:257-263 (2000).
Non-Final Office Action for U.S. Appl. No. 11/237,420 (listed on SB-08 as U.S. Publication No. US-2006-0078586), dated Nov. 12, 2013.
Non-Final Office Action for U.S. Appl. No. 12/075,223 (listed on SB-08 as U.S. Publication No. US-2008-0206305), dated Nov. 12, 2013.
Non-Final Office Action for U.S. Appl. No. 11/980,155 (listed on SB-08 as U.S. Publication No. US-2008-0113001), dated Nov. 12, 2013.
"Cure" in Academic Press Dictionary of Science and Technology (1992).
"Polymerization" Merriam-Webster Online Dictionary, retrieved from <www.merriam-webster.com> on Dec. 13, 2009; Merriam-Webster's Inc. 2009; pp. 1.
Ahuja et al. "Prevention of Postoperative Intraperitoneal Adhesions—An Experimental Study in Rats", Journal of Indian Pediatric Surgery 2002 7:15-20.
Autosuture, "ParietexTM Composite OS Series Mesh," retrieved online at http://www.autosuture.com/AutoSuture/pagebuilder.aspx?topicID=135734&breadcrumbs=135601:0 (2007).
Camurus, "In our endeavors to create the unique, we start with the best. Your product.".
De Scheerder, Ivan K. et al. "Biocompatibility of polymer-coated oversized metallic stents implanted in normal porcine coronary arteries," Atherosclerosis, vol. 114:105-114.
Drummond, Calum J. et al., "Surfactant self-assembly objects as novel drug delivery vehicles," Current Opinion in Colliod & Interface Science, vol. 4:449-456 (2000).
Engstrom, Sven, "Drug Delivery from Cubic and Other Lipid-water Phases," Lipid Technology, vol. 2(2):42-45 (1990).
Hwang, Chao-Wei et al, "Physiological Transport Forces Govern Drug Distribution for Stent-Based Delivery," Circulation, vol. 104:600-605 (2001).
Mallegol et al., "Drier Influence on the Curing of Linseed Oil," Progress in Organic Coatings 39:107-113 (2000).
Morse, Richard "Molecular Distillation of Polymerized Drying Oils," Industrial and Engineering Chemisry 33:1039-1043 (1941).
Oberhoff, Martin et al, "Local and Systemic Delivery of Low Molecular Weight Heparin Following PTCA: Acute Results and 6-Month Follow-Up of the Initial Clinical Experience With the Porous Balloon (PILOT-Study)," Catheterization and Cardiovascular Diagnosis, vol. 44:267-274 (1998).
Rutkow, Ira M. et al., "'Tension-free' inguinal herniorrhaphy: A preliminary report on the 'mesh plug' technique," Surgery, vol. 114:3-8 (1993).
Salu, Koen J. et al, "Addition of cytochalasin D to a biocompatible oil stent coating inhibits intimal hyperplasia in a porcine coronary model," Coronary Artery Disease, vol. 14(8):545-555 (2003).
Scheller, Bruno et al, "Addition of Paclitaxel to Contrast Media Prevents Restenosis After Coronary Stent Implantation," Journal of the American College of Cardiology, vol. 42(8):1415-1420 (2003).
Shahidi, Fereidoon ed.; "Bailey's Industrial Oil and Fats Products" 2005; John Wiley and Sons; vol. 5, Edible Oil and Fat Products: Processing Technologies, pp. 1-15.

Van der Giessen, Willem J. et al, "Marked Inflammatory Sequelae to Implantation of Biodegradable and Nonbiodegradable Polymers in Porcine Coronary Arteries," Circulation, vol. 94:1690-1697 (1996).
Websters Dictionary Online, Accessed on Feb. 13, 2009, entry for "polymer" p. 1 of 1.
Final Office Action for U.S. Appl. No. 11/236,943 (listed on SB-08 as U.S. Publication No. US-2006-0067975), dated Dec. 4, 2013.
Final Office Action for U.S. Appl. No. 11/237,264 (listed on SB-08 as U.S. Publication No. US-20060067983), dated Dec. 17, 2013.
Notice of Allowance for U.S. Appl. No. 13/593,656 (listed on SB-08 as U.S. Publication 2012-03115219), dated Jan. 24, 2014.
Binder et al., "Chromatographic Analysis of Seed Oils. Fatty Acid Composition of Castor Oil," The Journal of the American Oil Chemists' Society, vol. 39:513-517 (1962).
CECW-EE, "Ch. 4: Coating Types and Characteristics," Engineering and Design—Painting: New Construction and Maintenance, pp. 4-1 to 4-24 (1995).
Wikipedia, "Sirolimus," pp. 1-13, available online at http://en.wikipedia.org/wiki/Sirolimus, date accessed May 11, 2011.
PCT/US10/052899, Jan. 10, 2011, International Search Report.
U.S. Appl. No. 11/525,390, Feb. 21, 2011, Final, US 2007/0071798.
U.S. Appl. No. 11/980,155, Mar. 24, 2011, Non-final, US 2008/0109017.
U.S. Appl. No. 11/582,135, May 12, 2011, Final, US 2007/0202149.
U.S. Appl. No. 11/236,908, May 17, 2011, Non-final, US 2006/0067974.
Supplementary European Search Report for Application No. EP 08877338.7, dated Aug. 16, 2012.
Supplementary European Search Report for Application No. EP09819594.4, dated Aug. 14, 2012.
Non-final Office Action for U.S. Appl. No. 11/525,390, (listed on SB/08 as US 2007/0071798), mailed Jul. 11, 2011.
Notice of Allowance for U.S. Appl. No. 12/182,261 (listed on SB/08 as US US-2009-0047414), mailed Jul. 23, 2012.
Advisory Action for U.S. Appl. No. 12/401,243 (listed on SB/08 as US 2010-0233232), mailed Aug. 27, 2012.
Final Office Action for U.S. Appl. No. 12/581,582 (listed on SB-08 as US 2010/0183697), mailed Aug. 29, 2012.
International Search Report for International Application PCT/US05/034601, dated Apr. 10, 2006.
International Search Report for International Application PCT/US05/034610, dated Mar. 16, 2006.
International Search Report for International Application PCT/US05/034614, dated Aug. 29, 2006.
International Search Report for International Application PCT/US05/034615, dated May 16, 2006.
International Search Report for International Application PCT/US05/034678, dated Aug. 28, 2006.
International Search Report for International Application PCT/US05/034681, dated Jul. 26, 2006.
International Search Report for International Application PCT/US05/034682, dated Jul. 20, 2006.
International Search Report for International Application PCT/US05/034836, dated Jul. 6, 2006.
International Search Report for International Application PCT/US05/034941, dated May 4, 2006.
International Search Report for International Application PCT/US06/037184, dated Feb. 22, 2007.
International Preliminary Report on Patentability for International Application PCT/US06/040753, dated Oct. 3, 2008.
International Search Report for International Application PCT/US06/040753, dated Sep. 24, 2007.
International Search Report for International Application PCT/US07/019978, dated May 7, 2009.
International Search Report for International Application PCT/US07/022860, dated Apr. 22, 2009.
International Search Report for International Application PCT/US07/022944, dated Apr. 8, 2009.
International Search Report for International Application PCT/US08/000565, dated May 4, 2009.
International Preliminary Examination Report for International Application PCT/US08/071547, dated Aug. 26, 2010.

(56) References Cited

OTHER PUBLICATIONS

International Search Report for International Application PCT/US08/071547, dated Oct. 22, 2008.
International Preliminary Report on Patentability for International Application PCT/US08/071565, dated Aug. 27, 2009.
International Search Report for International Application PCT/US08/071565, dated Nov. 10, 2008.
International Search Report for International Application PCT/US08/085386, dated Feb. 4, 2009.
International Search Report for International Application PCT/US09/037364, dated Aug. 27, 2009.
International Search Report for International Application PCT/US10/026521, dated Jun. 23, 2010.
Non-final Office Action for U.S. Appl. No. 11/236,908 (listed on SB/08 as US 2006/0067974), mailed Mar. 25, 2006.
Non-final Office Action for U.S. Appl. No. 11/236,908 (listed on SB/08 as US 2006/0067974), mailed Aug. 24, 2009.
Final Office Action for U.S. Appl. No. 11/236,943 (listed on SB/08 as US 2006/0067975), mailed Dec. 23, 2009.
Non-Final Office Action for U.S. Appl. No. 11/236,943 (listed on SB/08 as US 2006/0067975), mailed Mar. 5, 2009.
Non-final Office Action for U.S. Appl. No. 11/236,977 (listed on SB/08 as US 2006/0088596), mailed Aug. 3, 2009.
Final Office Action for U.S. Appl. No. 11/237,263 (listed on SB/08 as US 2006/0110457), mailed Jul. 7, 2010.
Non-final Office Action for U.S. Appl. No. 11/237,263 (listed on SB/08 as US 2006/0110457), mailed Oct. 7, 2009.
Final Office Action for U.S. Appl. No. 11/237,264 (listed on SB/08 as US 2006/0067983), mailed Jun. 2, 2010.
Non-final Office Action for U.S. Appl. No. 11/237,264 (listed on SB/08 as US 2006/0067983), mailed Oct. 5, 2009.
Final Office Action for U.S. Appl. No. 11/701,799 (listed on SB/08 as US 2008/0109017), mailed Nov. 23, 2010.
Non-final Office Action for U.S. Appl. No. 11/237,420 (listed on SB/08 as US 2006/0078586), mailed Mar. 5, 2009.
Final Office Action for U.S. Appl. No. 11/237,420 (listed on SB/08 as US 2006/0078586), mailed Nov. 4, 2009.
Non-final Office Action for U.S. Appl. No. 11/237,420 (listed on SB/08 as US 2006/0078586), mailed Dec. 6, 2010.
Non-final Office Action for U.S. Appl. No. 11/238,532 (listed on SB/08 as US 2006/0067976), mailed Mar. 30, 2009.
Final Office Action for U.S. Appl. No. 11/238,532 (listed on SB/08 as US 2006/0067976), mailed Sep. 9, 2009.
Final Office Action for U.S. Appl. No. 11/238,554 (listed on SB/08 as US 2006/0121081), mailed May 12, 2010.
Non-final Office Action for U.S. Appl. No. 11/238,554 (listed on SB/08 as US 2006/0121081), mailed Oct. 9, 2009.
Final Office Action for U.S. Appl. No. 11/238,554 (listed on SB/08 as US 2006/0121081), mailed May 1, 2009.
Non-final Office Action for U.S. Appl. No. 11/238,554 (listed on SB/08 as US 2006/0121081), mailed Jul. 25, 2008.
Non-final Office Action for U.S. Appl. No. 11/238,564 (listed on SB/08 as US 2006/0083768), mailed Apr. 16, 2008.
Final Office Action for U.S. Appl. No. 11/238,564 (listed on SB/08 as US 2006/0083768), mailed Aug. 6, 2009.
Non-final Office Action for U.S. Appl. No. 11/239,555 (listed on SB/08 as US 2006/0067977), mailed Mar. 30, 2009.
Non-final Office Action for U.S. Appl. No. 11/525,328 (listed on SB/08 as US 2007/0084144), mailed Apr. 30, 2007.
Non-final Office Action for U.S. Appl. No. 11/525,390 (listed on SB/08 as US 2007/0071798), mailed Jul. 14, 2010.
Non-final Office Action for U.S. Appl. No. 11/582,135 (listed on SB/08 as US 2007/0202149), mailed Nov. 9, 2010.
Non-final Office Action for U.S. Appl. No. 11/582,135 (listed on SB/08 as US 2007/0202149), mailed Jan. 6, 2010.
Non-final Office Action for U.S. Appl. No. 11/582,135 (listed on SB/08 as US 2007/0202149), mailed May 12, 2009.
Non-final Office Action for U.S. Appl. No. 11/701,799 (listed on SB/08 as US 2008/0109017), mailed Apr. 12, 2010.
Non-final Office Action for U.S. Appl. No. 11/978,840 (listed on SB/08 as US 2008/0118550), mailed Dec. 3, 2010.
Non-final Office Action for U.S. Appl. No. 12/075,223 (listed on SB/08 as US 2008/0206305), mailed Dec. 8, 2010.
Non-final Office Action for U.S. Appl. No. 12/364,763 (listed on SB/08 as US 2009/0208552), mailed Dec. 11, 2009.
Final Office Action for U.S. Appl. No. 12/364,763 (listed on SB/08 as US 2009/0208552), mailed Sep. 21, 2010.
Interview summary for U.S. Appl. No. 11/236,908 (listed on SB/08 as US 2006/0067974), mailed May 5, 2009.
Interview summary for U.S. Appl. No. 11/237,420 (listed on SB/08 as US 2006/0078586), mailed May 5, 2009.
Timar Balizsy et al., "Chemical Principals of Textile Conservation," Oxford: Elsevier Science Ltd., 117-119 (1998).
Crivello et al., "Epoxidized triglycerides as renewable monomers in photoinitiated cationic polymerization," Chem. Mater, 1992:692-699.
Encylopedia Britannica Online, "Surface Coating," available online at http://www.britannica.com/EBchecked/topic/575029/surface-coating>, date accessed Jun. 17, 2011.
Supplementary European Search Report for Application No. EP 05 80 2894, dated Jul. 27, 2011.
Supplementary European Search Report in Application No. 05 800 844, dated Aug. 19, 2011.
Supplementary European Search Report in Application No. EP 05 80 4291, dated Jul. 26, 2011.
Supplementary European Search Report in Application No. EP 05 85 8430, dated Aug. 18, 2011.
Final Office Action for U.S. Appl. No. 11/980,155 (listed on SB/08 as US-2008-0113001), mailed Oct. 21, 2011.
Final Office Action for U.S. Appl. No. 11/237,420 (listed on SB/08 as US 2006/0078586), mailed Jul. 13, 2011.
Final Office Action for U.S. Appl. No. 12/182,165 (listed on SB/08 as US 2009-0011116), mailed Apr. 6, 2012.
Final Office Action for U.S. Appl. No. 12/182,261 (listed on SB/08 as US-2009-0047414), mailed Apr. 30, 2012.
Final Office Action for U.S. Appl. No. 12/401,243 (listed on SB/08 as US-2010-0233232), mailed Jun. 11, 2012.
Final Office Action for U.S. Appl. No. 11/978,840 (listed on SB/08 as US 2008/0118550), mailed Jun. 22, 2011.
Final Office Action for U.S. Appl. No. 12/075,223 (listed on SB/08 as US 2008/0206305), mailed Aug. 11, 2011.
Final Office Action for U.S. Appl. No. 11/701,799 (listed on SB/08 as US 2008/0109017), mailed Feb. 13, 2012.
Non-Final Office Action for U.S Appl. No. 12/182,261 (listed on SB/08 as US 2009-0047414), mailed Dec. 21, 2011.
Non-Final Office Action for U.S. Appl. No. 11/236,908 (listed on SB/08 as US-2006-0067974), mailed Dec. 2, 2011.
Non-Final Office Action for U.S. Appl. No. 11/582,135 (listed on SB/08 as US-2007-0202149, mailed Oct. 14, 2011.
Non-Final Office Action for U.S. Appli. No. 12/182,165 (listed on SB/08 as US 2009-0011116), mailed Jan. 5, 2012.
Non-Final Office Action for U.S. Appl. No. 12/401,243 (listed on SB/08 as US 2010-0233232), mailed Jan. 5, 2012.
Non-Final Office Action for U.S. Appl. No. 11/701,799 (listed on SB/08 as US 2008/0109017), mailed Aug. 17, 2011.
Non-Final Office Action for U.S. Appl. No. 12/581,582 (listed on SB/08 as US 2010-0183697), mailed Mar. 14, 2012,.
Notice of Allowance for U.S. Appl. No. 11/236,908 (listed on SB/08 as US-2006-0067974), mailed May 11, 2012.
Notice of Allowance for U.S. Appl. No. 11/582,135 (listed on SB/08 as US 2007-0202149), mailed Jan. 9, 2012.
Non-Final Office Action for U.S. Appl. No. 13/843,068, dated Sep. 29, 2014.
Notice of Allowance for U.S. Appl. No. 11/236,943 (listed on SB-08 as U.S. Publication No. US-2006-0067975), dated Oct. 6, 2014.
Non-Final Office Action for U.S. Appl. No. 13/184,512, dated Oct. 10, 2014.
Non-Final Office Action for U.S. Appl. No. 12/075,223, dated Oct. 29, 2014.
Notice of Allowance for U.S. Appl. No. 11/237,264 (listed on SB-08 as U.S. Publication No. US-2006-0067983), dated Mar. 27, 2014.

(56) References Cited

OTHER PUBLICATIONS

Notice of Allowance for U.S. Appl. No. 11/237,263 (listed on SB-08 as U.S. Publication No. US-2006-0110457), dated Mar. 27, 2014.
Supplementary European Search Report for Application No. EP 10825447, dated Mar. 31, 2014.
Non Final Office Action for U.S. Appl. No. 12/364,763 (listed on SB-08 as U.S. Publication No. US-2009-0208552), dated Apr. 23, 2014.
Non Final Office Action for U.S. Appl. No. 12/401,243 (listed on SB/08 as US 2010-0233232), mailed May 8, 2014.
Uchida, et al., "Swelling Process and Order-Disorder Transition of Hydrogel Containing Hydrophobic Ionizable Groups", *Macromolecules*, 28, 4583-4586 (1995).
Gutfinger, et al., "Polyphenols in Olive Oils", *Journal of the American Oil Chemists Society*, 58(11): 966-968 (1981).
Portilla, et al., "Prevention of Peritoneal Adhesions by Intraperitoneal Administration of Vitamin E: An Experimental Study in Rats", *Diseases of the Colon and Rectum*, 47; 2157-2161 (2005).
Sano, et al., "A controlled Trial of Selegiline, Alpha-Tocopherol, or Both as Treatment for Alzheimer's Disease", *The New England Journal of Medicine*, 336; 1216-1222 (1997).
Non Final Office Action for U.S. Appl. No. 12/581,582 (listed on SB-08 as U.S. Publication 2010-0183697), dated May 29, 2014.
Non-Final Office Action for U.S. Appl. No. 13/943,489, dated Jul. 1, 2014.
Final Office Action for U.S. Appl. No. 11/980,155, dated Jul. 21, 2014.
Final Office Action for U.S. Appl. No. 11/237,420, dated Jul. 22, 2014.
Non-Final Office Action for U.S. Appl. No. 11/701,799, dated Jul. 22, 2014.
Final Office Action for U.S. Appl. No. 12/075,223, dated Jul. 22, 2014.
Final Office Action for U.S. Appl. No. 12/581,582, dated Jan. 8, 2015.
Final Office Action for U.S. Appl. No. 12/401,243, dated Jan. 16, 2015.
Non-Final Office Action for U.S. Appl. No. 11/237,420, dated Jan. 21, 2015.
Notice of Allowance for U.S. Appl. No. 13/943,489, mailed Jan. 29, 2015.
Non-Final Office Action for U.S. Appl. No. 11/980,155, dated Nov. 7, 2014.
Notice of Allowance for U.S. Appl. No. 12/364,763 (listed on SB-08 as U.S. Publication No. US-2009-0208552), dated Dec. 5, 2014.

\* cited by examiner

Carbon-Carbon (C-C) Cross-linking of Fatty Acid Chains

Summary of Oil-Derived Biomaterial Reaction Chemistry

Ester and Lactone Cross-Links
Formed Results in
Solidifying the Coating into a Gel.

Volatilization of Water, Hydrocarbons
and Aldehydes, Resulting in
An Increase in Coating Viscosity.

Isomerization and Oxidation of C=C Bonds.

*Fig. 4*

ESTERIFICATION

Carboxylic Acid    Alcohol         Ester

ALCOHOLYSIS

Ester              Alcohol         Ester2          Alcohol2

ACIDOLYSIS

Ester          Carboxylic Acid     Ester2          Carboxylic Acid2

INTERESTERIFICATION

Ester              Ester2          Ester3          Ester4

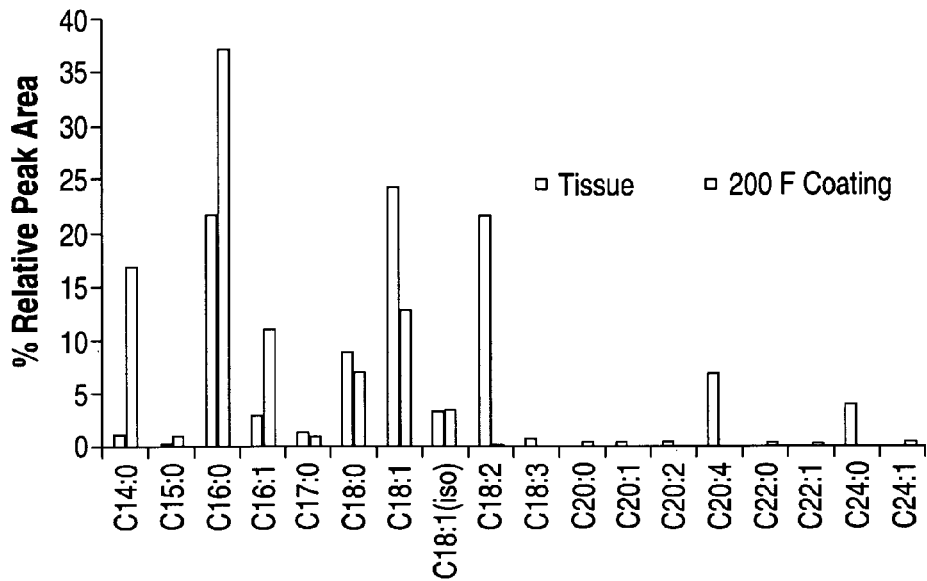
Fig. 7
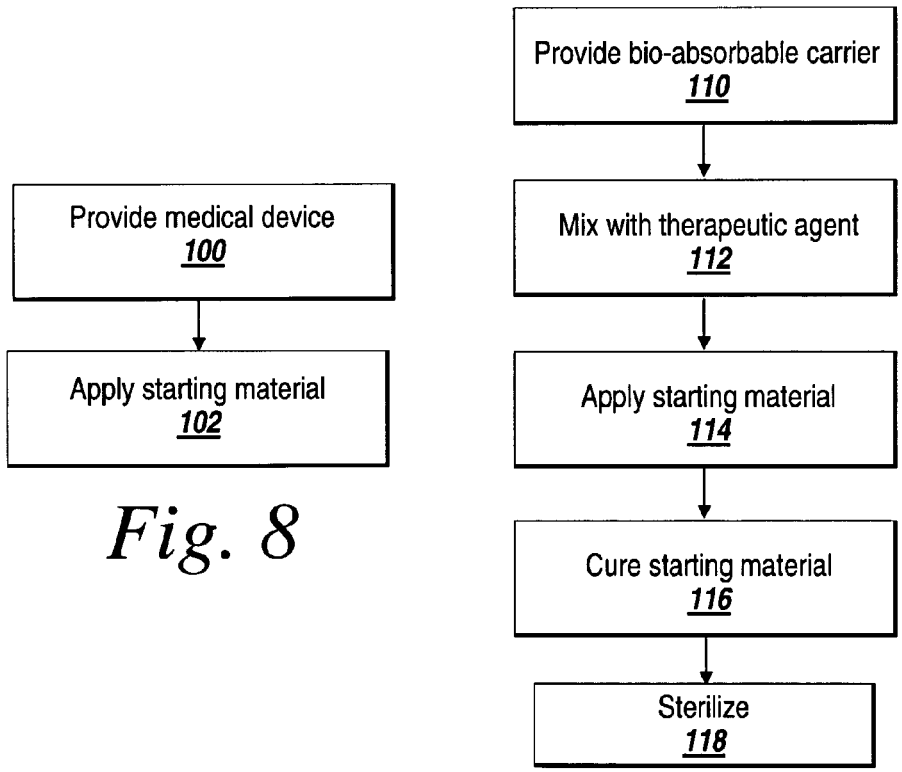
Fig. 8
Fig. 9

CROSS-LINKED FATTY ACID-BASED BIOMATERIALS

RELATED APPLICATIONS

This application claims priority to U.S. Provisional Application No. 61/104,568, filed Oct. 10, 2008. This application is also a continuation-in-part of U.S. patent application Ser. No. 11/582,135, filed Oct. 16, 2006, which claims priority to U.S. Provisional Patent Application Ser. No. 60/727,312, filed on Oct. 15, 2005. This application is also a continuation-in-part of U.S. patent application Ser. No. 11/237,264, filed Sep. 28, 2005, which claims priority to U.S. Provisional Application No. 60/613,808, filed Sep. 28, 2004. This application is also a continuation-in-part of U.S. patent application Ser. No. 11/236,908, filed Sep. 28, 2005, which claims priority to U.S. Provisional Application No. 60/613,745, filed Sep. 28, 2004. The entire contents of these previously filed applications are hereby incorporated herein by reference.

BACKGROUND OF THE INVENTION

Vascular interventions, such as vascular reperfusion procedures, balloon angioplasty, and mechanical stent deployment, can often result in vascular injury following mechanical dilation and luminal expansion of a narrowed vessel. Often, subsequent to such intravascular procedures, neointimal proliferation and vascular injury remodeling occurs along the luminal surface of the injured blood vessel; more specifically, remodeling occurs in the heart, as well as in vulnerable peripheral blood vessels like the carotid artery, iliac artery, femoral and popliteal arteries. No known mechanical suppression means have been found to prevent or effectively suppress such cellular proliferation from occurring immediately following vascular injury resulting from mechanical intervention and catheter directed reperfusion procedures. Left untreated, restenosis commonly occurs following a vascular intervention treated within the treated vessel lumen within weeks of a vascular injury. Restenosis, induced by localized mechanical injury causes proliferation of remodeled vascular lumen tissue, resulting in re-narrowing of the vessel lumen, which can lead to thrombotic closure from turbulent blood flow fibrin activation, platelet deposition and accelerated vascular flow surface injury. Restenosis pre-disposes the patient to a thrombotic occlusion and the stoppage of flow to other locations, resulting in critical ischemic events, often with morbidity.

Restenosis initiated by mechanical induced vascular injury cellular remodeling can be a gradual process. Multiple processes, including fibrin activation, thrombin polymerization and platelet deposition, luminal thrombosis, inflammation, calcineurin activation, growth factor and cytokine release, cell proliferation, cell migration and extracellular matrix synthesis each contribute to the restenotic process. While the exact sequence of bio-mechanical mechanisms of restenosis are not completely understood, several suspected biochemical pathways involved in cell inflammation, growth factor stimulation and fibrin and platelet deposition have been postulated. Cell derived growth factors such as platelet derived growth factor, fibroblast growth factor, epidermal growth factor, thrombin, etc., released from platelets, invading macrophages and/or leukocytes, or directly from the smooth muscle cells, provoke proliferative and migratory responses in medial smooth muscle cells. These cells undergo a change from the contractile phenotype to a synthetic phenotype. Proliferation/migration usually begins within one to two days post-injury and peaks several days thereafter. In the normal arterial wall, smooth muscle cells proliferate at a low rate, approximately less than 0.1 percent per day.

However, daughter cells migrate to the intimal layer of arterial smooth muscle and continue to proliferate and secrete significant amounts of extracellular matrix proteins. Proliferation, migration and extracellular matrix synthesis continue until the damaged endothelial layer is repaired, at which time proliferation slows within the intima, usually within seven to fourteen days post-injury. The newly formed tissue is called neointima. The further vascular narrowing that occurs over the next three to six months is due primarily to negative or constrictive remodeling.

Simultaneous with local proliferation and migration, inflammatory cells derived from the medial layer of the vessel wall continually invade and proliferate at the site of vascular injury as part of the healing process. Within three to seven days post-injury, substantial inflammatory cell formation and migration have begun to accumulate along the vessel wall to obscure and heal over the site of the vascular injury. In animal models, employing either balloon injury or stent implantation, inflammatory cells may persist at the site of vascular injury for at least thirty days. Inflammatory cells may contribute to both the acute and protracted chronic phases of restenosis and thrombosis.

Today, a preferred approach to the local delivery of a drug to the site of vascular injury caused by an intravascular medical device, such as a coronary stent, is to place a drug eluting coating on the device. Clinically, medical devices coated with a drug eluting coating comprised of either a permanent polymer or degradable polymer and an appropriate therapeutic agent have shown angiographic evidence that vascular wall proliferation following vascular injury and/or vascular reperfusion procedures can be reduced, if not eliminated, for a certain period of time subsequent to balloon angioplasty and/or mechanical stent deployment. Local delivery of a single sirolimus or taxol compound via a drug eluting medical device has been shown to be effective at minimizing or preventing cellular proliferation and cellular remodeling when applied immediately after vascular injury. Various analogs of these two anti-proliferative compound examples have also been shown experimentally and clinically to exhibit similar anti-proliferative activity with similar drug eluting coatings. However, anti-proliferative compounds such as sirolimus and taxol, together with a polymeric drug eluting coating have also been shown clinically to exhibit a number of toxic side effects, during and after principal drug release from the drug eluting coating. These chronic and or protracted side effects place limits on the amount of drug that can actually be delivered over a given period of time, as well as challenge the compatibility of the polymer coatings used to deliver a therapeutic agent locally to the site of the vascular injury when applied directly to a site of inflammation and or cellular remodeling. In addition, local overdosage of compounds like sirolimus and taxol can prevent, limit or even stop cellular remodeling or proliferation in and around the localized tissue area of the medical device. For example, a lack of endothelial cell coverage during the interruption of cell proliferation throughout the vascular injury healing process exhibits a high potential for luminal thrombosis whereby fibrin and a constant deposition of platelets blanket the exposed and non-healed medical device and/or damaged vascular injury. Without uninterrupted systemic support or administration of an anti-platelet medication like clopidegrel combined with an anti-clotting agent, such as ASA, prior to and following deployment of a drug eluting medical device, such devices have been shown clinically to thrombose and occlude within days of deployment. In addition, although these commercially available drug eluting polymer coatings employed on medical devices are generally characterized as being biocompatible, the lack of chemical hydrolysis, degradation and absorption of these polymer-based chemistries into smaller, easier to metabolize chemical components or products have been now been clinically demonstrated to initiate a protracted localized inflammatory response at the site of the vascular injury, which may lead to unexpected thrombotic occlusion within days of stopping anti-platelet medication.

Wound healing or response to in-vivo injury (e.g., hernia repair) follows the same general biological cascade as in vascular injury (see, e.g., Y. C. Cheong et al. *Human Reproduction Update.* 2001; Vol. 7, No. 6, pgs 556-566). This cascade includes inflammation of native tissue followed by migration and proliferation of cells to mitigate the inflammatory response, including platelets and macrophages, and a subsequent healing phase which includes fibrin deposition and the formation of fibrin matrix followed by tissue remodeling. In the case of hernia repair, abnormal peritoneal healing can occur when there is the expression of inflammatory cytokines from macrophages (e.g., α-TNF) that can result in an inability of the fibrin matrix to be properly broken down and can result in the formation of adhesions (Y. C. Cheong et al., 2001). Abdominal adhesions formed after hernia repair can result in pain, bowel strangulation, infertility and in some cases death (Y. C. Cheong et al., 2001).

The sustained nature of the thrombotic and inflammatory response to injury makes it desirable to provide a biomaterial that can reduce the incidence of inflammatory and foreign body responses after implantation. It would also be preferable to have a biomaterial that provides release of one or more therapeutic agents over a period of time in order to minimize such cell activated responses. Additionally, such a biomaterial would also preferably be metabolized via a bioabsorption mechanism.

SUMMARY OF THE INVENTION

What is desired is a biomaterial (e.g., a coating or stand-alone film) that can be utilized alone or as a drug delivery carrier that prevents or diminishes chronic inflammation due to either the therapeutic agent or hydrolysis products of the coating. Furthermore, it is desirable that the biomaterial release and deliver therapeutic agents in a sustained and controlled fashion to local tissue. The present invention is directed toward various solutions that facilitate addressing this need.

What is also desired is a biomaterial (e.g., a coating or stand-alone film) that can be bioabsorbed by cells and that can deliver a drug without inducing chronic localized inflammation to tissues (e.g., the peritoneal or vascular tissue) that has been injured mechanically or by reperfusion injury, whereby the biomaterial (e.g., coating or stand-alone film) and the therapeutic agent are ingested and metabolized by the cell, as it consumes the hydrolysis products of the biomaterial with the drug.

In various aspects, the biomaterial is a coating for a medical device, or a stand-alone film. The biomaterial can be a hydrophobic, fatty acid-derived, cross-linked biomaterial (referred to herein as a "fatty acid-derived biomaterial"). In various embodiments, the fatty acid-derived biomaterial is non-polymeric. In certain instances, as described herein, the source of the fatty acid is an oil, e.g., a fish oil. In such an instance, the fatty acid-derived biomaterial can also be referred to as an "oil-derived biomaterial."

In various aspects, the present invention may provide methods for producing a hydrophobic, cross-linked fatty acid-derived biomaterial (e.g., a medical device coating or stand-alone film) that can be utilized alone or in combination with one or more therapeutic agents, wherein the therapeutic agents have a controlled loading and are released in a sustained manner as the coating is absorbed. In various embodiments, provided are methods of tailoring the drug release profile of a hydrophobic, cross-linked fatty acid-derived biomaterial by control of the process or preparation (e.g., curing) conditions used to produce the fatty acid-derived biomaterial (e.g., coating or stand-alone film) from a polyunsaturated fatty acid starting material, e.g., an oil, e.g., a natural oil, containing starting material; the use of a free radical scavenger in an oil containing starting material from which the fatty acid-derived biomaterial is formed, or combinations thereof.

In various embodiments, the methods of the present invention tailor the drug release properties of a fatty acid-derived biomaterial (e.g., coating or stand-alone film) by controlling the degree of cross-linking. In various embodiments, the methods of the present invention tailor the drug delivery properties of a fatty acid-derived biomaterial (e.g., coating or stand-alone film) by controlling the level of fatty acids, tocopherols, lipid oxidation products, and soluble components in the cross-linked fatty acid-derived biomaterial.

In various aspects, the present invention may provide fatty acid-derived biomaterials (e.g., coating or stand-alone film) comprising one or more therapeutic agents with a tailored release profile for one or more of the therapeutic agents. In various embodiments, the tailored release profile comprises a sustained release profile. In various embodiments, the tailored release profile properties are controlled by the level of fatty acids, tocopherols, lipid oxidation products, and soluble components in the fatty acid-derived biomaterial. In various aspects of the present invention, the fatty acid-derived biomaterial contains fatty acids, many of which originate as triglycerides. It has previously been demonstrated that triglyceride byproducts, such as partially hydrolyzed triglycerides and fatty acid molecules can integrate into cellular membranes and enhance the solubility of drugs into cellular membranes (M. Cote, *J. of Controlled Release.* 2004, Vol. 97, pgs 269-281; C. P. Burns et al., *Cancer Research.* 1979, Vol. 39, pgs 1726-1732; R. Beck et al., *Circ. Res.* 1998, Vol 83, pgs 923-931; B. Henning et al. *Arterioscler. Thromb. Vasc. Biol.* 1984, Vol 4, pgs 489-797). Whole triglycerides are known not to enhance cellular uptake as well as a partially hydrolyzed triglyceride, because it is difficult for whole triglycerides to cross cell membranes due to their relatively larger molecular size. Vitamin E compounds can also integrate into cellular membranes resulting in decreased membrane fluidity and cellular uptake (P. P. Constantinides. *Pharmaceutical Research.* 2006; Vol. 23, No. 2, 243-255).

In various aspects, the present invention may provide a fatty acid-derived biomaterial (e.g., a medical device coating or stand-alone film) containing fatty acids, glycerides, lipid oxidation products and alpha-tocopherol in differing amounts and ratios to contribute to a cross-linked fatty acid-derived biomaterial in a manner that provides control over the cellular uptake characteristics of the cross-linked fatty acid-derived biomaterial and any therapeutic agents mixed therein.

In various aspects, the present invention may provide coated medical devices having a fatty acid-derived biomaterial drug release coating comprising one or more layers of said fatty acid-derived biomaterial, wherein at least one of the fatty acid-derived biomaterial layers contains one or more therapeutic agents. The coating can be a hydrophobic, fatty acid-derived, cross-linked biomaterial (derived, e.g., from fish oil). In various embodiments, the coating is non-polymeric. In various embodiments, the drug release coating hydrolyzes in vivo, into substantially non-inflammatory compounds. In various embodiments, the fatty acid-derived biomaterial is coated onto a medical device that is implantable in a patient to effect long term local delivery of the therapeutic agent to the patient. In various embodiments the delivery is at least partially characterized by the total and relative amounts of the therapeutic agent released over time. In various embodiments, the tailored delivery profile is controlled by the level of lipid oxidation and/or soluble components in the fatty acid-derived biomaterial. In various embodiments, the delivery profile is a function of the solubility and lipophilicity of the coating components and therapeutic agent in-vivo. The fatty acid-derived biomaterial can be a stand-alone film that has the properties discussed above.

In various embodiments, the present invention may provide coatings where the drug release profile of the coating is tailored through the provision of two or more coatings and selection of the location of the therapeutic agent. The drug location can be altered, e.g., by coating a bare portion of a medical device with a first starting material and creating a first cured coating, then coating at least a portion of the first cured-coating with the drug-oil formulation to create a second overlayer coating. It is to be understood that the process of providing two layers can be extended to provide three or more layers, wherein at least one of the layers comprises a fatty acid-derived biomaterial. In addition, one or more of the layers can be drug releasing, and the drug release profile of such layers can be tailored using the methods described herein.

In accordance with various embodiments of the present invention, the fatty acid-derived biomaterial (e.g., coating or stand-alone film) contains lipids. The fatty acid-derived biomaterial can be formed from an oil, such as fish oil, starting material. The fatty acid-derived biomaterial (e.g., coating or stand-alone film) can contain saturated, unsaturated, or polyunsaturated fatty acids. When the fatty acid-derived biomaterial is cross-linked, it can contain omega-3 fatty acids. The fatty acid-derived biomaterial can also contain alpha-tocopherol or vitamin E.

The coatings can be formulated to contain a variety of other chemicals and entities in addition to a therapeutic agent, including, but not limited to, one or more of: a pharmaceutically acceptable carrier, an excipient, a surfactant, a binding agent, an adjuvant agent, and/or a stabilizing agent (including preservatives, buffers and antioxidants). In one embodiment, alpha-tocopherol TPGS may be added to the coatings of the present invention.

In various aspects, the present invention may provide methods for treating injury in a mammal, such as, e.g., a human. In various embodiments, the injury is a vascular injury. In various embodiments, the methods comprise locally administering one or more therapeutic agents in a therapeutically effective amount by sustained release of the one or more therapeutic agents from a coating comprising a fatty acid-derived biomaterial.

The teachings herein demonstrate that the cured coatings and stand-alone films provided herein provide the ability to regulate the release profile of drug-loaded fatty acid-derived biomaterials from the films or from implantable devices. In various embodiments, the release profile can be controlled through changes in oil chemistry by varying fatty acid-derived biomaterial (e.g., coating for a medical device or stand-alone film) composition and cure times. The teachings demonstrate that the release of therapeutic compounds from fatty acid-derived biomaterials (e.g., coating or stand-alone film) can be modified based on altering the oil curing conditions, the oil starting material, length of curing, and amount of cross-linking. The teachings demonstrate that the cross-linking and gelation of the cured oil coatings and stand-alone film can be directly dependent on the formation of hydroperoxides in the oil component, which increases with increasing temperature and degree of unsaturation of the oil. Dissolution experiments have shown that drug release is more rapid for the cross-linked coatings produced using lower temperature curing conditions (e.g., around 150° F.) than higher temperature curing conditions (e.g., around 200° F.).

The teachings herein demonstrate that the use of vitamin E in cured oil (e.g., fish oil) coatings and stand-alone films is another method to alter the cross-linking and drug release properties of the coating. Vitamin E is an antioxidant that can slow down autoxidation in oil by reducing, it is believed, hydroperoxide formation during curing. This can result in a decrease in the amount of cross-linking observed in a cured oil coating or stand-alone film by inhibiting the formation of additional oxidative cross-linking species. Increasing the amount of vitamin E in the coating or stand-alone film can result in lengthening and slowing the release of a therapeutic agent from the coating. For example, the teachings herein demonstrate a lengthening and slowing of the release of Compound D from a hydrophobic, non-polymeric cross-linked fatty acid-derived biomaterial coating into a dissolution buffer, due, it is believed, to Compound D's affinity for the fatty acid and vitamin E components in the cured fish oil coating. The teachings herein further indicate that vitamin E can also results in protecting a drug such as Compound D and increase the amount of such drug extracted from the coating.

In one aspect, the present invention may provide a fatty acid-derived biomaterial (e.g., a medical device coating or stand-alone film) that is formed from a starting material comprising saturated, monounsaturated, and/or polyunsaturated fatty acids. In one aspect, the starting material is an oil, e.g., a fish oil.

In another aspect, the invention may provide a coating for a medical device comprising cross-linked fatty acids and glycerides. The source of the fatty acid can be an omega-3 fatty acid.

In another aspect, the invention may provide a coating for a medical device comprising: a cross-linked fatty acid oil, comprising approximately 5-50% $C_{16}$ fatty acids, e.g., 5-30% $C_{16}$ fatty acids. In one embodiment, the oil comprises 5-25% $C_{14}$ fatty acids. The oil can also comprise $C_{18}$ fatty acids (e.g., 0-60%), $C_{20}$ fatty acids (e.g., 0-40%), $C_{20}$ fatty acids (e.g., 0-40%), $C_{22}$ fatty acids (e.g., 0-30%), and/or $C_{24}$ fatty acids (e.g., less than 5%).

In another aspect, the invention may provide a coating for a medical device that hydrolyzes in vivo into fatty acids, glycerides and glycerol.

In still another aspect, the invention may provide a coating for a medical device comprising a non-polymeric, cross-linked fatty acid, comprising approximately 5-25% $C_{14}$ fatty acids and 5-50% $C_{16}$ fatty acids.

In yet another aspect, the invention may provide a coating for a medical device comprising cross-linked fatty acids and glycerides, wherein the fatty acids and glycerides have disordered alkyl groups, which cause the biomaterial to be flexible and hydratable.

In another aspect, the invention may provide a coating for a medical device comprising a fatty acid-derived biomaterial wherein the fatty acid-derived biomaterial comprises delta-lactones.

In still another aspect, the invention may provide a coating for a medical device comprising lactone and ester cross links, as indicated by an infrared absorption spectrum having peaks at approximately 1740-1830 $cm^{-1}$, respectively.

In yet another aspect, the invention may provide a coating for a medical device comprising a cross-linked, oil-derived biomaterial, wherein approximately 60-90% of the biomaterial is constituted by fatty acids with molecular weights below 500.

In another aspect, the invention may provide a coating for a medical device comprising an interesterified fatty acid. The fatty acid can be stearic acid, oleic acid, linoleic acid, alpha-linolenic acid, or gamma-linolenic acid. The source of the fatty acid can be an oil, e.g., fish oil, olive oil, grape oil, palm oil, or flaxseed oil.

In yet another aspect, the invention may provide a coating for a medical device comprising: a hydrophobic, non-polymeric cross-linked fatty acid; and a therapeutic agent; wherein the coating is sufficiently durable to withstand placement of the medical device in a patient.

In still another aspect, the invention may provide a coating for a medical device comprising an oil-derived biomaterial that has a contact angle of approximately 90-110 degrees when initially exposed to 0.1 M PBS solution, and, after approximately one hour of exposure, has a contact angle of 50-70 degrees.

In another aspect, the invention may provide a coating for a medical device that inhibits production of α-TNF.

In another aspect, the invention may provide a fatty acid-derived biomaterial (e.g., a coating or stand-alone film) suitable for achieving modulated healing in a tissue region in need thereof, wherein the biomaterial is administered in an amount sufficient to achieve said modulated healing, wherein the modulated healing comprises a modulation of platelet or fibrin deposition in or near said tissue region. The biomaterial can contain monounsaturated and/or saturated fatty acids in the coating. In one embodiment, the tissue region is the vasculature of a subject.

In another aspect, the invention may provide a fatty acid-derived biomaterial (e.g., a coating or stand-alone film) suitable for achieving modulated healing at a site of vascular injury in need thereof, wherein the composition is administered in an amount sufficient to achieve said modulated healing, wherein the modulated healing comprises a modulation of at least one metric of organized tissue repair. In one embodiment, the vascular healing is the inflammatory stage of vascular healing. In another embodiment, the organized tissue repair comprises platelet or fibrin deposition at the site of vascular injury. In another embodiment, the modulation of at least one metric of organized tissue repair is a delay in the healing process at a site of vascular injury.

The modulated healing biomaterials described herein can be administered to the tissue region in need thereof via a catheter, balloon, stent, surgical dressing or graft.

In one embodiment of the coating of the invention, the biomaterial comprises lactone and ester cross-links.

In another embodiment of the coating of the invention, the biomaterial contains disordered hydrocarbon chains as determined by infrared absorption and X-ray diffraction.

In still another embodiment of the coating of the invention, the biomaterial contains an amount of carboxylic acid groups sufficient to facilitate hydrolysis in vivo. The coating can break down in vivo into non-inflammatory components; or into fatty acids, glycerols, and glycerides.

In one embodiment of the coating of the invention, the biomaterial is configured to produce a glyceride upon metabolization in-vivo.

The coating of the invention may comprise approximately 30-90% saturated fatty acids. In one embodiment, the coating comprises approximately 30-80% unsaturated fatty acids. The coating can further comprise a glyceride. In another embodiment, said coating further comprises one or more of the group consisting of a glyceride, a glycerol, and a fatty alcohol, any of which can be partially cross-linked. In another embodiment, the coating does not contain a cross-linking agent.

In one embodiment of the coating of the invention, the source of the fatty acids and glycerides is an oil, e.g., fish oil, olive oil, grape oil, palm oil, or flaxseed oil. The oil can be alone or in combination with one or more oils. The coating can further comprise vitamin E. The coating can be associated with an implantable device, e.g., a medical device, e.g., a catheter, a surgical mesh or a balloon.

The coating can further comprise a therapeutic agent, including, but not limited to, an anti-proliferative drug, an anti-inflammatory agent, an antimicrobial agent or antibiotic agent. The therapeutic agent can be Compound A, Compound B, Compound C, Compound D, Compound E, or other cyclosporine derivatives or rapamycin derivatives.

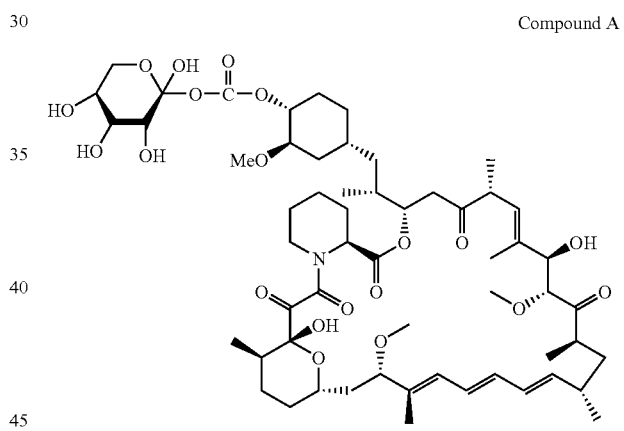

Compound A

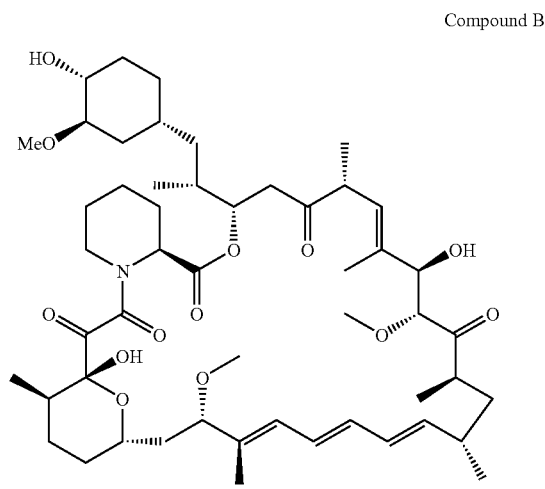

Compound B

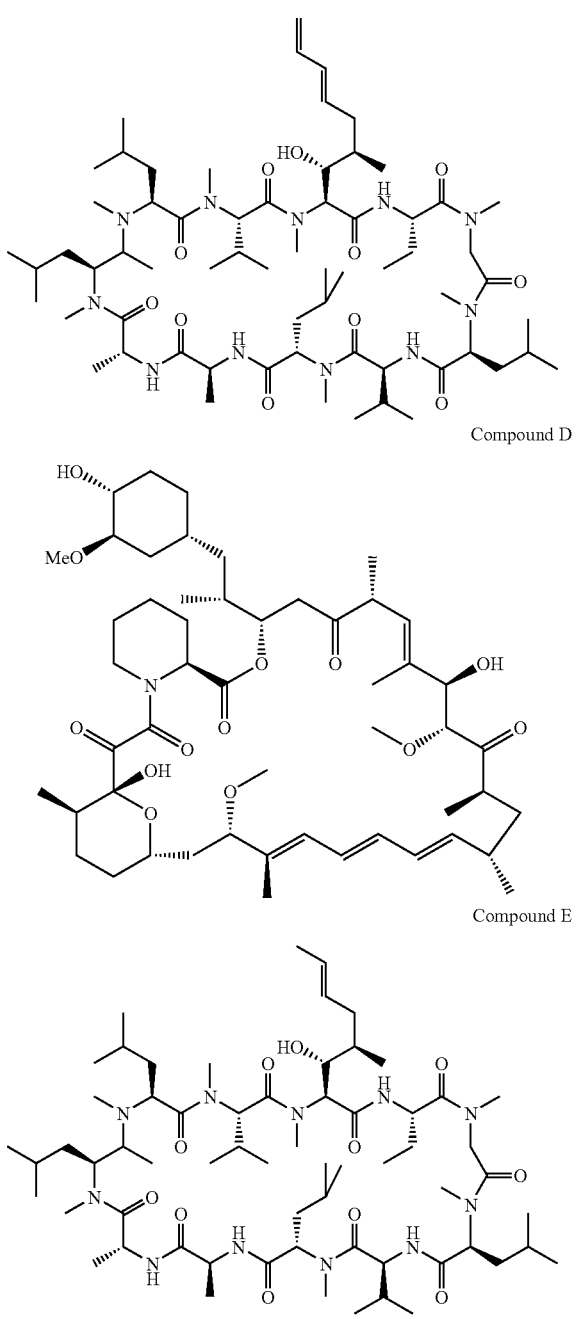

Compound C

Compound D

Compound E

The coating can have a release profile of the therapeutic agent in 0.01 M phosphate buffered saline (PBS) out to about 5-20 days, e.g., about 17-20 days, or more than 20 days. In another embodiment, the coating releases said therapeutic agent at a desired release rate in vivo.

In another aspect, the invention may provide a method of preparing a coating for a medical device, comprising heating a fatty acid-containing (e.g., polyunsaturated fatty acid-containing) oil in the presence of oxygen, such that: the double bonds of the oil are oxidized; fatty acids and glycerides are formed; and lactone and ester cross-links are formed between fatty acids and glycerides; such that the coating is formed. In one embodiment of this method, the oil is continually heated, without interruption.

In another aspect, the invention provides a method of preparing a coating for a medical device comprising heating a fatty acid-containing (e.g., polyunsaturated fatty acid-containing) oil in the presence of oxygen, such that: the double bonds of the oil are oxidized; water, hydrocarbons and aldehydes are volatilized; and ester and lactone cross-links are formed; such that the coating is formed. In one embodiment of this method, the oil is continually heated, without interruption.

In either of the aforementioned methods, the oil can be heated at approximately 140° F. to approximately 300° F., e.g., the oil is heated at 150° F. or 200° F. The oil used in the methods can be fish oil. The methods can also include the addition of a therapeutic agent. In a particular embodiment, the time and temperature of the curing step is adjusted to tailor drug release. The therapeutic agent can be an anti-proliferative drug, an anti-inflammatory agent, an antimicrobial agent or antibiotic agent, such as Compound A, Compound B, Compound C, Compound D, Compound E, a cyclosporine derivative or a rapamycin derivative. The coatings produced by these methods can be combined with an organic solvent, and sprayed on a medical device, such as a stent, a catheter, a surgical mesh or a balloon. The coatings produced by these methods can comprise lactone and ester cross links, as indicated by an infrared absorption spectrum having peaks at approximately 1740-1830 cm$^{-1}$, respectively. The coatings can also contain disordered hydrocarbon chains with an infrared absorption at approximately 3000-2800 cm$^{-1}$.

In another a aspect, the invention may provide a method of forming a fatty acid-derived biomaterial, comprising: continued heating of a fatty acid, thereby forming cross-links in the fatty acid; followed by the cleavage of C=C double bonds, which convert the fatty acids into oxidation byproducts. The oxidation byproducts can be aldehydes, ketones, alcohols, fatty acids, esters, lactones, ethers, or hydrocarbons. The byproducts can remain within the coating and/or are volatilized during the heating process. The cross-links formed by this process can be ester and lactone cross-links, wherein the ester and lactone cross-links occur via esterification, alcoholysis, acidolysis, or interesterification.

In another aspect, the invention may provide a method of forming a fatty acid-derived biomaterial, comprising: continued heating of a fatty acid, thereby oxidizing the double bonds of the unsaturated fatty acid chains while predominantly preserving triglyceride ester functional groups; thereby increasing the viscosity of the biomaterial. The ester linkages can include ester, anhydride, aliphatic peroxide, and lactones. In one embodiment, hydroxyl and carboxyl functional groups are formed from the oxidation process. In still another embodiment, oxidative byproducts of EPA and DHA are formed.

In accordance with various embodiments of the methods provided herein, the curing (heating) steps occur without use of cross-linking agents. Also, curing time and temperature can be adjusted to tailor coating degradation. In another embodiment, vitamin E is added during the process to tailor the degree of cross-linking in the oil-derived biomaterial.

In one embodiment, the starting material used to prepare the biomaterials (e.g., medical device coatings or stand-alone films) of the invention is 40% (area % as determined by GC) polyunsaturated fatty acids.

In one embodiment, the fatty acid-derived biomaterial (e.g., coating or stand-alone film) of the invention has a fatty acid composition that is similar to biological tissue.

In another aspect, the invention may provide a stand-alone film, comprising: a non-polymeric, cross-linked fatty acid, comprising approximately 5-50% $C_{16}$ fatty acids. The stand-alone film can also comprise 5-25% $C_{14}$ fatty acids. In another embodiment, the stand-alone film comprises 5-40%, e.g., 5-30%, $C_{16}$ fatty acids. The stand-alone film can also comprise vitamin E. The stand-alone film and coating may be bioabsorbable and it may maintain anti-adhesive properties. In another embodiment, the stand-alone film can further comprise a therapeutic agent, including, but not limited to, Compound A, Compound B, Compound C, Compound D, Compound E, a cyclosporine derivative or rapamycin derivative. In one embodiment, the therapeutic agent is combined with the fatty acid compound prior to formation of the film, resulting in the therapeutic agent being interspersed throughout the film.

While many of the embodiments described above refer to a "coating" or "coating for a medical device," it will be appreciated that the present invention can be implemented as a coating, as well as a stand-alone material, or other forms as described herein and, as would be understood by those of ordinary skill in the art, having an outer surface and/or coating that interacts with its environment upon implantation. Thus, the embodiments described herein, both those specifically referred to as coatings and those referred to in other forms, to the extent they are based on the fatty acid derived biomaterial as described herein, all are intended to fall within the scope of the present invention.

BRIEF DESCRIPTION OF THE DRAWINGS

The foregoing and other aspects, embodiments, objects, features and advantages of the invention can be more fully understood from the following description in conjunction with the accompanying drawings. In the drawings, like reference characters generally refer to like features and structural elements throughout the various figures. The drawings are not necessarily to scale, emphasis instead being placed upon illustrating the principles of the invention.

FIG. 4 shows a summary of fatty acid-derived biomaterial reaction chemistry;

FIG. 7 shows bar graphs showing similarity of fatty acid composition between a fatty acid-derived biomaterial coating and biological tissue;

FIG. 8 is a flow chart illustrating a method of making the coated medical device of the present invention, in accordance with one embodiment of the present invention;

FIG. 9 is a flow chart illustrating a variation of the method of FIG. 8, in accordance with one embodiment of the present invention;

DETAILED DESCRIPTION

Figure 1:
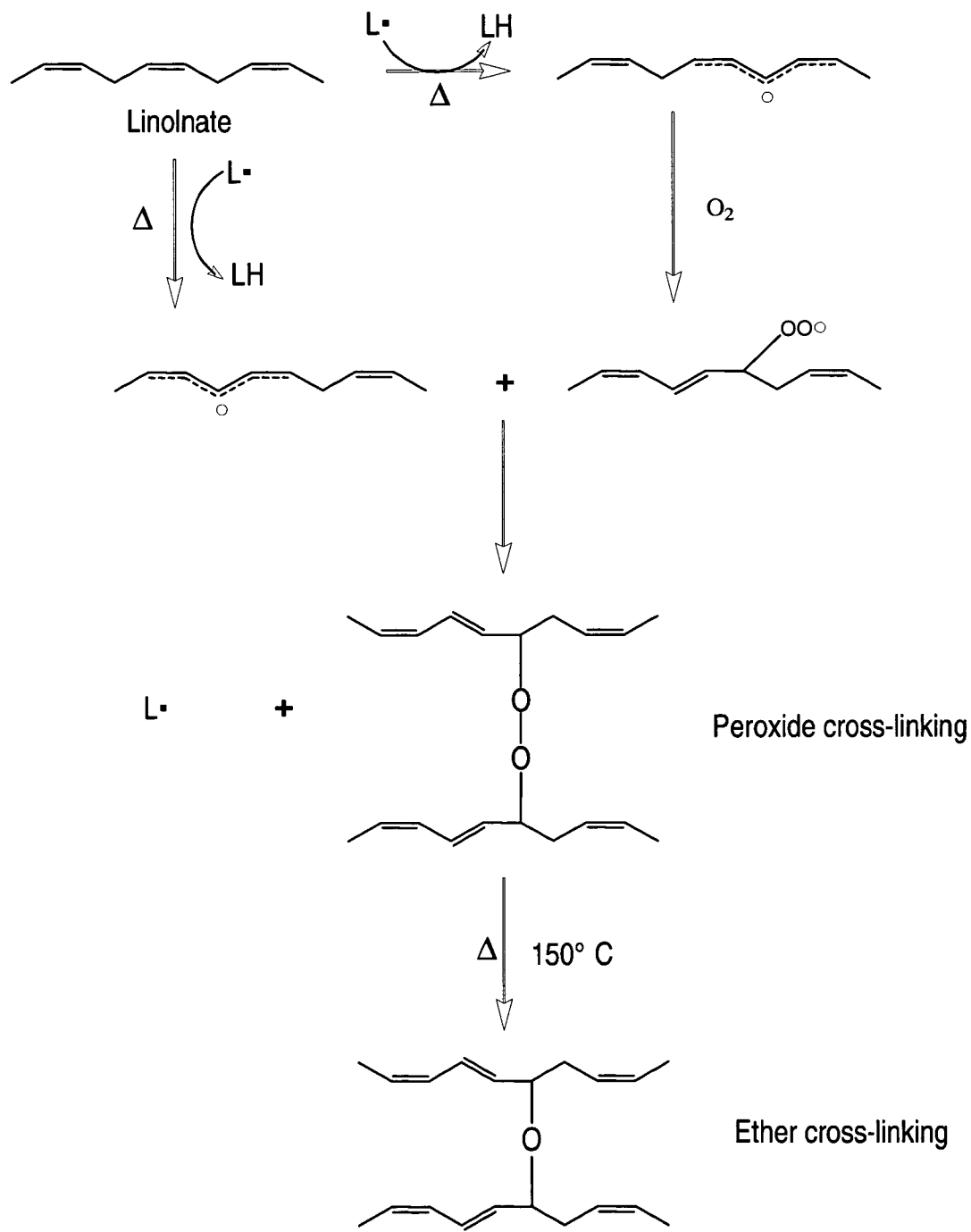
FIG. 1 is a schematic illustration of an example of the creation of peroxide and ether cross-linking in a polyunsaturated oil.

A fatty acid-derived biomaterial can be utilized alone or in combination with a medical device optionally for the release and local delivery of one or more therapeutic agents. Methods of forming and tailoring the properties of said biomaterials and methods of using said biomaterials for treating injury in a mammal are also provided. Additionally, due to the unique properties of the underlying chemistry of the biomaterial, it will be demonstrated that the biomaterial (e.g., coating or stand-alone film) contains specific chemical components that assist in reducing a foreign body response and inflammation at the site of tissue injury during implantation that improves its in-vivo performance.

Prior to further describing embodiments of the invention, it may be helpful to generally and briefly describe injury and the biological response thereto.

Vascular Injury

Vascular injury causing intimal thickening can be broadly categorized as being either biologically or mechanically induced. Biologically mediated vascular injury includes, but is not limited to, injury attributed to infectious disorders including endotoxins and herpes viruses, such as cytomegalovirus; metabolic disorders, such as atherosclerosis; and vascular injury resulting from hypothermia, and irradiation. Mechanically mediated vascular injury includes, but is not limited to, vascular injury caused by catheterization procedures or vascular scraping procedures, such as percutaneous transluminal coronary angioplasty; vascular surgery; transplantation surgery; laser treatment; and other invasive procedures which disrupt the integrity of the vascular intima or endothelium. Generally, neointima formation is a healing response to a vascular injury.

Inflammatory Response

Wound healing upon vascular injury occurs in several stages. The first stage is the inflammatory phase. The inflammatory phase is characterized by hemostasis and inflammation. Collagen exposed during wound formation activates the clotting cascade (both the intrinsic and extrinsic pathways), initiating the inflammatory phase. After injury to tissue occurs, the cell membranes, damaged from the wound formation, release thromboxane A2 and prostaglandin 2-alpha, which are potent vasoconstrictors. This initial response helps to limit hemorrhage. After a short period, capillary vasodilatation occurs secondary to local histamine release, and the cells of inflammation are able to migrate to the wound bed. The timeline for cell migration in a normal wound healing process is predictable. Platelets, the first response cell, release multiple chemokines, including epidermal growth factor (EGF), fibronectin, fibrinogen, histamine, platelet-derived growth factor (PDGF), serotonin, and von Willebrand factor. These factors help stabilize the wound through clot formation. These mediators act to control bleeding and limit the extent of injury. Platelet degranulation also activates the complement cascade, specifically C5a, which is a potent chemoattractant for neutrophils.

As the inflammatory phase continues, more immune response cells migrate to the wound. The second response cell to migrate to the wound, the neutrophil, is responsible for debris scavenging, complement-mediated opsonization of bacteria, and bacteria destruction via oxidative burst mechanisms (i.e., superoxide and hydrogen peroxide formation). The neutrophils kill bacteria and decontaminate the wound from foreign debris.

The next cells present in the wound are the leukocytes and the macrophages (monocytes). The macrophage, referred to as the orchestrator, is essential for wound healing. Numerous enzymes and cytokines are secreted by the macrophage. These include collagenases, which debride the wound; interleukins and tumor necrosis factor (TNF), which stimulate fibroblasts (produce collagen) and promote angiogenesis; and transforming growth factor (TGF), which stimulates keratinocytes. This step marks the transition into the process of tissue reconstruction, i.e., the proliferative phase.

Cell Proliferation

The second stage of wound healing is the proliferative phase. Epithelialization, angiogenesis, granulation tissue formation, and collagen deposition are the principal steps in this anabolic portion of wound healing. Epithelialization occurs early in wound repair. At the edges of wounds, the epidermis immediately begins thickening. Marginal basal cells begin to migrate across the wound along fibrin strands stopping when they contact each other (contact inhibition). Within the first 48 hours after injury, the entire wound is epithelialized. Layering of epithelialization is re-established. The depths of the wound at this point contain inflammatory cells and fibrin strands. Aging effects are important in wound healing as many, if not most, problem wounds occur in an older population. For example, cells from older patients are less likely to proliferate and have shorter life spans and cells from older patients are less responsive to cytokines.

Heart disease can be caused by a partial vascular occlusion of the blood vessels that supply the heart, which is preceded by intimal smooth muscle cell hyperplasia. The underlying cause of the intimal smooth muscle cell hyperplasia is vascular smooth muscle injury and disruption of the integrity of the endothelial lining. Intimal thickening following arterial injury can be divided into three sequential steps: 1) initiation of smooth muscle cell proliferation following vascular injury, 2) smooth muscle cell migration to the intima, and 3) further proliferation of smooth muscle cells in the intima with deposition of matrix. Investigations of the pathogenesis of intimal thickening have shown that, following arterial injury, platelets, endothelial cells, macrophages and smooth muscle cells release paracrine and autocrine growth factors (such as platelet derived growth factor, epidermal growth factor, insulin-like growth factor, and transforming growth factor) and cytokines that result in the smooth muscle cell proliferation and migration. T-cells and macrophages also migrate into the neointima. This cascade of events is not limited to arterial injury, but also occurs following injury to veins and arterioles.

Granulomatous Inflammation

Chronic inflammation, or granulomatous inflammation, can cause further complications during the healing of vascular injury. Granulomas are aggregates of particular types of chronic inflamatory cells which form nodules in the millimeter size range. Granulomas may be confluent, forming larger areas. Essential components of a granuloma are collections of modified macrophages, termed epithelioid cells, usually with a surrounding zone of lymphocytes. Epithelioid cells are so named by tradition because of their histological resemblance to epithelial cells, but are not in fact epithelial; they are derived from blood monocytes, like all macrophages. Epithelioid cells are less phagocytic than other macrophages and appear to be modified for secretory functions. The full extent of their functions is still unclear. Macrophages in granulomas are commonly further modified to form multinucleate giant cells. These arise by fusion of epithelioid macrophages without nuclear or cellular division forming huge single cells which may contain dozens of nuclei. In some circumstances the nuclei are arranged round the periphery of the cell, termed a Langhans-type giant cell; in other circumstances the nuclei are randomly scattered throughout the cytoplasm (i.e., the foreign body type of giant cell which is formed in response to the presence of other indigestible foreign material in the tissue). Areas of granulomatous inflammation commonly undergo necrosis.

Formation of granulomatous inflammation seems to require the presence of indigestible foreign material (derived from bacteria or other sources) and/or a cell-mediated immune reaction against the injurious agent (type IV hypersensitivity reaction).

Fatty Acid-Derived Biomaterials: Coatings and Stand-Alone Films

The fatty acid-derived biomaterials (e.g., coatings and stand-alone films) of the present invention comprise a hydrophobic cross-linked fatty acid-derived biomaterial and optionally one or more therapeutic agents contained in the fatty acid-derived biomaterial. As used in the context of the cross-linked fatty acid-derived biomaterial coating described herein, the terms "soluble" and "insoluble" refer the solubility of the coating in an organic solvent such as, e.g., tetrahydrofuran (THF). In addition, the fatty acid-derived biomaterials (e.g., coatings and stand-alone films) of the present invention are bio-absorbable as described herein. The therapeutic agent can be an active agent as contained in the coating and/or a prodrug that, e.g., becomes active once released from the coating. In one embodiment of the invention, the drug eluting fatty acid-derived biomaterial is a cross-linked fatty acid, e.g., an omega-3 fatty acid. The cross-linked fatty acid can be non-polymeric. The source of the omega-3 fatty acid can be a naturally occurring oil, e.g., a fish oil.

The hydrophobic fatty acid-derived biomaterial coatings and stand-alone films of the present invention can be formed from an oil component. The oil component can be either an oil, or an oil composition. The oil component can be a naturally occurring oil, such as fish oil, cod liver oil, flaxseed oil, grape seed oil, palm oil, or other oils having desired characteristics. The oil can also be a synthetic or non-naturally occurring oil that contains fatty acids. One embodiment of the present invention makes use of a fish oil in part because of the high content of omega-3 fatty acids. The fish oil can also serve as an anti-adhesion agent. In addition, the fish oil maintains anti-inflammatory or non-inflammatory properties as well. The present invention is not limited to formation of the fatty acid-derived biomaterials with fish oil as the oil starting material. However, the following description makes reference to the use of fish oil as one example embodiment. Other oils can be utilized in accordance with the present invention as described herein.

It should be noted that as utilized herein, the term fish oil fatty acid includes, but is not limited to, omega-3 fatty acid, oil fatty acid, free fatty acid, monoglycerides, di-glycerides, or triglycerides, esters of fatty acids, or a combination thereof. The fish oil fatty acid includes one or more of arachidic acid, gadoleic acid, arachidonic acid, eicosapentaenoic acid, docosahexaenoic acid or derivatives, analogs and pharmaceutically acceptable salts thereof. Furthermore, as utilized herein, the term free fatty acid includes but is not limited to one or more of butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, analogs and pharmaceutically acceptable salts thereof. The oils, including fish oil, are cured as described herein to form a hydrophobic cross-linked fatty acid-derived biomaterial.

Some embodiments of the present invention may relate to bio-absorbable medical device coatings and stand-alone films that can exhibit anti-inflammatory properties, non-inflammatory properties, and anti-adhesion properties, and the corresponding method of making. The stand-alone film is generally formed of an oil, such as a fish oil. In addition, the oil composition can include a therapeutic agent component, such as a drug or other bioactive agent. The stand-alone film is implantable in a patient for short term or long term applications. As implemented herein, the stand-alone film can be a non-polymeric cross-linked fatty acid-derived biomaterial derived at least in part from a fatty acid compound, wherein the stand-alone film is prepared in accordance with the methods of the invention. In accordance with further aspects of the present invention, the stand-alone film can further include a vitamin E compound forming a portion of the fatty acid compound.

In accordance with further aspects of the present invention, the stand-alone film further includes a therapeutic agent. The therapeutic agent can include an agent selected from the group consisting of antioxidants, anti-inflammatory agents, anti-coagulant agents, drugs to alter lipid metabolism, antiproliferatives, anti-neoplastics, tissue growth stimulants, functional protein/factor delivery agents, anti-infective agents, imaging agents, anesthetic agents, chemotherapeutic agents, tissue absorption enhancers, anti-adhesion agents, germicides, analgesics, prodrugs, and antiseptics.

In accordance with further aspects of the present invention, the therapeutic agent is combined with the fatty acid compound prior to formation of the film, resulting in the therapeutic agent being interspersed throughout the film. Alternatively, the therapeutic agent is applied to the film in the form of a coating. In accordance with further aspects of the present invention, the stand-alone film is bioabsorbable. The stand-alone film can further maintain anti-adhesive properties.

In accordance with still another embodiment of the present invention, a method of forming a stand-alone film is introduced. The method includes providing a fatty acid compound in liquid form and applying the fatty acid compound to a substrate. The method also includes curing the fatty acid compound to form the stand-alone film. In accordance with one aspect of the present invention, the substrate includes expanded polytetrafluoroethylene (ePTFE) or polytetrafluoroethylene (PTFE). In accordance with further aspects of the present invention, the curing includes using at least one curing method selected from a group of curing methods including application of UV light and application of heat. The UV light can also be applied to set the fatty acid compound by forming a skin on the top surface of the fatty acid compound in liquid form prior to additional curing. In accordance with further aspects of the present invention, the substrate has an indentation that is used as a mold to shape the stand-alone film. Alternatively, the method can further include the step of cutting the film to a desirable shape.

The stand-alone film of the present invention may be used as a barrier to keep tissues separated to avoid adhesion. Application examples for adhesion prevention include abdominal surgeries, spinal repair, orthopedic surgeries, tendon and ligament repairs, gynecological and pelvic surgeries, and nerve repair applications. The stand-alone film may be applied over the trauma site or wrapped around the tissue or organ to limit adhesion formation. The addition of therapeutic agents to the stand-alone films used in these adhesion prevention applications can be utilized for additional beneficial effects, such as pain relief or infection minimization. Other surgical applications of the stand-alone film may include using a stand-alone film as a dura patch, buttressing material, internal wound care (such as a graft anastomotic site), and internal drug delivery system. The stand-alone film may also be used in applications in transdermal, wound healing, and non-surgical fields. The stand-alone film may be used in external wound care, such as a treatment for burns or skin ulcers. The stand-alone film may be used without any therapeutic agent as a clean, non-permeable, non-adhesive, non-inflammatory, anti-inflammatory dressing, or the stand-alone film may be used with one or more therapeutic agents for additional beneficial effects. The stand-alone film may also be used as a transdermal drug delivery patch when the stand-alone film is loaded or coated with one or more therapeutic agents.

Oils

With regard to the aforementioned oils, it is generally known that the greater the degree of unsaturation in the fatty acids the lower the melting point of a fat, and the longer the hydrocarbon chain the higher the melting point of the fat. An unsaturated fat, thus, has a lower melting point, and a saturated fat has a higher melting point. Those fats having a lower melting point are more often oils at room temperature. Those fats having a higher melting point are more often waxes or solids at room temperature. Therefore, a fat having the physical state of a liquid at room temperature is an oil. In general, unsaturated fats are liquid oils at room temperature, and saturated fats are waxes or solids at room temperature.

Polyunsaturated fats are one of four basic types of fat derived by the body from food. The other fats include saturated fat, as well as monounsaturated fat and cholesterol. Unsaturated fats can be further composed of omega-3 fatty acids and omega-6 fatty acids. Under the convention of naming the unsaturated fatty acid according to the position of its first double bond of carbons, those fatty acids having their first double bond at the third carbon atom from the methyl end of the molecule are referred to as omega-3 fatty acids. Likewise, a first double bond at the sixth carbon atom is called an omega-6 fatty acid. There can be both monounsaturated and polyunsaturated omega fatty acids.

Omega-3 and omega-6 fatty acids are also known as essential fatty acids because they are important for maintaining good health, despite the fact that the human body cannot make them on its own. As such, omega-3 and omega-6 fatty acids must be obtained from external sources, such as food. Omega-3 fatty acids can be further characterized as containing eicosapentaenoic acid (EPA), docosahexanoic acid (DHA), and alpha-linolenic acid (ALA). Both EPA and DHA are known to have anti-inflammatory effects and wound healing effects within the human body.

As utilized herein, the term "bio-absorbable" generally refers to having the property or characteristic of being able to penetrate the tissue of a patient's body. In certain embodiments of the present invention bio-absorption occurs through a lipophilic mechanism. The bio-absorbable substance can be soluble in the phospholipid bi-layer of cells of body tissue, and therefore impact how the bio-absorbable substance penetrates into the cells.

It should be noted that a bio-absorbable substance is different from a biodegradable substance. Biodegradable is generally defined as capable of being decomposed by biological agents, or capable of being broken down by microorganisms or biological processes. Biodegradable substances can cause inflammatory response due to either the parent substance or those formed during breakdown, and they may or may not be absorbed by tissues.

Drug Delivery

The fatty acid-derived biomaterials (e.g, coatings and stand-alone films) may deliver one or more therapeutic agents locally to a targeted area using a stand-alone film, medical device or apparatus bearing the coating at a selected targeted tissue location of the patient that requires treatment. The therapeutic agent is released from the coating to the targeted tissue location. The local delivery of a therapeutic agent enables a more concentrated and higher quantity of therapeutic agent to be delivered directly at the targeted tissue location, without having broader systemic side effects. With local delivery, the therapeutic agent that escapes the targeted tissue location dilutes as it travels to the remainder of the patient's body, substantially reducing or eliminating systemic side effects.

Targeted local therapeutic agent delivery using a fatty acid-derived biomaterial (e.g, coatings and stand-alone films) can be further broken into two categories, namely, short term and long term. The short term delivery of a therapeutic agent occurs generally within a matter of seconds or minutes to a few days or weeks. The long term delivery of a therapeutic agent occurs generally within weeks to months.

The phrase "sustained release" as used herein generally refers to the release of a biologically active agent that results in the long term delivery of the active agent.

The phrase "controlled release" as used herein generally refers to the release of a biologically active agent in a substantially predictable manner over the time period of weeks or months, as desired and predetermined upon formation of the biologically active agent on the medical device from which it is being released. Controlled release includes the provision of an initial burst of release upon implantation, followed by the substantially predictable release over the aforementioned time period.

Drug Release Mechanisms

Prior attempts to create films and drug delivery platforms, such as in the field of stents, primarily make use of high molecular weight synthetic polymer based materials to provide the ability to better control the release of the therapeutic agent. Essentially, the polymer in the platform releases the drug or agent at a predetermined rate once implanted at a location within the patient. Regardless of how much of the therapeutic agent would be most beneficial to the damaged tissue, the polymer releases the therapeutic agent based on properties of the polymer, e.g., erosion of the polymeric material or diffusion of the agent through the polymer. Accordingly, the effect of the therapeutic agent is substantially local at the surface of the tissue making contact with the medical device having the coating. In some instances the effect of the therapeutic agent is further localized to the specific locations of, for example, stent struts or mesh pressed against the tissue location being treated. These prior approaches can create the potential for a localized toxic effect.

In various embodiments of the present invention, the fatty acid-derived biomaterial of the invention (e.g., coatings and stand-alone films) release one or more therapeutic agents by a dissolution mechanism, e.g., dissolution of a therapeutic agent contained in a soluble component of the coating into the medium in contact with the coating, e.g., tissue. As a result, the drug release mechanism can be based on the solubility of the therapeutic agent in the surrounding medium. For example, a therapeutic agent near the interface between the hydrophobic coating and the surrounding medium can experience a chemical potential gradient that can motivate the therapeutic agent out of the oil based coating and into the surrounding medium. Accordingly, in various embodiments, the release of a therapeutic agent is not rate-limited by diffusion or the hydrolysis of the coating.

In various embodiments, the break-down products of the fatty acid-derived biomaterial of the invention, e.g., a hydrophobic, cross-linked fatty acid-derived biomaterial, break-down into non-inflammatory byproducts, e.g., free fatty acids and glycerides, that themselves can release one or more of the therapeutic agents via a dissolution mechanism.

Therapeutic Agents

As utilized herein, the phrase "therapeutic agent(s)" refers to a number of different drugs or agents available, as well as future agents that may be beneficial for use with the fatty acid-derived biomaterials (e.g., coatings and stand-alone films) of the present invention. The therapeutic agent component can take a number of different forms including anti-oxidants, anti-inflammatory agents, anti-coagulant agents, drugs to alter lipid metabolism, anti-proliferatives, anti-neoplastics, tissue growth stimulants, functional protein/factor delivery agents, anti-infective agents, anti-imaging agents, anesthetic agents, therapeutic agents, tissue absorption enhancers, anti-adhesion agents, germicides, anti-septics, analgesics, prodrugs thereof, and any additional desired therapeutic agents such as those listed in Table 1 below.

TABLE 1

| CLASS | EXAMPLES |
| --- | --- |
| Antioxidants | Alpha-tocopherol, lazaroid, probucol, phenolic antioxidant, resveretrol, AGI-1067, vitamin E |
| Antihypertensive Agents | Diltiazem, nifedipine, verapamil |
| Antiinflammatory Agents | Glucocorticoids (e.g. dexamethazone, methylprednisolone), leflunomide, NSAIDS, ibuprofen, acetaminophen, hydrocortizone acetate, hydrocortizone sodium phosphate, macrophage-targeted bisphosphonates |
| Growth Factor Antagonists | Angiopeptin, trapidil, suramin |
| Antiplatelet Agents | Aspirin, dipyridamole, ticlopidine, clopidogrel, GP IIb/IIIa inhibitors, abciximab |
| Anticoagulant Agents | Bivalirudin, heparin (low molecular weight and unfractionated), wafarin, hirudin, enoxaparin, citrate |
| Thrombolytic Agents | Alteplase, reteplase, streptase, urokinase, TPA, citrate |
| Drugs to Alter Lipid Metabolism (e.g. statins) | Fluvastatin, colestipol, lovastatin, atorvastatin, amlopidine |
| ACE Inhibitors | Elanapril, fosinopril, cilazapril |
| Antihypertensive Agents | Prazosin, doxazosin |
| Antiproliferatives and Antineoplastics | Cyclosporine, cochicine, mitomycin C, sirolimus micophenonolic acid, rapamycin, everolimus, tacrolimus, paclitaxel, QP-2, actinomycin, estradiols, dexamethasone, methatrexate, cilostazol, prednisone, cyclosporine, doxorubicin, ranpirnas, troglitzon, valsarten, pemirolast, C-MYC antisense, angiopeptin, vincristine, PCNA ribozyme, 2-chloro-deoxyadenosine, mTOR targeting compounds |
| Tissue growth stimulants | Bone morphogeneic protein, fibroblast growth factor |
| Promotion of hollow organ occlusion or thrombosis | Alcohol, surgical sealant polymers, polyvinyl particles, 2-octyl cyanoacrylate, hydrogels, collagen, liposomes |
| Functional Protein/Factor delivery | Insulin, human growth hormone, estradiols, nitric oxide, endothelial progenitor cell antibodies |
| Second messenger targeting | Protein kinase inhibitors |
| Angiogenic | Angiopoetin, VEGF |
| Anti-Angiogenic | Endostatin |
| Inhibition of Protein Synthesis/ECM formation | Halofuginone, prolyl hydroxylase inhibitors, C-proteinase inhibitors |
| Antiinfective Agents | Penicillin, gentamycin, adriamycin, cefazolin, amikacin, ceftazidime, tobramycin, levofloxacin, silver, copper, hydroxyapatite, vancomycin, ciprofloxacin, rifampin, mupirocin, RIP, kanamycin, brominated furonone, algae byproducts, bacitracin, oxacillin, nafcillin, floxacillin, clindamycin, cephradin, neomycin, methicillin, oxytetracycline hydrochloride, Selenium. |
| Gene Delivery | Genes for nitric oxide synthase, human growth hormone, antisense oligonucleotides |
| Local Tissue perfusion | Alcohol, H2O, saline, fish oils, vegetable oils, liposomes |
| Nitric oxide Donor Derivatives | NCX 4016 - nitric oxide donor derivative of aspirin, SNAP |
| Gases | Nitric oxide, compound solutions |
| Imaging Agents | Halogenated xanthenes, diatrizoate meglumine, diatrizoate sodium |
| Anesthetic Agents | Lidocaine, benzocaine |
| Descaling Agents | Nitric acid, acetic acid, hypochlorite |
| Anti-Fibrotic Agents | Interferon gamma - 1b, Interluekin - 10 |
| Immunosuppressive/Immunomodulatory Agents | Cyclosporine, rapamycin, mycophenolate motefil, leflunomide, tacrolimus, tranilast, interferon gamma-1b, mizoribine, mTOR targeting compounds |
| Chemotherapeutic Agents | Doxorubicin, paclitaxel, tacrolimus, sirolimus, fludarabine, ranpirnase |
| Tissue Absorption Enhancers | Fish oil, squid oil, omega 3 fatty acids, vegetable oils, lipophilic and hydrophilic solutions suitable for enhancing medication tissue absorption, distribution and permeation |
| Anti-Adhesion Agents | Hyaluronic acid, human plasma derived surgical sealants, and agents comprised of hyaluronate and carboxymethylcellulose that are combined with dimethylaminopropyl, ehtylcarbodimide, hydrochloride, PLA, PLGA |
| Ribonucleases | Ranpirnase |
| Germicides | Betadine, iodine, sliver nitrate, furan derivatives, nitrofurazone, benzalkonium chloride, benzoic acid, salicylic acid, hypochlorites, peroxides, thiosulfates, salicylanilide |
| Antiseptics | Selenium |
| Analgesics | Bupivicaine, naproxen, ibuprofen, acetylsalicylic acid |

Some specific examples of therapeutic agents useful in the anti-restenosis realm include cerivastatin, cilostazol, fluvastatin, lovastatin, paclitaxel, pravastatin, rapamycin, a rapamycin carbohydrate derivative (for example, as described in US Patent Application Publication 2004/0235762), a rapamycin derivative (for example, as described in U.S. Pat. No. 6,200,985), everolimus, seco-rapamycin, seco-everolimus, and simvastatin. With systemic administration, the therapeutic agent is administered orally or intravenously to be systemically processed by the patient. However, there are drawbacks to a systemic delivery of a therapeutic agent, one of which is that the therapeutic agent travels to all portions of the patient's body and can have undesired effects at areas not targeted for treatment by the therapeutic agent. Furthermore, large doses of the therapeutic agent only amplify the undesired effects at non-target areas. As a result, the amount of therapeutic agent that results in application to a specific targeted location in a patient may have to be reduced when administered systemically to reduce complications from toxicity resulting from a higher dosage of the therapeutic agent.

The term "mTOR targeting compound" refers to any compound which modulates mTOR directly or indirectly. An example of an "mTOR targeting compound" is a compound that binds to FKBP 12 to form, e.g., a complex, which in turn inhibits phosphoinostide (PI)-3 kinase, that is, mTOR. In various embodiments, mTOR targeting compounds inhibit mTOR. Suitable mTOR targeting compounds include, for example, rapamycin and its derivatives, analogs, prodrugs, esters and pharmaceutically acceptable salts.

Calcineurin is a serine/threonine phospho-protein phosphatase and is composed of a catalytic (calcineurin A) and regulatory (calcineurin B) subunit (about 60 and about 18 kDa, respectively). In mammals, three distinct genes (A-alpha, A-beta, A-gamma) for the catalytic subunit have been characterized, each of which can undergo alternative splicing to yield additional variants. Although mRNA for all three genes appears to be expressed in most tissues, two isoforms (A-alpha and A-beta) are most predominant in brain.

The calcineurin signaling pathway is involved in immune response as well as apoptosis induction by glutamate excitotoxicity in neuronal cells. Low enzymatic levels of calcineurin have been associated with Alzheimers disease. In the heart or in the brain calcineurin also plays a key role in the stress response after hypoxia or ischemia.

Substances which are able to block the calcineurin signal pathway can be suitable therapeutic agents for the present invention. Examples of such therapeutic agents include, but are not limited to, FK506, tacrolimus, cyclosporin and include derivatives, analogs, esters, prodrugs, pharmaceutically acceptably salts thereof, and conjugates thereof which have or whose metabolic products have the same mechanism of action. Further examples of cyclosporin derivatives include, but are not limited to, naturally occurring and non-natural cyclosporins prepared by total- or semi-synthetic means or by the application of modified culture techniques. The class comprising cyclosporins includes, for example, the naturally occurring Cyclosporins A through Z, as well as various non-natural cyclosporin derivatives, artificial or synthetic cyclosporin derivatives. Artificial or synthetic cyclosporins can include dihydrocyclosporins, derivatized cyclosporins, and cyclosporins in which variant amino acids are incorporated at specific positions within the peptide sequence, for example, dihydro-cyclosporin D.

In various embodiments, the therapeutic agent comprises one or more of a mTOR targeting compound and a calcineurin inhibitor. In various embodiments, the mTOR targeting compound is Compound D or a derivative, analog, ester, prodrug, pharmaceutically acceptably salts thereof, or conjugate thereof which has or whose metabolic products have the same mechanism of action. In various embodiments, the calcineurin inhibitor is a compound of Tacrolimus, or a derivative, analog, ester, prodrug, pharmaceutically acceptably salts thereof, or conjugate thereof which has or whose metabolic products have the same mechanism of action or a compound of Cyclosporin or a derivative, analog, ester, prodrug, pharmaceutically acceptably salts thereof, or conjugate thereof which has or whose metabolic products have the same mechanism of action.

The therapeutic agents that can be used with the fatty acid-derived, pre-cured biomaterials of the invention can also include antimicrobial agents, including, antivirals, antibiotics, antifungals and antiparasitics. Specific antimicrobial agents that can be used with the fatty acid-derived, pre-cured biomaterials of the invention include Penicillin G, ephalothin, Ampicillin, Amoxicillin, Augmentin, Aztreonam, Imipenem, Streptomycin, Gentamicin, Vancomycin, Clindamycin, Erythromycin, Azithromycin, Polymyxin, Bacitracin, Amphotericin, Nystatin, Rifampicin, Tetracycline, Doxycycline, Chloramphenicol, Nalidixic acid, Ciprofloxacin, Sulfanilamide, Gantrisin, Trimethoprim, Isoniazid (INH), para-aminosalicylic acid (PAS), and Gentamicin.

Therapeutically Effective Amounts and Dosage Levels

A therapeutically effective amount refers to that amount of a compound sufficient to result in amelioration of symptoms, e.g., treatment, healing, prevention or amelioration of the relevant medical condition, or an increase in rate of treatment, healing, prevention or amelioration of such conditions. When applied to an individual active ingredient, administered alone, a therapeutically effective amount refers to that ingredient alone. When applied to a combination, a therapeutically effective amount can refer to combined amounts of the active ingredients that result in the therapeutic effect, whether administered in combination, serially or simultaneously. In various embodiments, where formulations comprise two or more therapeutic agents, such formulations can be described as a therapeutically effective amount of compound A for indication A and a therapeutically effective amount of compound B for indication B, such descriptions refer to amounts of A that have a therapeutic effect for indication A, but not necessarily indication B, and amounts of B that have a therapeutic effect for indication B, but not necessarily indication A.

Actual dosage levels of the active ingredients in a fatty acid-derived biomaterial (e.g., coating and stand-alone film) of the present invention may be varied so as to obtain an amount of the active ingredients which is effective to achieve the desired therapeutic response without being unacceptably toxic. The selected dosage level will depend upon a variety of pharmacokinetic factors including the activity of the particular therapeutic agent (drug) employed, or the ester, salt or amide thereof, the mechanism of drug action, the time of administration, the drug release profile of the coating, the rate of excretion of the particular compounds being employed, the duration of the treatment, other drugs, compounds and/or materials used in combination with the particular compounds employed, and like factors known in the medical arts.

Other Agents

The fatty acid-derived biomaterials (e.g., coatings and stand-alone films) of the present invention can also comprise one or more other chemicals and entities in addition to the therapeutic agent, including, but not limited to, one or more of: a pharmaceutically acceptable carrier, an excipient, a surfactant, a binding agent, an adjuvant agent, and/or a stabilizing agent (including preservatives, buffers and antioxidants).

The other agents can perform one or more functions, such as, e.g., an adjuvant may also serve as a stabilizing agent.

In various embodiments, the coatings and stand-alone films of the present invention include one or more of a free radical scavenger and uptake enhancer. In various embodiments, the coatings and stand-alone films comprise vitamin E.

It should be noted that as utilized herein to describe the present invention, the term vitamin E and the term alpha-tocopherol, are intended to refer to the same or substantially similar substance, such that they are interchangeable and the use of one includes an implicit reference to both. Further included in association with the term vitamin E are such variations including but not limited to one or more of alpha-tocopherol, beta-tocopherol, delta-tocopherol, gamma-tocopherol, alpha-tocotrienol, beta-tocotrienol, delta-tocotrienol, gamma-tocotrienol, alpha-tocopherol acetate, beta-tocopherol acetate, gamma-tocopherol acetate, delta-tocopherol acetate, alpha-tocotrienol acetate, beta-tocotrienol acetate, delta-tocotrienol acetate, gamma-tocotrienol acetate, alpha-tocopherol succinate, beta-tocopherol succinate, gamma-tocopherol succinate, delta-tocopherol succinate, alpha-tocotrienol succinate, beta-tocotrienol succinate, delta-tocotrienol succinate, gamma-tocotrienol succinate, mixed tocopherols, vitamin E TPGS, derivatives, analogs and pharmaceutically acceptable salts thereof.

Compounds that move too rapidly through a tissue may not be effective in providing a sufficiently concentrated dose in a region of interest. Conversely, compounds that do not migrate in a tissue may never reach the region of interest. Cellular uptake enhancers such as fatty acids and cellular uptake inhibitors such as alpha-tocopherol can be used alone or in combination to provide an effective transport of a given compound to a given region or location. Both fatty acids and alpha-tocopherol can be included in the fatty acid-derived biomaterials (e.g., coatings and stand-alone films) of the present invention described herein. Accordingly, fatty acids and alpha-tocopherol can be combined in differing amounts and ratios to contribute to a fatty acid-derived biomaterial (e.g., coating and stand-alone film) in a manner that provides control over the cellular uptake characteristics of the coating and any therapeutic agents mixed therein.

For example, the amount of alpha-tocopherol can be varied in the coating. Alpha-tocopherol is known to slow autoxidation in fish oil by reducing hydroperoxide formation, which results in a decrease in the amount of cross-linking in a cured fatty acid-derived biomaterial. In addition, alpha-tocopherol can be used to increase solubility of drugs in the oil forming the coating. In various embodiments, alpha-tocopherol can protect the therapeutic drug during curing, which increases the resulting drug load in the coating after curing. Furthermore, with certain therapeutic drugs, the increase of alpha-tocopherol in the coating can serve to slow and extend drug release due to the increased solubility of the drug in the alpha-tocopherol component of the coating.

Curing and the Formation of Fatty Acid-Derived Biomaterials

Several methods are available to cure the oil starting material containing one or more therapeutic agents to produce a fatty acid-derived biomaterial for a drug release and delivery coating or stand-alone film in accordance with the present invention (for example, as described in US Patent Application Publications 2008/0118550, 2007/0202149, 2007/0071798, 2006/0110457, 2006/0078586, 2006/0067983, 2006/0067976, 2006/0067975, which are incorporated herein by reference). Preferred methods for curing the starting material to produce a fatty acid-derived biomaterial of the present invention include, but are not limited to, heating (e.g., employing an oven, a broadband infrared (IR) light source, a coherent IR light source (e.g., laser), and combinations thereof) and ultraviolet (UV) irradiation. The starting material may be cross-linked through auto-oxidation (i.e., oxidative cross-linking).

In accordance with various embodiments described herein, the drug release coatings of the present invention are formed of a fatty acid-derived biomaterial, which can be derived from saturated and unsaturated fatty acid compounds (e.g., free fatty acids, fatty acid ester, monoglycerides, diglycerides, triglycerides, metal salts, etc.). Preferably, the source of fatty acids described in this invention is saturated and unsaturated fatty acids such as those readily available in triglyceride form in various oils (e.g., fish oils). One method of the formation of a fatty acid-derived biomaterial is accomplished through autoxidation of the oil. As a liquid oil containing unsaturated fatty acid is heated, autoxidation occurs with the absorption of oxygen into the oil to create hydroperoxides in an amount dependent upon the amount of unsaturated (C=C) sites in the oil. However, the (C=C) bonds are not consumed in this initial reaction. Concurrent with the formation of hydroperoxides is the isomerization of (C=C) double bonds from cis to trans in addition to double bond conjugation. Continued heating of the oil results in the solidifying of the coating through the formation of cross-linking and by the further reaction of the hydroperoxides and the cleavage of C=C double bonds, which convert them into secondary oxidation byproducts including aldehydes, ketones, alcohols, fatty acids, esters, lactones, ethers, and hydrocarbons which can either remain within the coating and/or are volatilized during the process.

Figure 2:
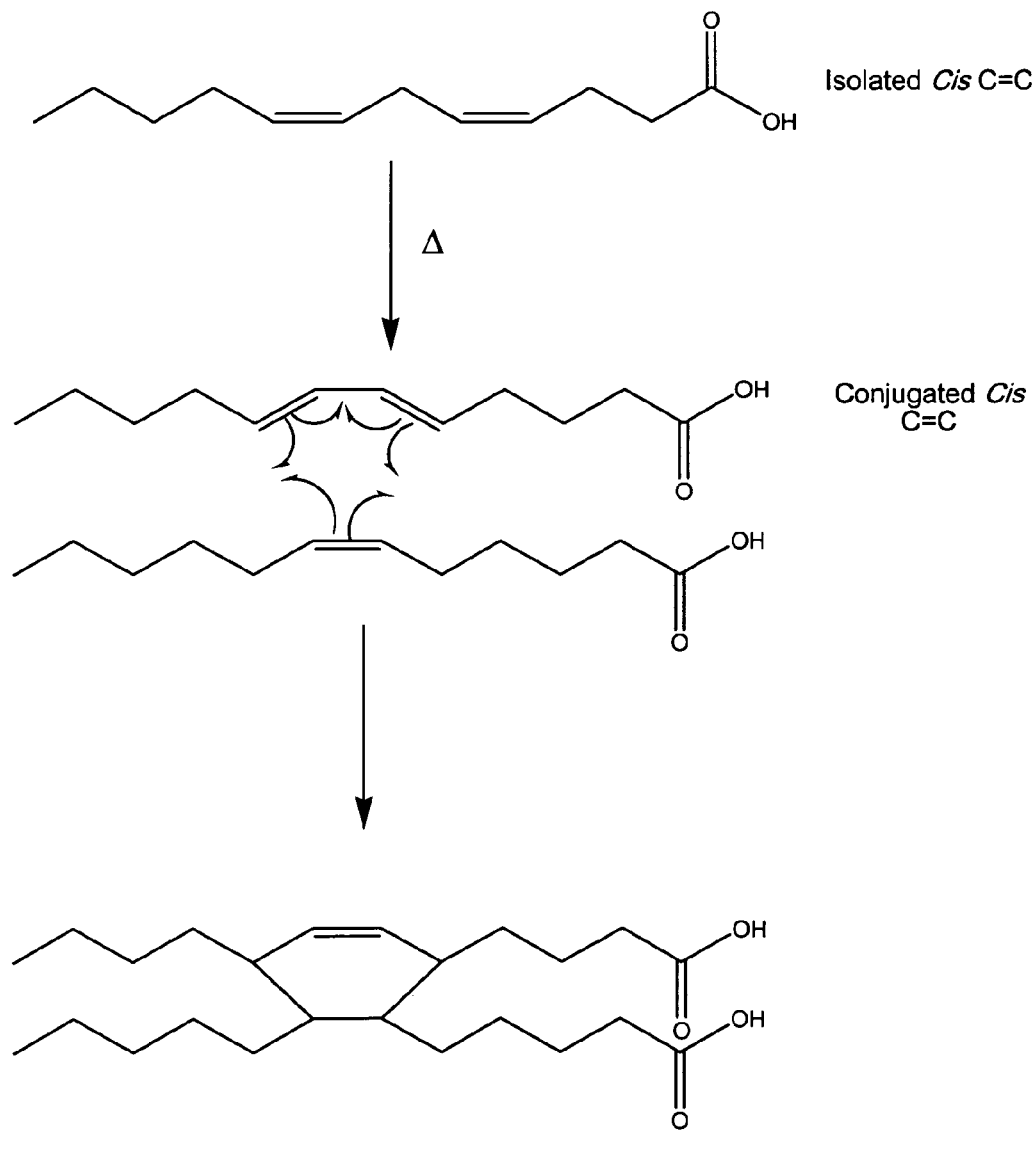
FIG. 2 is a schematic illustration of an example of the creation of carbon-carbon cross-linking in a polyunsaturated oil (Diels-Alder type reaction)

The type and amount of cross-links formed during oil oxidation can be tailored depending on the conditions selected (e.g., coating thickness, temperature, metal composition, etc.). For instance, heating of the oil allows for cross-linking between the fish oil unsaturated chains using a combination of peroxide (C—O—O—C), ether (C—O—C), and hydrocarbon (C—C) bridges (see, e.g., F. D. Gunstone, "Fatty Acid and Lipid Chemistry." 1999). However, heating at lower temperatures (i.e., below 150° C.) results in the formation of predominantly peroxide cross-links where heating at higher temperatures (i.e., above 150° C.) results in the thermal degradation of peroxides and C=C and ether cross-links dominate (F. D. Gunstone, 1999). Schematic illustrations of various cross-linking mechanisms and schemes are shown in FIGS. 1-2.

In addition to thermal curing processes, oxidation of oils can also be induced by light (e.g., photo-oxygenation). Photo-oxygenation is limited to C=C carbon atoms and results in a conversion from cis to trans C=C isomers during curing (as occurs with heat initiated curing). However, photo-oxygenation using UV is a relatively quicker reaction than autoxidation from heat curing, in the realm of about 1000-1500 times faster. The quicker reaction especially holds true for methylene interrupted polyunsaturated fatty acids, such as EPA and DHA, which are found in the fish oil based embodiments of the present invention.

An important aspect of UV curing when compared to heat curing is that although the byproducts obtained by both curing methods are similar, they are not necessarily identical in amount or chemical structure. One reason for this is due to the ability of photo-oxygenation to create hydroperoxides at more possible C=C sites.

Photo-oxygenation, such as that which results from UV curing, due to its enhanced ability to create inner hydroperoxides, also results in the ability to form relatively greater amounts of cyclic byproducts, which also relates to peroxide cross-linking between fish oil hydrocarbon chains. For example, photo-oxygenation of linolenate results in 6 different types of hydroperoxides to be formed, whereas autoxidation results in only 4. The greater amount of hydroperoxides created using photo-oxygenation results in a similar, but slightly different, structure and amount of secondary byproducts to be formed relative to autoxidation from heat curing. Specifically, these byproducts are aldehydes, ketones, alcohols, fatty acids, esters, lactones, ethers, and hydrocarbons.

Figure 3:
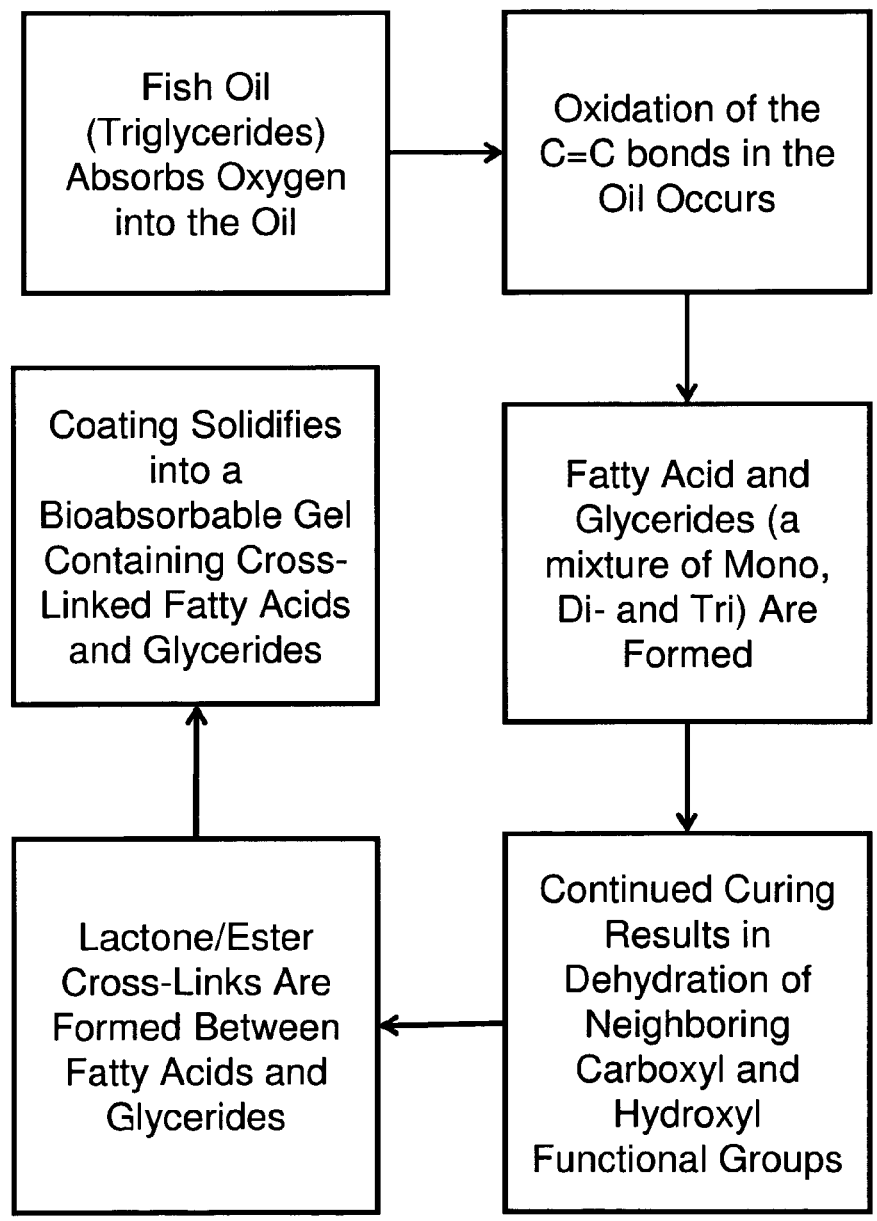
FIG. 3 shows the mechanism for the formation of the hydrophobic fatty acid-derived cross-linked biomaterial coating.
Figure 5:
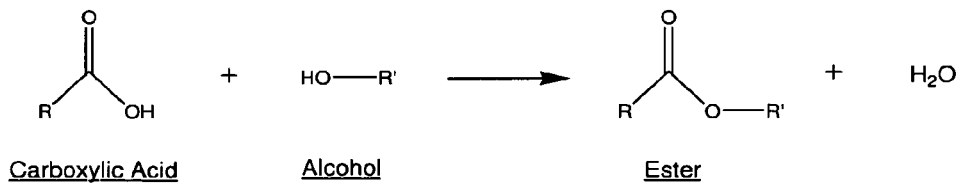
FIG. 5 is a schematic of reactions of fatty acids that result in the formation of ester groups.
Figure 5:
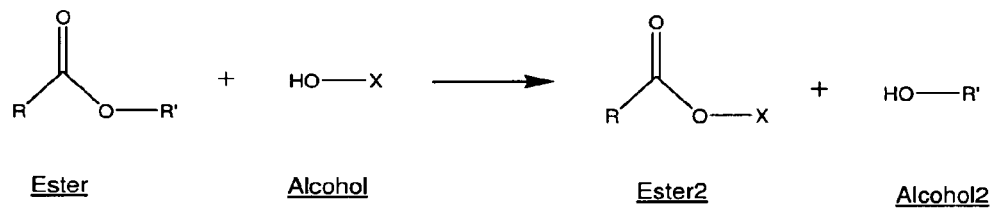
Figure 5:
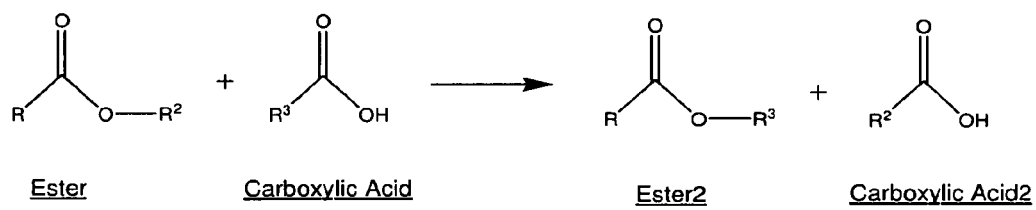
Figure 5:
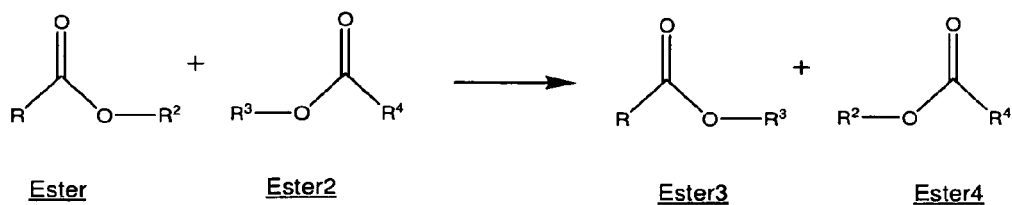

Depending on the oil curing conditions and the fatty acid composition of the starting oil, a fatty acid-derived biomaterial can be produced by curing the oil so as to oxidize the double bonds of the unsaturated fatty acid chains while predominantly preserving triglyceride ester functional groups. The oxidation of the unsaturated fatty acid chains results in the formation of hydroperoxides, which, with continued curing, are converted into and aldehydes, ketones, alcohols, fatty acids, esters, lactones, ethers, and hydrocarbons. With continued heating of the oxidized oil, the byproducts are volatilized, resulting in an increase in the coating viscosity in addition to the formation of ester cross-links. The formation of ester and lactone cross-links can occur via different types of mechanisms (i.e., esterification, alcoholysis, acidolysis, interesterification as described in F. D. Gunstone, 1999, Chapter 8, incorporated herein by reference) between the hydroxyl and carboxyl functional components in the coating formed from the oxidation process (i.e., glyceride and fatty acid). The cross-linking reaction can form different types of ester linkages such as ester, anhydride, aliphatic peroxide, and lactones. FIGS. 3-4 summarize the mechanism for the formation of the oil derived biomaterial and reaction chemistry, respectively. FIG. 5 provides a schematic of different methods to form esters from oils reaction schemes for illustrative purposes, but is not meant to be limiting in its scope to the invention.

Fatty acid-derived biomaterial coatings and stand-alone films of the present invention are formed from an oil component. The term "oil component" is also referred to herein as the "oil acid-containing starting material" or "fatty acid-containing starting material." The "fatty acid-containing starting material" may be natural or derived from synthetic sources. Preferably, the "oil containing starting material" comprises unsaturated fatty acids. The oil component can be either an oil, or an oil composition. The oil component can be a naturally occurring oil, such as fish oil, flax seed oil, grape seed oil, palm oil, a synthetic oil, or other oils having desired characteristics. The oil can also be a synthetic oil. One embodiment of the present invention makes use of a fish oil in part because of the high content of omega-3 fatty acids, which can provide healing support for damaged tissue, as discussed herein. The fish oil can also serve as an anti-adhesion agent. In addition, the fish oil maintains anti-inflammatory or non-inflammatory properties as well. The present invention is not limited to formation of the fatty acid-derived biomaterial with fish oil as the oil. However, the following description makes reference to the use of fish oil as one example embodiment. Other naturally occurring oils or synthetic oils can be utilized in accordance with the present invention as described herein.

Figure 6:
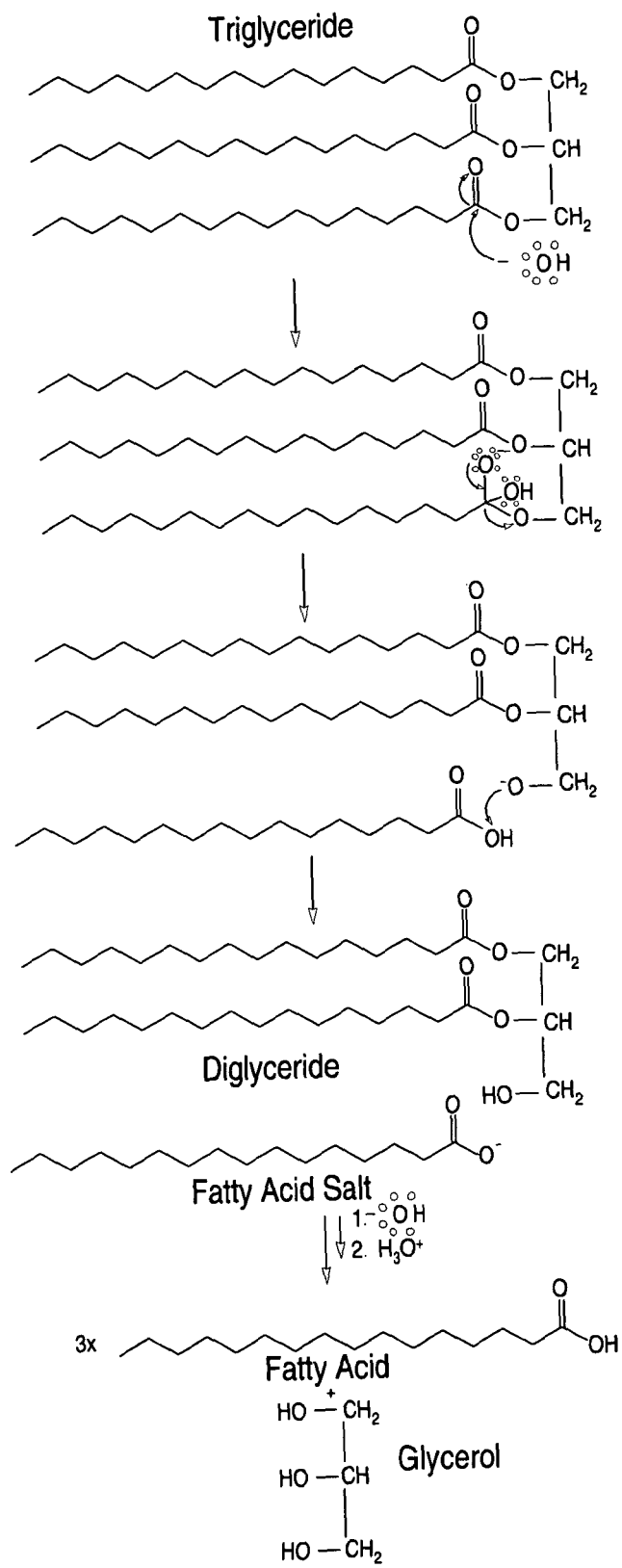
FIG. 6 schematically depicts the hydrolysis of the ester links in a triglyceride.

Coating Hydrolysis and Bioabsorption Chemistry of Fatty Acid-Derived Biomaterials Biodegradable and bioabsorbable implantable materials with ester, lactone, and anhydride functional groups are typically broken down by either chemical and/or enzymatic hydrolysis mechanisms (K. Park et al., "Biodegradable Hydrogels for Drug Delivery." 1993; J. M. Andersen, "Perspectives on the In-Vivo Responses of Biodegradable Polymers." in *Biomedical Applications of Synthetic Biodegradable Polymers*, edited by Jeffrey O. Hollinger. 1995, pgs 223-233). Chemical hydrolysis of a fatty acid-derived biomaterial occurs when the functional group present in the material is cleaved by water. An example of chemical hydrolysis of a triglyceride under basic conditions is presented in FIG. 6. Enzymatic hydrolysis is the cleavage of functional groups in a fatty acid-derived biomaterial caused by the reaction with a specific enzyme (i.e., triglycerides are broken down by lipases (enzymes) that result in free fatty acids that can than be transported across cell membranes). The length of time a biodegradable and/or biodegradable fatty acid-derived biomaterial takes to be hydrolyzed is dependent on several factors such as the cross-linking density of the material, the thickness, the hydration ability of the coating, the crystallinity of the fatty acid-derived biomaterial, and the ability for the hydrolysis products to be metabolized by the body (K. Park et al., 1993 and J. M. Andersen, 1995).

It should be noted that a bio-absorbable substance is different from a biodegradable substance. Biodegradable is generally defined as capable of being decomposed by biological agents, or capable of being broken down by microorganisms or biological processes. Biodegradable substances can cause inflammatory response due to either the parent substance or those formed during hydrolysis, and they may or may not be absorbed by tissues. Some biodegradable substances are limited to bulk erosion mechanism for hydrolysis. For example, a commonly used biodegradable polymer, PLGA (poly(lactic-co-glycolic acid)) undergoes chemical hydrolysis in-vivo to form two alpha-hydroxy acids, specifically glycolic and lactic acids. Although glycolic and lactic acids are byproducts of various metabolic pathways in the body, it has been previously demonstrated in previous medical implant and local drug delivery applications that a local concentration of these products results in an acidic environment to be produced, which can lead to inflammation and damage to local tissue (S. Dumitriu, "Polymeric Biomaterials." 2002). Clinically, this can lead to impaired clinical outcomes such as restenosis (D. E. Drachman and D. I. Simon. *Current Atherosclerosis Reports*. 2005, Vol 7, pgs 44-49; S. E. Goldblum et al. *Infection and Immunity*. 1989, Vol. 57, No. 4, pgs 1218-1226) and impaired healing in a coronary stent application which can lead to late-stent thrombosis or adhesion formation in an abdominal hernia repair (Y. C. Cheong et al. *Human Reproduction Update*. 2001; Vol. 7, No. 6: pgs 556-566). Thus, an ideal fatty acid-derived biomaterial should not only demonstrate excellent biocompatibility upon implantation, but should also maintain that biocompatibility during the life of its implantation with its hydrolysis byproducts being absorbable by local tissue.

The bio-absorbable nature of the fatty acid-derived biomaterials used as a stand-alone film, a coating for a medical device, or in drug delivery applications results in the biomaterial being absorbed over time by the cells of the body tissue. In various embodiments, there are substantially no substances in the coating, or in vivo conversion by-products of the coating, which induce an inflammatory response, e.g., the coating converts in vivo into non-inflammatory components. For example, in various embodiments, the coatings of the present invention upon absorption and hydrolysis do not produce lactic acid and glycolic acid break-down products in measurable amounts. The chemistry of the fatty acid-derived biomaterial described in this invention consists of predominantly fatty acid and glyceride components, which can either be hydrolyzed in-vivo by chemical and/or enzymatic means, and which results in the release of fatty acid and glyceride components that can be transported across cell membranes. Subsequently, the fatty acid and glyceride components eluted from the fatty acid-derived biomaterial are directly metabolized by cells (i.e., they are bio-absorbable). The bio-absorbable nature of the coating and stand-alone film of the present invention results in the coating being absorbed over time, leaving only an underlying delivery or other medical device structure that is biocompatible. There is substantially no foreign body inflammatory response to the bio-absorbable coating or its hydrolysis hydrolysis products in the preferred embodiments of the present invention.

Fatty Acid-Derived Biomaterial Biocompatibility and In-Vivo Performance

The process of making the fatty acid-derived biomaterials (e.g., coating or stand-alone film) as described in this invention led to some unexpected chemical processes and characteristics in view of traditional scientific reports in the literature about the oxidation of oils (J. Dubois et al. *JAOCS*. 1996, Vol. 73, No. 6, pgs 787-794. H. Ohkawa et al., *Analytical Biochemistry*, 1979, Vol. 95, pgs 351-358; H. H. Draper, 2000, Vol. 29, No. 11, pgs 1071-1077). Oil oxidation has traditionally been of concern for oil curing procedures due to the formation of reactive byproducts such as hydroperoxides and alpha-beta unsaturated aldehydes that are not considered to be biocompatible (H. C. Yeo et al. *Methods in Enzymology*. 1999, Vol. 300, pgs 70-78; S-S. Kim et al. *Lipids*. 1999, Vol. 34, No. 5, pgs 489-496). However, the oxidation of fatty acids from oils and fats are normal and important in the control of biochemical processes in-vivo. For example, the regulation of certain biochemical pathways, such as to promote or reduce inflammation, is controlled by different lipid oxidation products (V. N. Bochkov and N. Leitinger. *J. Mol. Med.* 2003; Vol. 81, pgs 613-626). Additionally, omega-3 fatty acids are known to be important for human health and specifically EPA and DHA are known to have anti-inflammatory properties in-vivo. However, EPA and DHA are not anti-inflammatory themselves, but it is the oxidative byproducts they are biochemically converted into that produce anti-inflammatory effects in-vivo (V. N. Bochkov and N. Leitinger, 2003; L. J. Roberts II et al. *The Journal of Biological Chemistry*. 1998; Vol. 273, No. 22, pgs 13605-13612). Thus, although there are certain oil oxidation products that are not biocompatible, there are also several others that have positive biochemical properties in-vivo (V. N. Bochkov and N. Leitinger, 2003; F. M. Sacks and H. Campos. *J Clin Endocrinol Metab.* 2006; Vol. 91, No. 2, pgs 398-400; A. Mishra et al. *Arterioscler Thromb Vasc Biol.* 2004; pgs 1621-1627.). Thus, by selecting the appropriate process conditions, a cross-linked hydrophobic fatty acid-derived biomaterial (from, e.g., fish oil) can be created and controlled using oil oxidation chemistry with a final chemical profile that will have a favorable biological performance in-vivo.

The process of making a fatty acid-derived hydrophobic non-polymeric biomaterial as described in this invention leads to a final chemical profile that is biocompatible, minimizes adhesion formation, acts as a tissue separating barrier, and is non-inflammatory with respect to the material chemistry and the products produced upon hydrolysis and absorption by the body in-vivo. The reason for these properties is due to several unique characteristics of the fatty acid-derived biomaterials (e.g., coatings or stand-alone films) of the invention.

One important aspect of the invention is that no toxic, short-chained cross-linking agents (such as glutaraldehyde) are used to form the fatty acid-derived biomaterials (e.g., coatings or stand-alone films) of the invention. It has been previously demonstrated in the literature that short chain cross-linking agents can elute during hydrolysis of biodegradable polymers and cause local tissue inflammation. The process of creating fatty acid-derived biomaterials does not involve adding external cross-linking agents because the oil is solely cured into a coating using oil autoxidation or photo-oxidation chemistry. The oxidation process results in the formation of carboxyl and hydroxyl functional groups that allow for the fatty acid-derived biomaterial to become hydrated and become slippery, which allows for frictional injury during and after implantation to be significantly reduced and/or eliminated. The methods of making the fatty acid-derived biomaterials described herein allow the alkyl chains of the fatty acid, glyceride and other lipid byproducts present in the coating to be disordered, which creates a coating that is flexible and aids in handling of the material while being implanted.

There are several individual chemical components of the coating that aid in its biocompatibility and its low to non-inflammatory response observed in-vivo. One critical aspect is that the process of creating a fatty acid-derived biomaterial as described herein results in low to non-detectable amounts of oxidized lipid byproducts of biocompatibility concern, such as aldehydes. These products are either almost completely reacted or volatilized during the curing process as described in this invention. The process of creating a fatty acid-derived biomaterial largely preserves the esters of the native oil triglycerides and forms ester and/or lactone cross-links, which are biocompatible (K. Park et al., 1993; J. M. Andersen, 1995).

In addition to general chemical properties of a fatty acid-derived biomaterial that assists in its biocompatibility, there are also specific chemical components that have positive biological properties. Another aspect is that the fatty acid chemistry produced upon creation of a fatty acid-derived biomaterial is similar to the fatty acid chemistry of tissue, as presented in FIG. 7. Thus, as fatty acids are eluting from the coating they are not viewed as being "foreign" by the body and cause an inflammatory response. In fact, C14 (myristic) and C16 (palmitic) fatty acids present in the coating have been shown in the literature to reduce production of $\alpha$-TNF, an inflammatory cytokine. The expression of $\alpha$-TNF has been identified as one of the key cytokines responsible for "turning on" inflammation in the peritoneal after hernia repair, which can then lead to abnormal healing and adhesion formation (Y. C. Cheong et al., 2001). $\alpha$-TNF is also an important cytokine in vascular injury and inflammation (D. E. Drachman and D. I. Simon, 2005; S. E. Goldblum, 1989), such as vascular injury caused during a stent deployment. In addition to the fatty acids just specified, there have also been additional oxidized fatty acids identified that have anti-inflammatory properties. Another component identified from the fatty acid-derived coatings as described in this invention is delta-lactones (i.e., 6-membered ring cyclic esters). Delta-lactones have been identified as having anti-tumor properties (H. Tanaka et al. *Life Sciences* 2007; Vol. 80, pgs 1851-1855).

These components identified are not meant to be limiting in scope to this invention as changes in starting oil composition and/or process conditions can invariably alter the fatty acid and/or oxidative byproduct profiles and can be tailored as needed depending on the intended purpose and site of application of the fatty acid-derived biomaterial.

In summary, the biocompatibility and observed in in-vivo performance of fatty acid-derived biomaterials described in this invention is due to the elution of fatty acids during hydrolysis of the material during implantation and healing and is not only beneficial as to prevent a foreign body response in-vivo due to the similarity of the fatty acid composition of the material to native tissue (i.e., a biological "stealth" coating), but the specific fatty acids and/or other lipid oxidation components eluting from the coating aid in preventing foreign body reactions and reducing or eliminating inflammation, which leads to improved patient outcomes. Additionally, the fatty acid and glyceride components eluted from the fatty acid-derived biomaterial are able to be absorbed by local tissue and metabolized by cells, in, for example, the Citric Acid Cycle (M. J. Campell, "Biochemistry: Second Edition." 1995, pgs 366-389). Hence, the fatty acid-derived biomaterial (e.g., coating or stand-alone film) described in this invention is also bioabsorbable.

Accordingly, in one aspect, the invention provides a bioabsorbable, fatty acid-based coating for a medical device, comprising a cross-linked fatty acid fatty acid-derived biomaterial and a therapeutic agent. The invention also provides a bio-absorbable, fatty acid-based stand-alone film, comprising a cross-linked fatty acid fatty acid-derived biomaterial and a therapeutic agent. The coating and stand-alone film can be prepared according to the methods discussed herein.

Methods of Treatment Using Fatty Acid-Derived Materials

Also provided herein is a fatty acid-based biomaterial suitable for treating or preventing disorders related to vascular injury and/or vascular inflammation. The fatty acid-based biomaterial can also be used to treat or prevent injury to tissue, e.g., soft tissue. The fatty acid-based biomaterial can be a coating for a medical device or a stand-alone film. In another embodiment, the source of the fatty acid for the biomaterial is an oil, such as fish oil.

In general, four types of soft tissue are present in humans: epithelial tissue, e.g., the skin and the lining of the vessels and many organs; connective tissue, e.g., tendons, ligaments, cartilage, fat, blood vessels, and bone; muscle, e.g., skeletal (striated), cardiac, or smooth; and nervous tissue, e.g., brain, spinal chord and nerves. The fatty acid-based biomaterial of the invention (e.g., stand-alone film) can be used to treat injury to these soft tissue areas. Thus, in one embodiment, the fatty acid-based biomaterial of the invention (e.g., stand-alone film) can be used for promotion of proliferation of soft tissue for wound healing. Furthermore, following acute trauma, soft tissue can undergo changes and adaptations as a result of healing and the rehabilitative process. Such changes include, by are not limited to, metaplasia, which is conversion of one kind of tissue into a form that is not normal for that tissue; dysplasia, with is the abnormal development of tissue; hyperplasia, which is excessive proliferation of normal cells in the normal tissue arrangement; and atrophy, which is a decrease in the size of tissue due to cell death and resorption or decreased cell proliferation. Accordingly, the fatty acid-based biomaterial of the invention (e.g., stand-alone film) can be used for the diminishment or alleviation of at least one symptom associated with or caused by acute trauma in soft tissue.

In one embodiment, as described below, the fatty acid-based biomaterial can be used, for example, to prevent tissue adhesion. The tissue adhesion can be a result of blunt dissection. Blunt dissection can be generally described as dissection accomplished by separating tissues along natural cleavage lines without cutting. Blunt dissection is executed using a number of different blunt surgical tools, as is understood by those of ordinary skill in the art. Blunt dissection is often performed in cardiovascular, colo-rectal, urology, gynecology, upper GI, and plastic surgery applications, among others.

After the blunt dissection separates the desired tissues into separate areas, there is often a need to maintain the separation of those tissues. In fact, post surgical adhesions can occur following almost any type of surgery, resulting in serious postoperative complications. The formation of surgical adhesions is a complex inflammatory process in which tissues that normally remain separated in the body come into physical contact with one another and attach to each other as a result of surgical trauma.

It is believed that adhesions are formed when bleeding and leakage of plasma proteins from damaged tissue deposit in the abdominal cavity and form what is called a fibrinous exudate. Fibrin, which restores injured tissues, is sticky, so the fibrinous exudate may attach to adjacent anatomical structures in the abdomen. Post-traumatic or continuous inflammation exaggerates this process, as fibrin deposition is a uniform host response to local inflammation. This attachment seems to be reversible during the first few days after injury because the fibrinous exudates go through enzymatic degradation caused by the release of fibrinolytic factors, most notably tissue-type plasminogen activator (t-PA). There is constant play between t-PA and plasminogen-activator inhibitors. Surgical trauma usually decreases t-PA activity and increases plasminogen-activator inhibitors. When this happens, the fibrin in the fibrinous exudate is replaced by collagen. Blood vessels begin to form, which leads to the development of an adhesion. Once this has occurred, the adhesion is believed to be irreversible. Therefore, the balance between fibrin deposition and degradation during the first few days post-trauma is critical to the development of adhesions (Holmdahl L. *Lancet* 1999; 353: 1456-57). If normal fibrinolytic activity can be maintained or quickly restored, fibrous deposits are lysed and permanent adhesions can be avoided. Adhesions can appear as thin sheets of tissue or as thick fibrous bands.

Often, the inflammatory response is also triggered by a foreign substance in vivo, such as an implanted medical device. The body sees this implant as a foreign substance, and the inflammatory response is a cellular reaction to wall off the foreign material. This inflammation can lead to adhesion formation to the implanted device; therefore a material that causes little to no inflammatory response is desired.

Thus, the fatty acid-based biomaterial (e.g., stand-alone film) of the present invention may be used as a barrier to keep tissues separated to avoid the formation of adhesions, e.g., surgical adhesions. Application examples for adhesion prevention include abdominal surgeries, spinal repair, orthopedic surgeries, tendon and ligament repairs, gynecological and pelvic surgeries, and nerve repair applications. The fatty acid-based biomaterial (e.g., stand-alone film) may be applied over the trauma site or wrapped around the tissue or organ to limit adhesion formation. The addition of therapeutic agents to the fatty acid-based biomaterial used in these adhesion prevention applications can be utilized for additional beneficial effects, such as pain relief or infection minimization. Other surgical applications of the fatty acid-based biomaterial may include using a stand-alone film as a dura patch, buttressing material, internal wound care (such as a graft anastomotic site), and internal drug delivery system. The fatty acid-based biomaterial may also be used in applications in transdermal, wound healing, and non-surgical fields. The fatty acid-based biomaterial may be used in external wound care, such as a treatment for burns or skin ulcers. The fatty acid-based biomaterial may be used without any therapeutic agent as a clean, non-permeable, non-adhesive, non-inflammatory, anti-inflammatory dressing, or the fatty acid-based biomaterial may be used with one or more therapeutic agents for additional beneficial effects. The fatty acid-based biomaterial may also be used as a transdermal drug delivery patch when the fatty acid-based biomaterial is loaded or coated with one or more therapeutic agents.

The process of wound healing involves tissue repair in response to injury and it encompasses many different biologic processes, including epithelial growth and differentiation, fibrous tissue production and function, angiogenesis, and inflammation. Accordingly, the fatty acid-based biomaterial (e.g., stand-alone film) provides an excellent material suitable for wound healing applications.

Modulated Healing

Also provided herein is a fatty acid-based biomaterial suitable for achieving modulated healing in a tissue region in need thereof, wherein the composition is administered in an amount sufficient to achieve said modulated healing. In one embodiment, the fatty acid-based biomaterial is a coating for a medical device or a stand-alone film. In another embodiment, the source of the fatty acid for the biomaterial is an oil, such as fish oil.

Modulated healing can be described as the in-vivo effect observed post-implant in which the biological response is altered resulting in a significant reduction in foreign body response. As utilized herein, the phrase "modulated healing" and variants of this language generally refers to the modulation (e.g., alteration, delay, retardation, reduction, detaining) of a process involving different cascades or sequences of naturally occurring tissue repair in response to localized tissue injury, substantially reducing their inflammatory effect. Modulated healing encompasses many different biologic processes, including epithelial growth, fibrin deposition, platelet activation and attachment, inhibition, proliferation and/or differentiation, connective fibrous tissue production and function, angiogenesis, and several stages of acute and/or chronic inflammation, and their interplay with each other. For example, the fatty acids described herein can alter, delay, retard, reduce, and/or detain one or more of the phases associated with healing of vascular injury caused by medical procedures, including, but not limited to, the inflammatory phase (e.g., platelet or fibrin deposition), and the proliferative phase. In one embodiment, "modulated healing" refers to the ability of a fatty acid derived biomaterial to alter a substantial inflammatory phase (e.g., platelet or fibrin deposition) at the beginning of the tissue healing process. As used herein, the phrase "alter a substantial inflammatory phase" refers to the ability of the fatty acid derived biomaterial to substantially reduce the inflammatory response at an injury site. In such an instance, a minor amount of inflammation may ensue in response to tissue injury, but this level of inflammation response, e.g., platelet and/or fibrin deposition, is substantially reduced when compared to inflammation that takes place in the absence of the fatty acid derived biomaterial.

For example, the fatty acid derived biomaterial (e.g., coating or stand-alone film) of the present invention has been shown experimentally in animal models to delay or alter the inflammatory response associated with vascular injury, as well as excessive formation of connective fibrous tissue following tissue injury. The fatty acid derived biomaterial (e.g., coating or stand-alone film) of the present invention can delay or reduce fibrin deposition and platelet attachment to a blood contact surface following vascular injury.

Accordingly, the fatty acid derived biomaterial (e.g., coating or stand-alone film) of the present invention provides an excellent absorbable cellular interface suitable for use with a surgical instrument or medical device that results in a modulated healing effect, avoiding the generation of scar tissue and promoting the formation of healthy tissue at a modulated or delayed period in time following the injury. Without being bound by theory, this modulated healing effect can be attributed to the modulation (e.g., alteration, delay, retardation, reduction, detaining) of any of the molecular processes associated with the healing processes of vascular injury. For example, the fatty acid derived biomaterial (e.g., coating or stand-alone film) of the present invention can act as a barrier or blocking layer between a medical device implant (e.g., a surgical mesh, graft, or stent), or surgical instrument, and the cells and proteins that compose the vessel wall, such as the endothelial cells and smooth muscle cells that line the vessel's interior surface. The barrier layer prevents the interaction between the surgical implant and the vessel surface, thereby preventing the initiation of the healing process by the cells and proteins of the vessel wall. In this respect, the barrier layer acts as a patch that binds to the vessel wall and blocks cells and proteins of the vessel wall from recognizing the surgical implant (i.e., the barrier layer blocks cell-device and/or protein-device interactions), thereby blocking the initiation of the vascular healing process, and avoiding the fibrin activation and deposition and platelet activation and deposition.

In another non-binding example, the modulated healing effect can be attributed to the modulation (e.g., alteration, delay, retardation, reduction, detaining) of signaling between the cells and proteins that compose the vessel wall and various components of the bloodstream that would otherwise initiate the vascular healing process. Stated differently, at the site of vascular injury, the fatty acid derived biomaterial (e.g., coating or stand-alone film) of the present invention can modulate the interaction of cells of the vessel wall, such as endothelial cells and/or smooth muscle cells, with other cells and/or proteins of the blood that would otherwise interact with the damaged cells to initiate the healing process. Additionally, at the site of vascular injury, the fatty acid derived biomaterial (e.g., coating or stand-alone film) of the present invention can modulate the interaction of proteins of the vessel wall with other cells and/or proteins of the blood, thereby modulating the healing process.

The fatty acid derived biomaterial (e.g., coating or stand-alone film) of the present invention can be designed to maintain its integrity for a desired period of time, and then begin to hydrolyze and be absorbed into the tissue that it is surrounded by. Alternatively, the fatty acid derived biomaterial can be designed such that, to some degree, it is absorbed into surrounding tissue immediately after the fatty acid derived biomaterial is inserted in the subject. Depending on the formulation of the fatty acid derived biomaterial, it can be completely absorbed into surrounding tissue within a time period of 1 day to 24 months, e.g., 1 week to 12 months, e.g., 1 month to 10 months, e.g., 3 months to 6 months. Animal studies have shown resorption of the fatty acid derived biomaterial occurring upon implantation and continuing over a 3 to 6 month period, and beyond.

Tailoring of Drug Release Profiles

In various aspects, the present invention provides methods of curing a fatty acid-derived coating, preferably fish oil, to provide a fatty acid-derived biomaterial coating or stand-alone film containing one or more therapeutic agents that can tailor the release profile of a therapeutic agent from the coating or film. The release profile can be tailored, e.g., through changes in fatty acid (e.g., oil, e.g., fish oil) chemistry by varying coating composition, temperature, and cure times. The position of the drug-containing layer on the coated device provides an additional mechanism to alter the release profile of the non-polymeric cross-linked fatty acid-derived biomaterial coating. This can be achieved, e.g., by loading a drug into a cured base coating layer and coating a topcoat overlayer cured coating onto the previously cured encapsulating base layer.

An advantage of the cured fish oil coating and stand-alone film in various embodiments of the present invention is that the curing conditions utilized (i.e., cure time and temperature) can directly influence the amount of coating cross-linking density and byproduct formation, which in turn effects the coating degradation. Thus, by altering the curing conditions employed, the dissolution rate of a therapeutic compound of interest contained in the coating can also be altered.

In various embodiments, an agent, such as, e.g., a free radical scavenger, can be added to the starting material to tailor the drug release profile of the fatty acid-derived biomaterial that is formed. In various embodiments, vitamin E is added to the starting material to, for example, slow down autoxidation in fish oil by reducing hydroperoxide formation, which can result in a decrease in the amount of cross-linking observed in a cured fish oil coating. In addition, other agents can be used to increase the solubility of a therapeutic agent in the oil component of the starting material, protect the drug from degradation during the curing process, or both. For example, vitamin E can also be used to increase the solubility of certain drugs in a fish oil starting material, and thereby facilitate tailoring the drug load of the eventual cured coating. Thus, varying the amount of vitamin E present in the coating provides an additional mechanism to alter the cross-linking and chemical composition of the fatty acid-derived biomaterials (e.g., coatings and stand-alone films) of the present invention.

In various embodiments, the present invention provides fatty acid-derived biomaterials (e.g., coatings and stand-alone films) where the drug release profile of the fatty acid-derived biomaterial is tailored through the provision of two or more coatings and selection of the location of the therapeutic agent. The drug location can be altered, e.g., by coating a bare portion of a medical device with a first starting material and creating a first cured coating, then coating at least a portion of the first cured-coating with the drug-oil formulation to create a second overlayer coating. The first starting material can contain one or more therapeutic agents. In various embodiments, the second overlayer coating is also cured. The drug load, drug release profiles, or both, of the first coating, the overlay coating, or both, can be tailored through the use of different curing conditions and/or addition of free radical scavengers (e.g., vitamin E), as described herein. The process of providing two layers can be extended to provide three or more layers, wherein at least one of the layers comprises a hydrophobic, cross-linked fatty acid-derived biomaterial prepared from a fatty-acid containing oil, such as fish oil. In addition, one or more of the layers can be drug eluting, and the drug release profile of such layers can be tailored using the methods described herein.

In various embodiments, the present invention provides coatings where the drug release profile of the overall coating is tailored through the provision of two or more coating regions with different drug release profiles and selection of the location of the therapeutic agent. In various embodiments, the formation of different coating regions with different drug release properties is obtained by location specific curing conditions, e.g., location specific UV irradiation, and/or location specific deposition of a starting material on the coated device, e.g., by ink jet printing methods.

Coating Approaches

FIG. 8 illustrates one method of making a medical device, such as, e.g., a drug eluting coated stent, in accordance with one embodiment of the present invention. The process involves providing a medical device, such as the stent (step 100). A non-polymeric cross-linked fatty acid-derived biomaterial coating is then applied to the medical device (step 102). One of ordinary skill in the art will appreciate that this basic method of application of a coating to a medical device, such as a stent, can have a number of different variations falling within the process described. The step of applying a coating substance to form a coating on the medical device can include a number of different application methods. For example, the medical device can be dipped into a liquid solution of the coating substance. The coating substance can be sprayed onto the device. Another application method is painting the coating substance on to the medical device. One of ordinary skill in the art will appreciate that other methods, such as electrostatic adhesion, can be utilized to apply the coating substance to the medical device. Some application methods may be particular to the coating substance and/or to the structure of the medical device receiving the coating. Accordingly, the present invention is not limited to the specific embodiments of starting material application described herein, but is intended to apply generally to the application of the starting material which is to become a fatty acid-derived biomaterial coating of a medical device, taking whatever precautions are necessary to make the resulting coating maintain desired characteristics.

FIG. 9 is a flowchart illustrating one example implementation of the method of FIG. 8. In accordance with the steps illustrated in FIG. 9, a bio-absorbable carrier component formed from or of the non-polymeric fatty acid-derived biomaterial of the present invention is provided along with a therapeutic agent component (step 110). The provision of the bio-absorbable carrier component and the provision of the therapeutic agent component can occur individually, or in combination, and can occur in any order or simultaneously. The bio-absorbable carrier component is mixed with the therapeutic agent component (or vice versa) to form a starting material which is to become a hydrophobic, fatty acid-derived biomaterial coating (step 112). The starting material is applied to the medical device, such as the stent 10, to form the coating (step 114). The coating is then cured (step 116) by any of the curing methods described herein to form a fatty acid-derived biomaterial coating.

The coated medical device is then sterilized using any number of different sterilization processes (step 118). For example, sterilization can be implemented utilizing ethylene oxide, gamma radiation, E beam, steam, gas plasma, or vaporized hydrogen peroxide. One of ordinary skill in the art will appreciate that other sterilization processes can also be applied, and that those listed herein are merely examples of sterilization processes that result in a sterilization of the coated stent, preferably without having a detrimental effect on the coating.

It should be noted that the oil component or oil composition can be added multiple times to create multiple tiers in forming the coating. For example, if a thicker coating is desired, additional tiers of the oil component or oil composition can be added. Different variations relating to when the oil is cured and when other substances are added to the oil are possible in a number of different process configurations. Accordingly, the present invention is not limited to the specific sequence illustrated. Rather, different combinations of the basic steps illustrated are anticipated by the present invention.

Figure 10A:
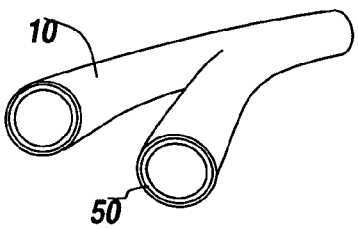
FIGS. 10A-10E are various images of coated medical devices.
Figure 10B:
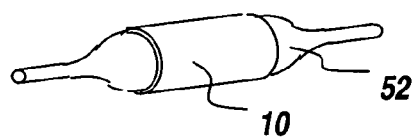
Figure 10C:
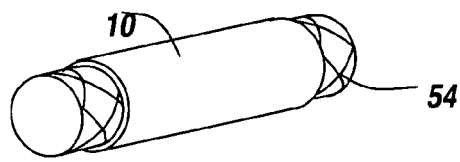
Figure 10D:
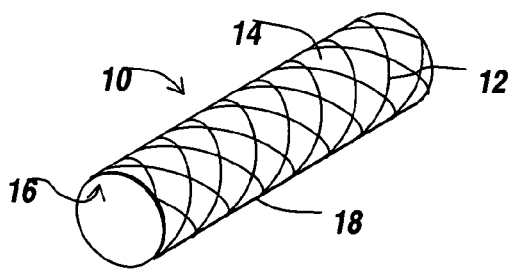

FIGS. 10A-10E illustrate some of the other forms of medical devices mentioned above in combination with the coating 10 of the present invention. FIG. 10A shows a graft 50 with the coating 10 coupled or adhered thereto. FIG. 10B shows a catheter balloon 52 with the coating 10 coupled or adhered thereto. FIG. 10C shows a stent 54 with the coating 10 coupled or adhered thereto. FIG. 10D illustrates a stent 10 in accordance with one embodiment of the present invention.

Figure 10E:
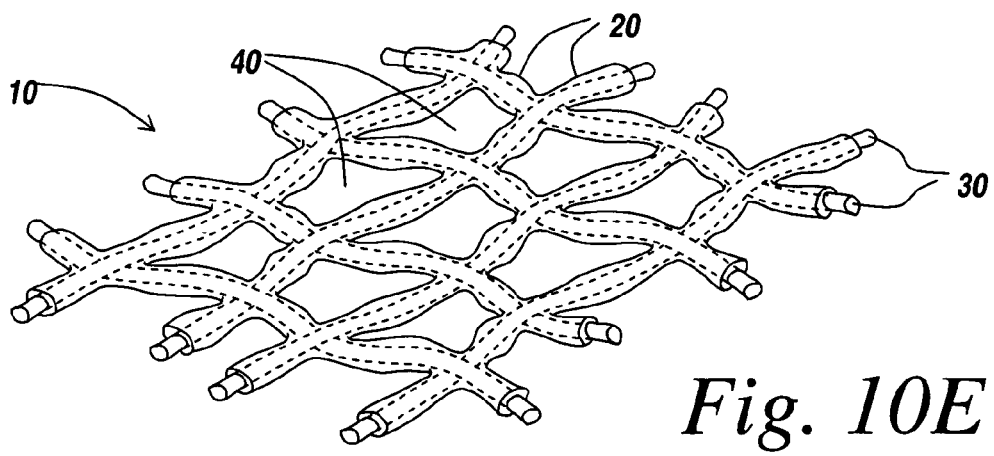

The stent 10 is representative of a medical device that is suitable for having a coating applied thereon to effect a therapeutic result. The stent 10 is formed of a series of interconnected struts 12 having gaps 14 formed therebetween. The stent 10 is generally cylindrically shaped. Accordingly, the stent 10 maintains an interior surface 16 and an exterior surface 18. FIG. 10E illustrates a coated surgical mesh, represented as a biocompatible mesh structure 10, in accordance with one embodiment of the present invention. The biocompatible mesh structure 10 is flexible, to the extent that it can be placed in a flat, curved, or rolled configuration within a patient. The biocompatible mesh structure 10 is implantable, for both short term and long term applications. Depending on the particular formulation of the biocompatible mesh structure 10, the biocompatible mesh structure 10 will be present after implantation for a period of hours to days, or possibly months, or permanently.

Each of the medical devices illustrated, in addition to others not specifically illustrated or discussed, can be combined with the coating 10 using the methods described herein, or variations thereof. Accordingly, the present invention is not limited to the example embodiments illustrated. Rather the embodiments illustrated are merely example implementations of the present invention.

Various aspects and embodiments are further described by way of the following Examples. The Examples are offered by way of illustration and not by way of limitation.

EXAMPLES

The following examples characterize the hydrophobic cross-linked fatty acid-derived biomaterial chemistry described in this invention and illustrate some of the boundaries associated with the chemical mechanisms of formation and how alteration of those mechanisms influences the properties (e.g., therapeutic benefits and/or drug release profile) of the final product. The identity of some of the hydrolysis products are identified through in-vitro experiments and correlated with in-vivo experiments to demonstrate the ability for the coating or stand-alone film to be bioabsorbed. Finally, examples showing the utility of the fatty acid-derived biomaterials described in this invention in drug delivery applications on coronary stents and hernia mesh devices are presented.

The following examples are for demonstration purposes and are not meant to be limiting.

Example 1

Characterization of a Novel Biomaterial Derived from Fish Oil

In this example, coated medical devices (e.g., a polypropylene mesh) were cured in a high airflow oven at 200° F. for 24 hours, after which the fish oil was converted into a cross-linked biomaterial coating encapsulating the polypropylene mesh by oxidation of the C=C bonds present in the fish oil resulting in the formation of oxidative byproducts (i.e., hydrocarbons, aldehydes, ketones, glycerides, fatty acids) while largely preserving the esters derived from the original oil triglycerides. Volatilization of the byproducts followed by the formation of ester and lactone cross-links result in the solidification of oil into a bioabsorbable hydrophobic cross-linked fatty acid-derived biomaterial. FTIR, X-ray diffraction, and GC-FID fatty acid compositional analysis and GC-MS were performed on the fish oil derived coatings to characterize its chemistry.

Figure 11:
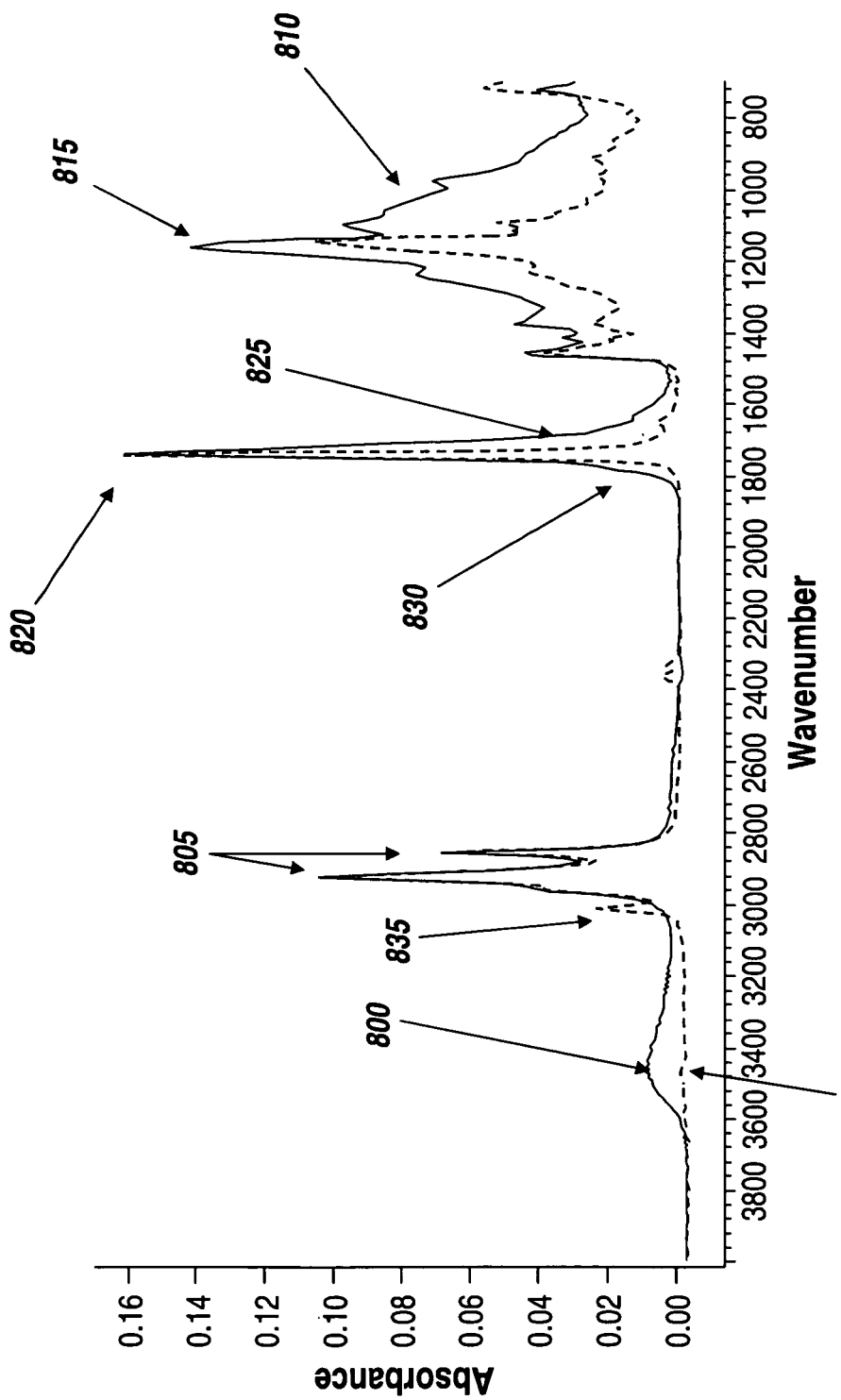
FIG. 11 depicts an FTIR analysis of the final cured coating after heating at 200° F. for 24 hr (Example 1)

FTIR Analysis:

FIG. 11 is an FTIR analysis, which illustrates a comparison of the uncured fish oil (801) with the final cured fatty acid-derived biomaterial. The FTIR shows that the coating contained hydroxyl (800), methylene (805), trans C=C (810), and lactone/ester bonds (815 and 830). A complex carbonyl band shape was obtained and determined to contain ester (820), ketone (825), aldehyde (825), and fatty acid (825) absorptions in addition to detecting the presence of cross-linking (830). Although several different types of ester cross-linking are possible (e.g, anhydride, lactone, aliphatic peroxide, etc.) the broadness of the lactone/band suggests a combination of lactone (cyclic ester) and ester (R—C=C—O—CO-Alkyl) functional groups predominate since there is a single cross-linking peak absorption from 1740-1840 cm$^{-1}$. In contrast, anhydride (CO—O—CO) and aliphatic peroxides (CO—O—O—CO) both have two carbonyls and would be expected to have two peaks with absorptions around approximately 1850-1800 and 1790-1740 cm$^{-1}$. Additionally, evaluation of the fish oil and fatty acid-derived biomaterial ester (820) absorption bands show that there is not a significant reduction in ester band height after curing, indicating that the original triglyceride ester groups are largely preserved through the curing process. The position of the methylene bands showed that the hydrocarbon chains present in the coating were in a disordered state (position above about 2918 cm$^{-1}$), which is consistent with a non-crystalline structure. This result was also confirmed by X-ray diffraction results which showed that the fatty acid-derived biomaterial coating is amorphorous (i.e., disordered). Further, the cis C=C bonds in the fish oil starting material (835) were observed to be almost entirely consumed during the curing process. There was an increase in the trans C=C bonds (810) during the curing process, but is reduced in peak area in comparison to the original cis C=C band, which is consistent with the oxidation of the C=C bonds in the oil during the curing process.

Figure 12A:
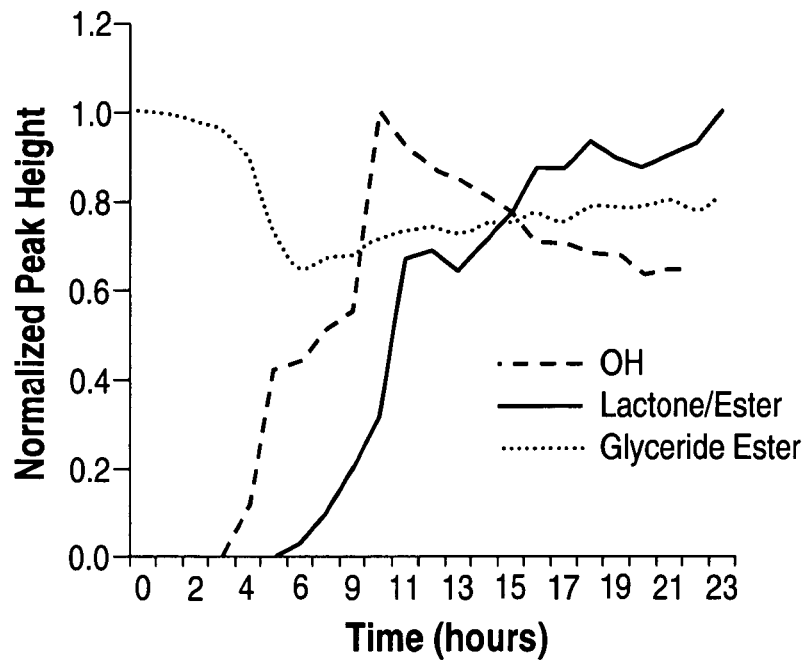
FIGS. 12A-12B depict analysis of FTIR data discussed in Example 1.
Figure 12B:
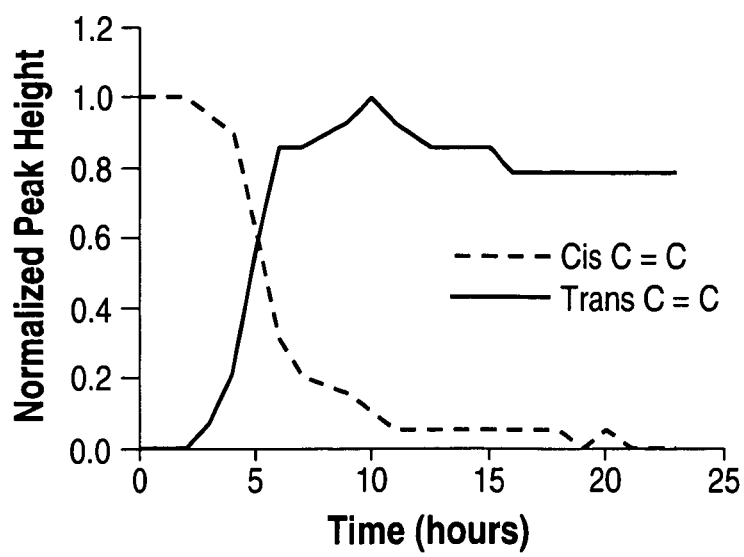

FTIR spectra were also acquired kinetically during the curing process using a procedure described in the literature (see, e.g., Van de Voort et al. (1994) *JAOCS*, vol 70, no. 3, pgs 243-253, the entire contents of which is hereby incorporated by reference) to monitor changes in the chemistry of the coating during the curing of the fatty acid-derived biomaterial using normalized peak height ratios. FIG. 12A compares the change in the normalized peak height of the OH, glyceride ester, and lactone/ester as a function of temperature. The data in FIG. 12A shows a sharp increase in the OH band up to hour 11, after which the OH band dramatically decreases through the rest of the curing process. This correlates with the increase in the lactone/ester cross-linking band which also dramatically increases around hours 10-11, at which point the coating is observed to physically convert into a gel. Additionally at this same time interval, the C=C bonds have isomerized from a cis to trans configuration, which would assist in facilitating the formation of ester and lactone linkages (i.e., esterification between hydroxyl and carboxyl functional groups in oxidized fatty acids and glycerides present in the oil (FIG. 12B)). Also, after hour 11 the trans C=C bond decreases as the curing process continues, which indicates that the C=C bonds are being oxidized. By the end of the curing process the trans C=C band is approximately half of the peak area of original cis C=C bonds. Finally, using the subtraction technique mentioned by Van de Voort et al. it is possible to resolve a small amount of thermal hydrolysis in the native glyceride band, followed by esterification during the curing reaction using normalized peak height measurements (FIG. 12A). However, as mentioned previously, the overall peak height in the glyceride peak height before and after curing without subtraction and normalization remains largely unchanged (FIG. 11).

Figure 13:
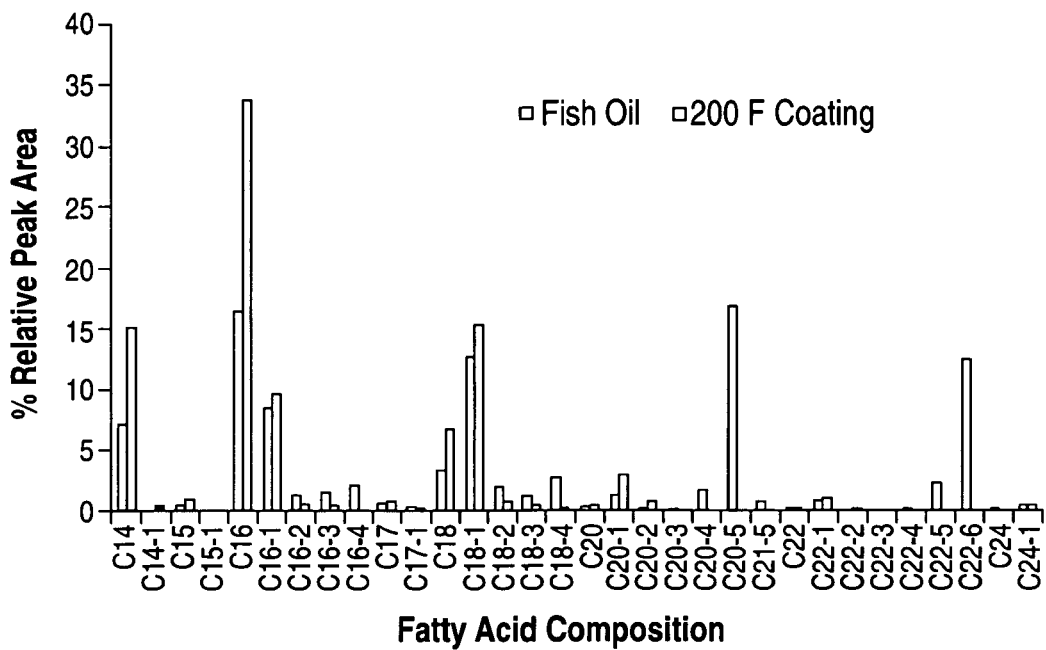
FIG. 13 depicts the GC-FID fatty acid profile data discussed in Example 1.

GC-FID Fatty Acid Compositional Analysis:

GC fatty acid profile analysis was conducted on the fish oil and a fish fatty acid-derived biomaterial using the official AOCS method Ce 1b-89, as presented in FIG. 13. It is important to note that the fatty acid-derived biomaterial coating completely saponified using the conditions outlined in the AOCS procedure. The GC fatty acid profile data proves that the C=C bonds of the fatty acids present in the biomaterial are oxidized and cleaved during the curing process as the polyunsaturated fatty acids are significantly reduced and only monounsaturated and saturated fatty acids are detected. The longer polyunsatured fatty acids (above C20-1 (i.e., twenty carbons, one double bond)) are significantly reduced to non-detected after the curing process. This contrasts a hydrogenation process where C=C bonds are converted into $CH_2$—$CH_2$ functional groups without any reduction in the chain length of the fatty acids present (i.e., C20-5 would become C20-0 with a similar peak area %).

Figure 14:
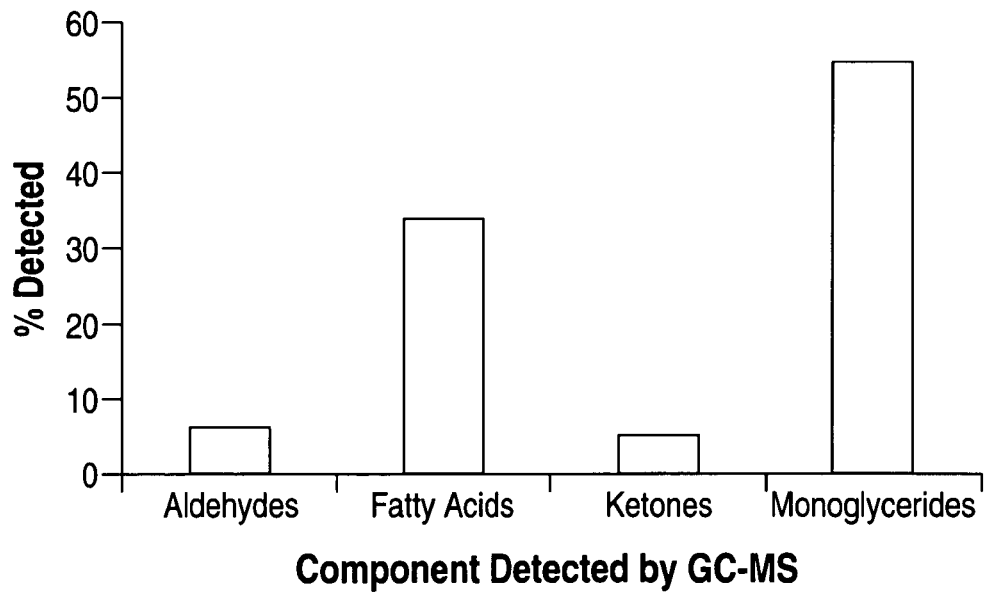
FIG. 14 depicts the GC-MS lipid oxidation byproduct analysis discussed in Example 1.

GC-MS Compositional Analysis:

GC-MS compositional analysis was conducted on the fatty acid derived (from fish oil) biomaterial. The biomaterial was dissolved in THF at 65° C. and the soluble component was filtered away from the insoluble component. Using this process it was determined that 68% of the coating was insoluble in THF and composed of cross-linked fatty acid and glycerides. The other 32% (soluble portion) of the coating was assayed using GC-MS and the identity and amount of different byproducts were determined, as presented in FIG. 14. The GC-MS showed that over 90% of the THF soluble components detected and identified were fatty acids and glycerides where only ~5% of the byproducts were identified as individually being either aldehydes or ketones. Finally, in a separate experiment, GC-MS analysis was conducted using hexane extraction for 24 hours at 37° C. In addition to the products already identified in FIG. 14, approximately 150-300 ppm of 3 different delta-lactones were also detected.

Example 2

Characterization of Novel Biomaterials Derived from Other Oil Starting Materials In Example 2, separate coated medical devices were cured in a high airflow oven at 200° F. for 24 hours, using flax seed, fish, grape seed, or olive oils as the starting material in order to determine the effects of initial fatty acid starting chemistry on the ability to form a non-polymeric, fatty acid-derived hydrophobic biomaterial coating by the oxidative cross-linking mechanisms described in Example 1. After the curing process, the physical properties of each fatty acid-derived coating were noted in addition to being analyzed using FTIR, GC-FID fatty acid profile, and GC-FID aldehyde assay testing.

Physical Properties:

Table 2 presents a summary of the physical properties observed in each oil coating after curing at 200° F. for 24 hours.

TABLE 2

| Oil Coating | Physical Properties |
| --- | --- |
| Olive Oil | Liquid |
| Grape seed Oil | Slightly sticky |
| Flax seed Oil | Dry coating |
| Fish Oil | Dry coating |

Figure 15:
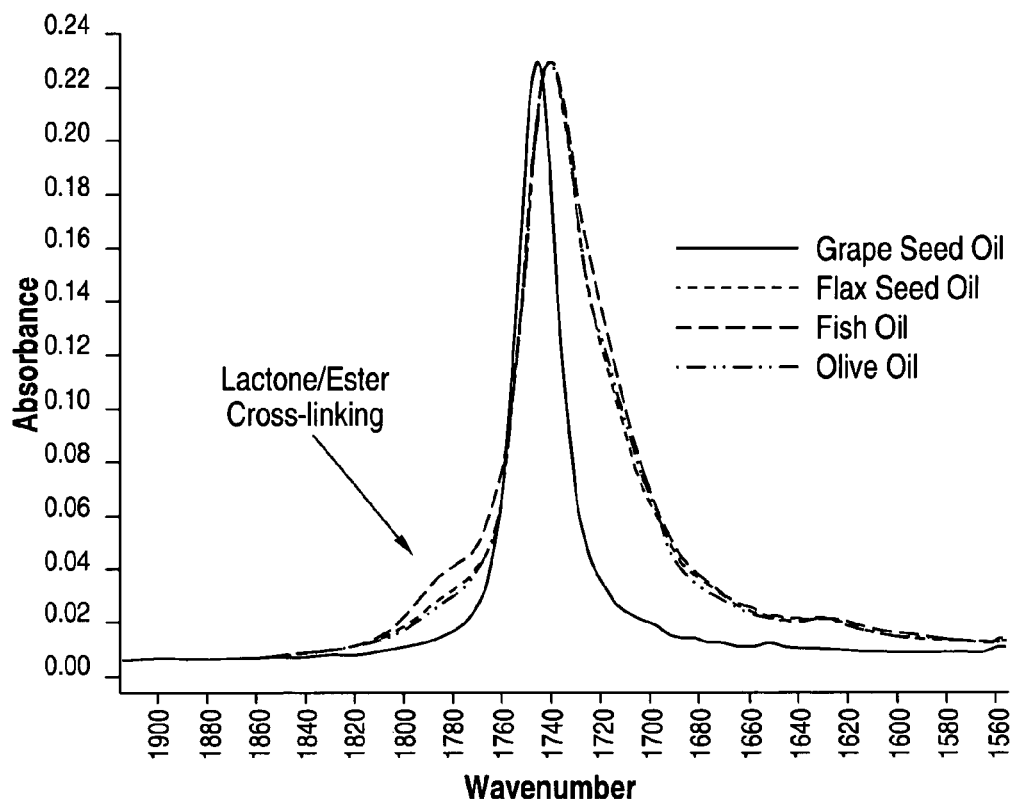
FIG. 15 depicts the FTIR analysis of different oil starting materials after curing into a fatty acid-derived biomaterial as described in Example 2.
Figure 16:
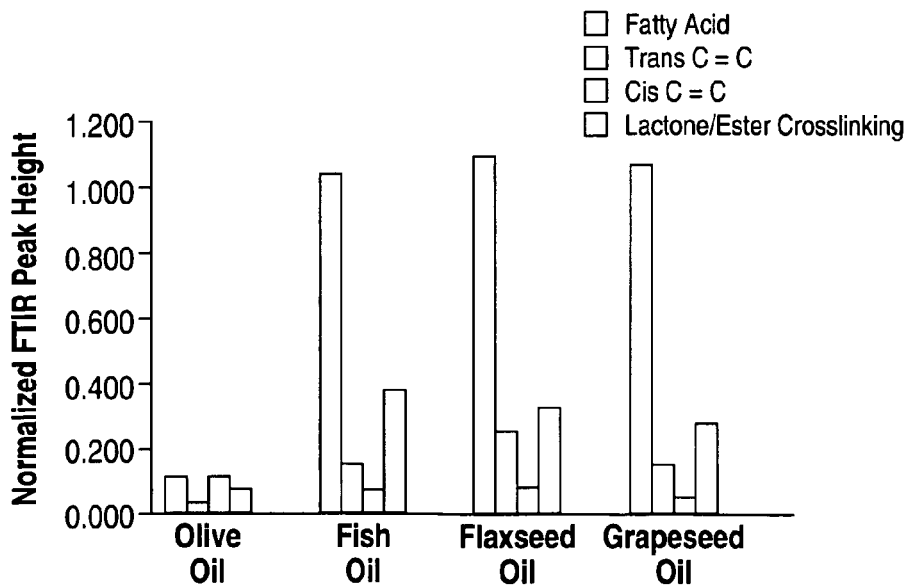
FIG. 16 graphically depicts the differences in chemistry as determined by FTIR analysis of different oil starting materials after curing into a fatty acid-derived biomaterial as described in Example 2.

FTIR Analysis:

FIG. 15 shows the FTIR spectra of the carbonyl absorption region after the 200° F. curing process for the olive, flax seed, grape seed and fish fatty acid-derived biomaterials. The FTIR spectra of the carbonyl band region correlate with the physical properties observed in Table 2. The olive oil, which is liquid, does not show any detectable amount of lactone/ester cross-linking from 1755-1840 $cm^{-1}$. This contrasts the other oils which show varying amounts of cross-linking, with fish oil having the most cross-linking under the conditions employed. FIG. 16 shows a plot of normalized peak ratios for cis and trans C=C, lactone/ester cross-linking, and fatty acid byproducts from the FTIR spectra presented in FIG. 15. The data in FIG. 16 shows that using different starting oils with the same curing process, the final chemistry of the products can be altered, however, for olive oil, which does not make a cured fatty acid-derived biomaterial coating under these process conditions, the peak ratios are significantly different in comparison to the fish, flaxseed, and grape seed oil biomaterial coatings.

Figure 17A:
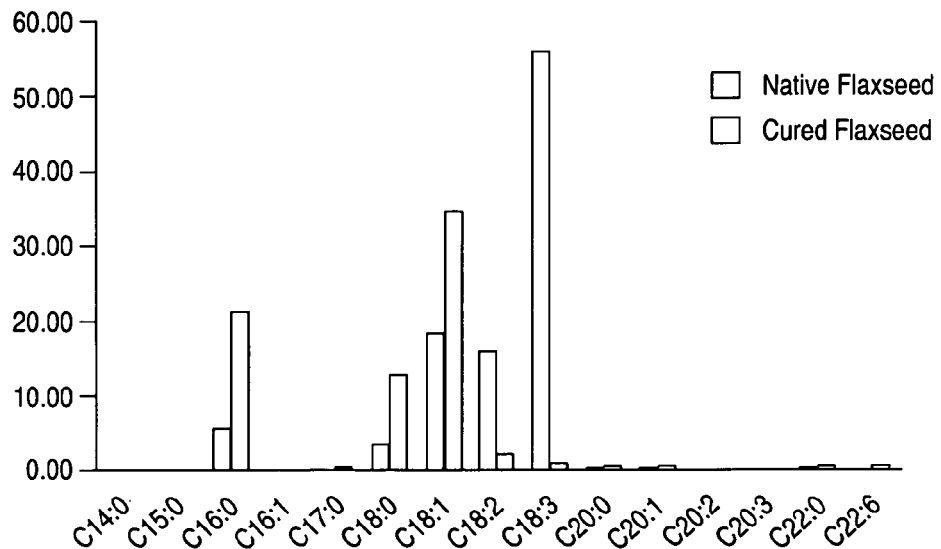
FIGS. 17A, 17B, 18A and 18B show the GC-FID fatty acid profile data of different oil starting materials before and after curing into a fatty acid-derived biomaterial as described in Example 2.
Figure 17B:
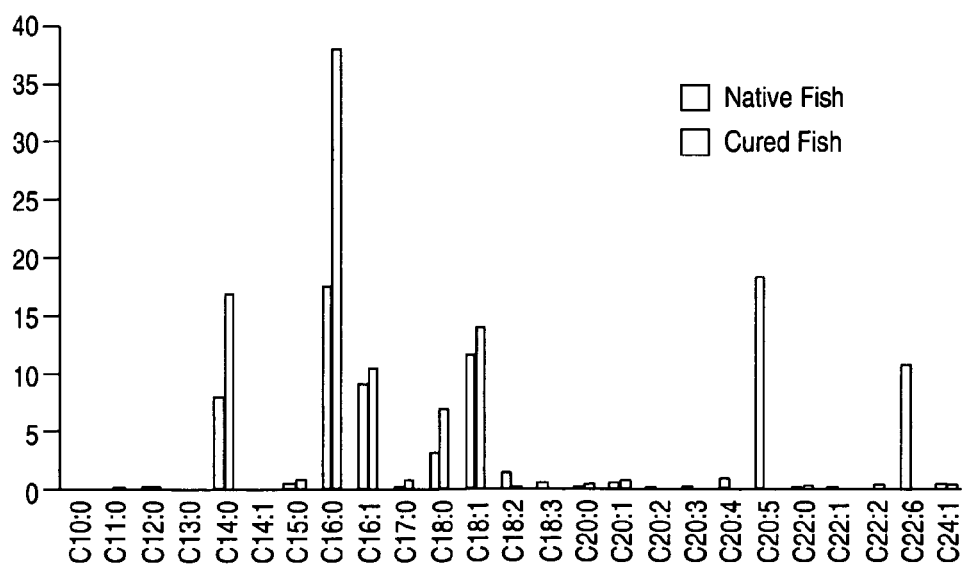
Figure 18A:
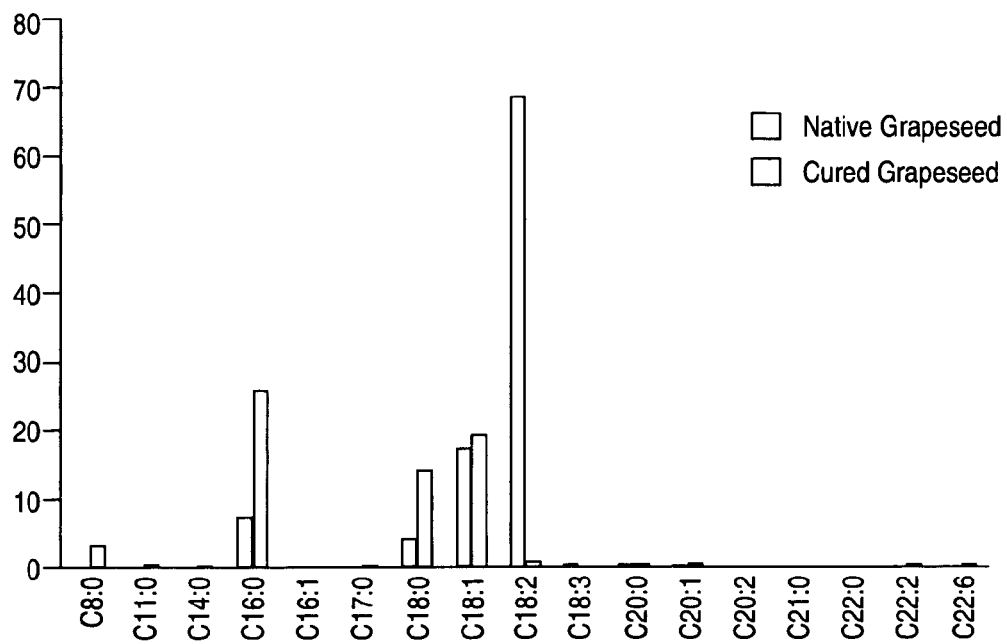
Figure 18B:
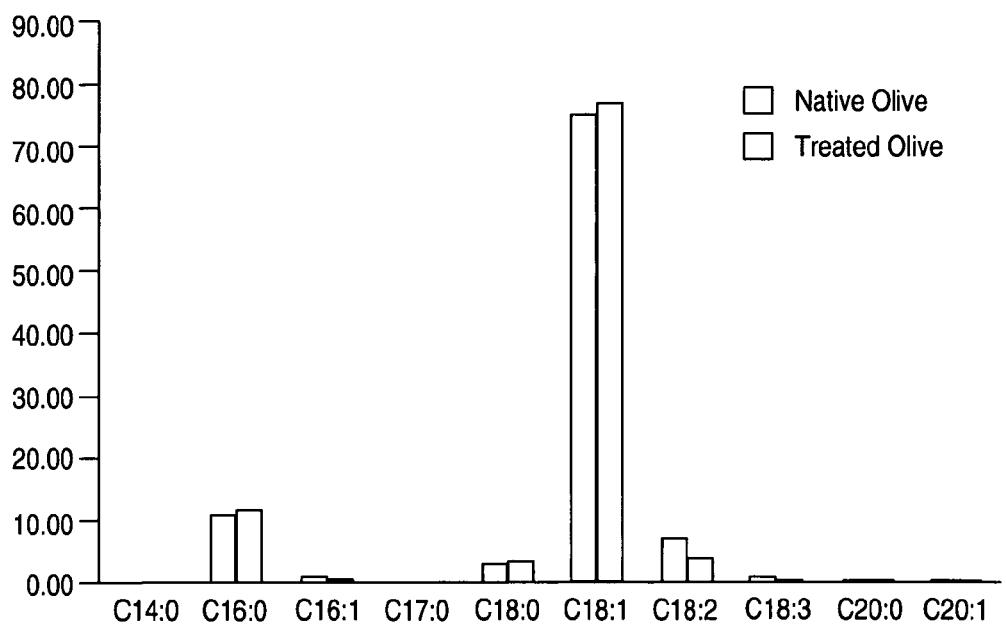

GC-FID Fatty Acid Compositional Analysis:

GC fatty acid profile analysis was conducted on the fish oil and fish fatty acid-derived hydrophobic cross-linked gel using the official AOCS method Ce 1-89b, as presented in FIGS. 17-18. For the grape seed, fish, and flax seed oils a significant difference in fatty acid composition before and after curing is observed. Specifically, the long chain polyunsaturated fatty acids are oxidized during the curing process where only predominantly saturated and unsaturated fatty acids are detected (FIGS. 17 and 18A). In contrast, for the olive oil (FIG. 18B) there is very little relative change in the initial and final fatty acid compositional analysis. The difference in the starting fatty acid composition between the olive oil and the rest of the oils is the starting polyunsaturated fatty acid composition. Olive oil only has only 9% polyunsaturated fatty acids where all the rest of the oils have at least 40% or greater.

GC-FID Aldehyde Assay Analysis:

GC aldehyde assay was performed on each biomaterial coating by extracting the sample in hexane for either 1 hr or 24 hrs at 37° C. and injecting the liquid solution neat into the GC. The aldehydes were quantified using an external standard curve. Previous GC-MS experiments allowed for the aldehyde identities to be determined in order to select the appropriate external standards to be used for quantification. Initial testing involved extracting the fish oil derived biomaterial in hexane for 1 hr and dilution of olive oil in hexane since it remained liquid after cure. The results of this extraction experiment showed that aldehydes could easily be quantified from the olive oil sample, but could not be detected from the fish oil coating after only 1 hr of extraction in hexane. Exhaustive extraction in hexane of the fish oil, grape seed, and flax seed oils was performed for 24 hours at 37° C. The total amount of aldehydes for the fish, grape seed, and flax seed oils were over an order of magnitude less than was detected in the olive oil.

TABLE 3

Aldehyde Assay Results from Different Oil Derived
Biomaterials after Extraction in Hexane for 1 hr.

| Oil Coating | Total Aldehyde Amounts |
|---|---|
| Olive Oil | 3481 ppm |
| Fish Oil | Non-detectable (i.e. <1 ppm) |

TABLE 4

Aldehyde Assay Results from Different Oil Derived
Biomaterials after Exhaustive Extraction on Hexane for 24 hrs.

| Oil Coating | Total Aldehyde Amounts |
|---|---|
| Grape Seed Oil | 151 ppm |
| Flax Seed Oil | 228 ppm |
| Fish Oil | 254 ppm |

Fatty Acid Ranges for Various Oils:

Flax seed, grape seed, and fish fatty acid-derived biomaterials were prepared in accordance with the procedures of this example. GC fatty acid profile analysis showed the following fatty acid ranges:

| Flax seed fatty acid-derived biomaterial | |
|---|---|
| C16:0 | 5-30% |
| C18:0 | 0-15% |
| C18:1 | 15-40% |
| C18:2 | 0-20% |
| C18:3 | 0-60% |
| Grape seed fatty acid-derived biomaterial | |
| C16:0 | 5-30% |
| C18:0 | 0-20% |
| C18:1 | 15-30% |
| C18:2 | 0-75% |
| Fish fatty acid-derived biomaterial | |
| C14:0 | 5-25% |
| C16:0 | 5-50% |
| C16:1 | 5-15% |
| C18:0 | 0-10% |
| C18:1 | 5-20% |
| C18:2 | 0-5% |
| C18:3 | 0-5% |
| C20:1 | 0-5% |
| C20:4 | 0-5% |
| C20:5 | 0-40% |
| C22:6 | 0-30% |
| C24:1 | 0-2% |

Conclusions:

This set of experiments showed that, in order to create a fatty acid derived biomaterial (e.g., coating or stand-alone film), an oil source needs to not only contain unsaturated fatty acids, but specifically polyunsaturated fatty acids in order to form the novel fatty acid-derived biomaterial described in this invention. Also, the resultant coating forms a cross-linked matrix that contains a very low amount of residual aldehydes from the curing process that cannot be detected unless harsh extraction conditions in an organic solvent are employed.

Example 3

In-Vitro Hydration Ability of a Novel Biomaterial Derived from Fish Oil

The following example characterizes the ability of the novel fatty acid-based hydrophobic cross-linked biomaterial to be hydrated and hydrolyzed, and to identify the chemical structure of the elution components released from the material from in-vitro and in-vivo experiments.

Coated medical devices were cured in a high airflow oven at 200° F. for 24 hours, after which the fish oil was converted into a fatty acid derived biomaterial coating encapsulating the polypropylene mesh by oxidation of the C=C bonds present in the fish oil resulting in the formation of oxidative byproducts (i.e., hydrocarbons, aldehydes, ketones, glycerides, fatty acids) while largely preserving the esters derived from the original oil triglycerides. Volatilization of the byproducts followed by the formation of ester and lactone cross-links result in the solidification of oil into a bioabsorbable hydrophobic cross-linked biomaterial. FTIR and contact angle measurements were performed in order to determine the rate at which the fatty acid-derived biomaterial hydrated at 37° C. in 0.1 M PBS.

Contact angle measurements are taken by adding a drop of water to the surface of a biomaterial in order to determine the hydrophobic/hydrophilic properties of the surface. The contact angle on each side of the water droplet is measured in order to determine the ability for the water droplet to spread (or "wet") across the surface. High contact angles (>80 degrees) indicates a hydrophobic surface. For example PTFE, a hydrophobic material, typically presents contact angle measurements from 110-120 degrees. In contrast, low contact angles, indicate a hydrophilic surface (S. W. Jordan et al. *Biomaterials.* 2006, Vol. 27, pgs 3473-3481). Phospholipids, such as those found on the outside surface of cellular membranes, have contact angles from 40-60 degrees (S. W. Jordan et al, 2006).

Figure 19:
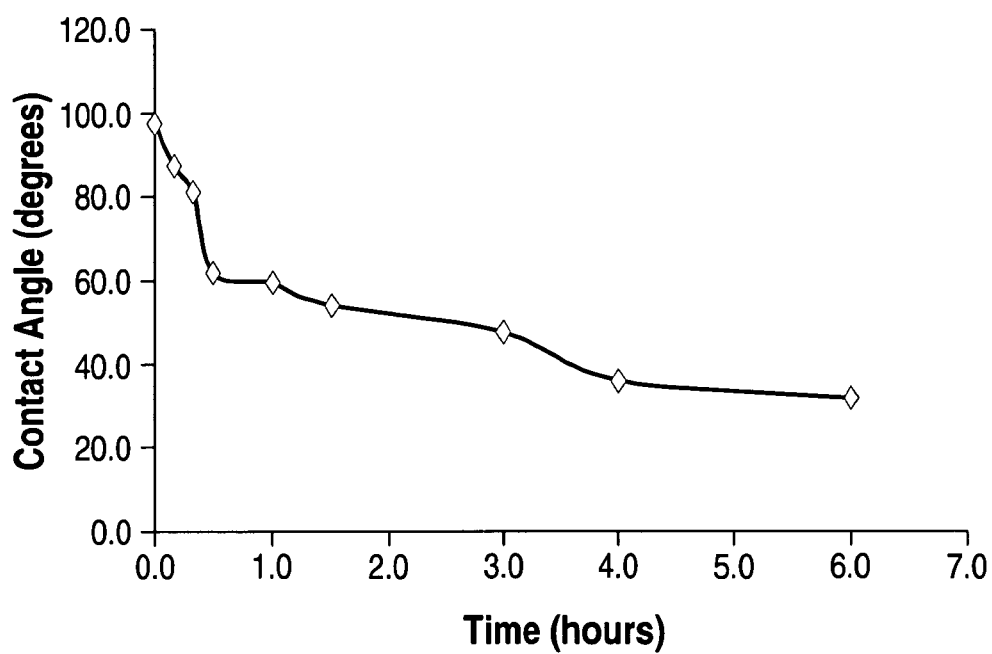
FIG. 19 illustrates the change in contact angle as a function of hydration time for a fatty acid-derived biomaterial described in Example 3.

FIG. 19 presents the contact angle measurements that were performed on the fish oil derived biomaterial as a function of time. Initially, contact angles obtained from the fish fatty acid-derived biomaterial were 100 degrees, which is indication a hydrophobic surface. However, less than 1 hour after exposure to the 0.1 M PBS solution the coating rapidly hydrated and a contact angle of 60 degrees was obtained, indicating that a hydrophilic surface was produced. Physically, the fish fatty acid-derived biomaterial swelled and became slippery, but not sticky, and remained physically intact. After 6 hours of exposure to 0.1 M PBS the coating contact angle plateaued at approximately 32 degrees. Physically the coating continued to exhibit a slippery, but not sticky surface and remain physically intact. The ability for the coating to hydrate and remain physically intact allows for improved handling and placement during surgical implantation and minimizes frictional injury to the patient, such as during a hernia repair or during a coronary stent implantation. Frictional injury caused by the placement of a medical device can lead to inflammation, which can result in clinical complications such as adhesion formation in hernia repair and restenosis in coronary stent deployment.

Figure 20A:
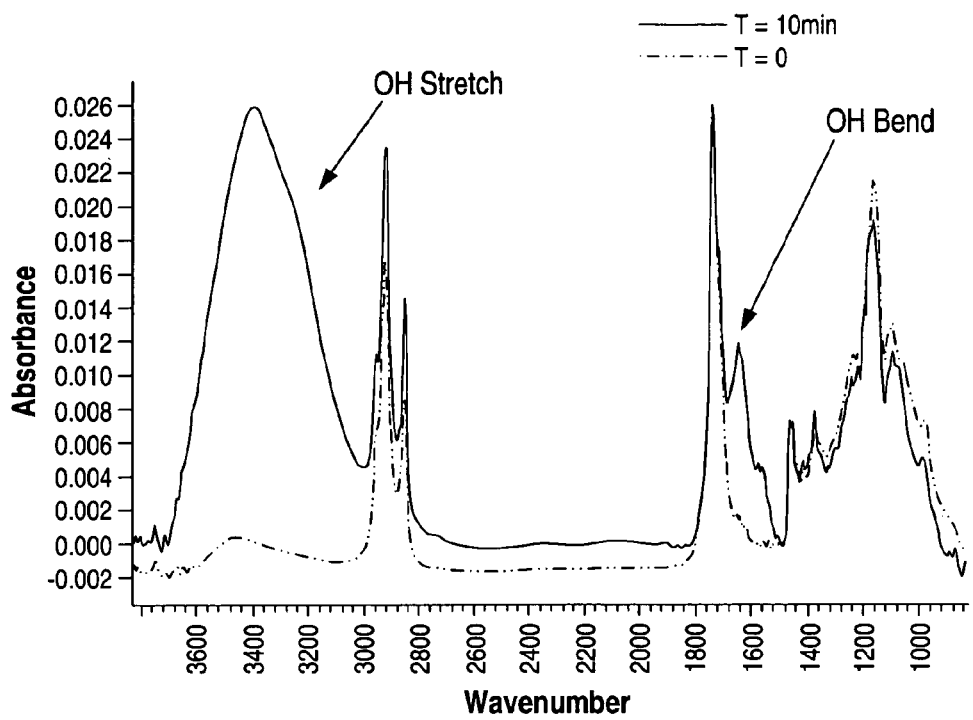
FIGS. 20A and 20B depict the FTIR spectra of a fish-oil derived biomaterial as a function of hydration time for a fatty acid-derived biomaterial described in Example 3.
Figure 20B:
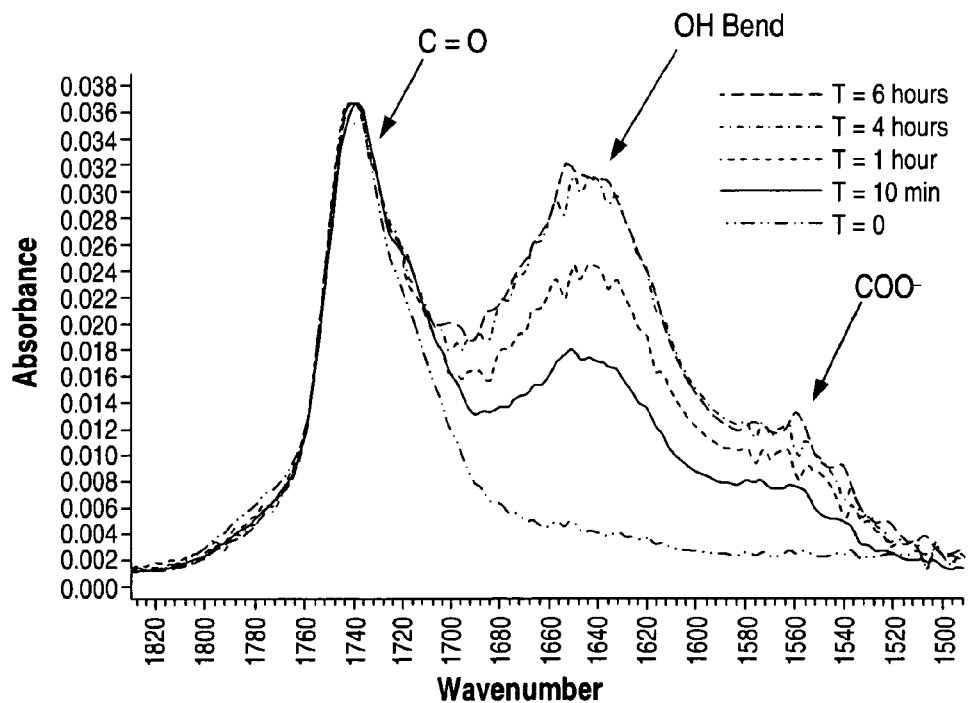

FTIR analysis of the coating after 10 min of hydration in 0.1 M PBS is presented in FIG. 20A. Excess water was removed prior to coating analysis and a Specac Silvergate ATR accessory with a Ge sensing crystal was used for analysis of the coatings. The FTIR spectra in FIG. 20A show that after being soaked in PBS solution for 10 min that the fatty acid-derived biomaterial rapidly absorbs water as indicated by the presence of strong OH absorption bands after only 10 min of hydration. Additionally, FTIR measurements taken as a function of time out to 6 hours and normalized to the carbonyl band height from the coating (FIG. 20B) show that the OH bending absorption band continues to grow and levels off at 4 hours as the coating hydrates, which is consistent with the contact angle measurements. Finally, there is a shoulder on the OH bending mode at 1580 cm$^{-1}$, which is consistent with the ionization of fatty acid COOH into COO$^-$ in a hydrated environment (K. M. Faucher and R. A. Dluhy, *Colloids and Surfaces A*, 2003, Vol. 219, pgs 125-145).

Example 4

Analysis of In-Vitro Hydrolysis Chemistry of a Novel Biomaterial Derived from Fish Oil Using Basic Digestion In the following example, coated medical devices were cured in a high airflow oven at 200° F. for 24 hours, after which the fish oil was converted into a cross-linked biomaterial gel coating encapsulating the polypropylene mesh by oxidation of the C=C bonds present in the fish oil resulting in the formation of oxidative byproducts (i.e., hydrocarbons, aldehydes, ketones, glycerides, fatty acids) while largely preserving the esters derived from the original oil triglycerides. Volatilization of the byproducts followed by the formation of ester and lactone cross-links result in the solidification of oil into a bioabsorbable hydrophobic cross-linked biomaterial. The ability for the coating to be hydrolyzed was investigated using basic digestion and the components were identified after neutralization using FTIR.

Figure 21A:
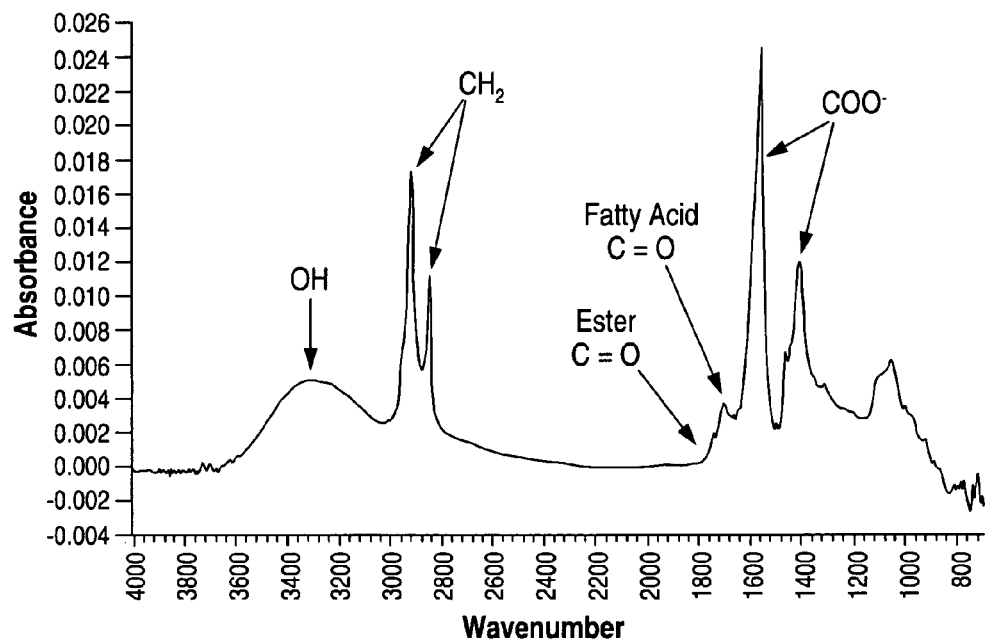
FIGS. 21A and 21B depict the FTIR spectra of a base-digested fish-oil derived biomaterial after neutralization as discussed in Example 4.
Figure 21B:
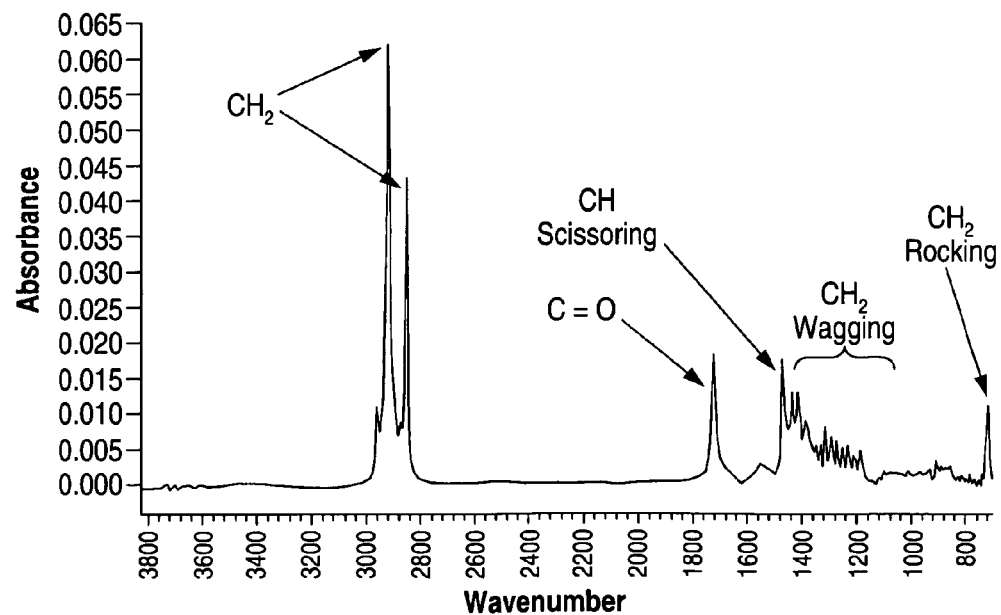

The fish fatty acid-derived biomaterial coating was immersed in 0.1 M NaOH solution and completely hydrolyzed in less than 20 min at room temperature with a clear, amber solution being produced. The basic solution was then adjusted to neutral pH using HCl, after which a precipitate formed. Both the neutralized solution and the precipitate were analyzed using FTIR with a Specac Silvergate ATR accessory with a Ge sensing crystal. The materials were allowed to dry on the Ge ATR crystal prior to FTIR analysis. The FTIR spectra acquired of the hydrolyzed coating fractions are presented in FIG. 21. The FTIR spectrum of the neutralized solution after drying (FIG. 15A) shows OH, CH$_2$, ester C=O, fatty acid C=O and COO$^-$ (antisymmetric and symmetric) absorption bands. The OH and ester C=O are consistent with the presence of glycerol and glyceride components. The carboxylate ion (COO$^-$) peaks from the hydrolysis solution are specific to the fatty acids in the coating as neither ketone nor aldehyde molecules exhibit absorption bands in this area (K. M. Faucher, 2003; Van de Voort et al., 1994). The strength of the OH and COO$^-$ bands in FIG. 21A indicates that the hydrolysis solution predominantly contains fatty acids, glycerides, and glycerol components. FIG. 21B of the material that precipitated out upon neutralization of the basic digestion of the fatty acid-derived biomaterial coating presented a spectrum that is characteristic of fatty acid crystallization spectra with the presence of strong CH$_2$, C=O, and CH$_2$ scissoring, rocking, and wagging modes (K. M. Faucher, 2003). These results are consistent with the GC-MS organic extraction of the coating presented in FIG. 14 (Example 1) that showed that the majority of the coating components detected were fatty acids and glycerides.

Example 5

Analysis of In-Vitro Hydrolysis Chemistry of a Novel Biomaterial Derived from Fish Oil in 0.1 M PBS Solution In the following example, coated medical devices (e.g., a polypropylene mesh) were cured in a high airflow oven at 200° F. for 24 hours, after which the fish oil was converted into a cross-linked biomaterial gel coating encapsulating the polypropylene mesh by oxidation of the C=C bonds present in the fish oil resulting in the formation of oxidative byproducts (i.e., hydrocarbons, aldehydes, ketones, glycerides, fatty acids) while largely preserving the esters derived from the original oil triglycerides. Volatilization of the byproducts followed by the formation of ester and lactone cross-links result in the solidification of oil into a bioabsorbable hydrophobic cross-linked biomaterial. The ability for the coating to be slowly hydrolyzed was investigated using 0.1 M PBS solution. The PBS solution was analyzed using GC-FID fatty acid profile and GPC chromatographic measurements after hydrolysis of the fatty acid-derived biomaterial in PBS for 30 days.

Figure 22:
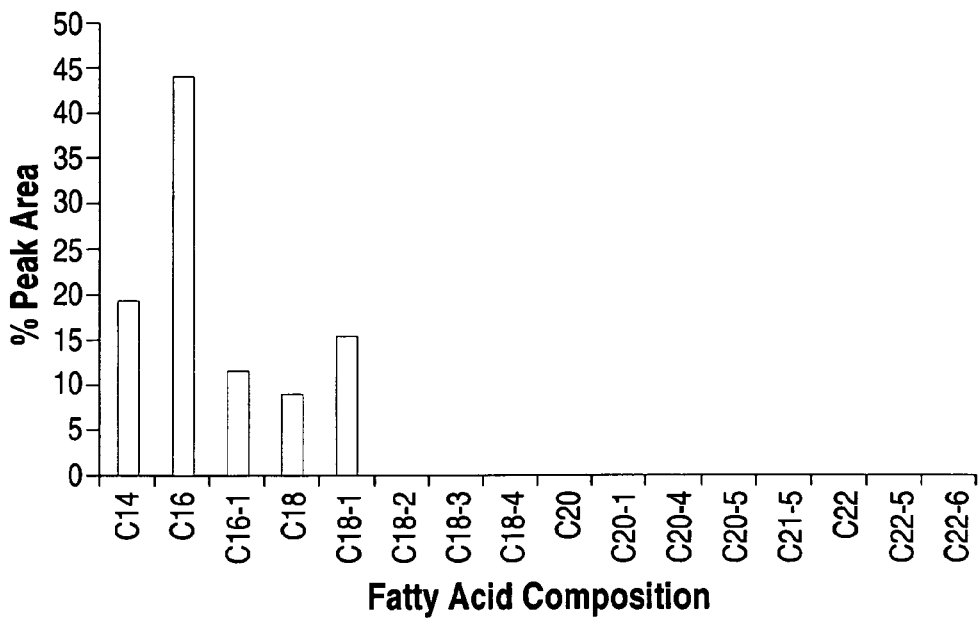
FIG. 22 provides the GC-FID fatty acid profile from a 0.1 M PBS solution after 30 day exposure of a fatty acid-derived biomaterial as described in Example 5.

FIG. 22 summarizes the fatty acid profile results obtained after drying the PBS solution and then performing a GC-FID fatty acid profile analysis as described in the AOCS official method Ce 1-89b to identify the fatty acids present in solution. FIG. 22 shows that the fatty acids identified from the PBS solution are the same as those detected from the coating itself (FIG. 22 versus FIG. 13). GPC analysis was also conducted on the hydrolysis solution and the results are summarized in Table 5. The GPC results showed that the vast majority of molecular weight components identified (80%) were below a molecular weight of 500, which is consistent with the fatty acid components of the coating. Also, glyceride components of the coating could be identified with molecular weights around 1000 (15% of the coating). The GPC results also showed a negligible amount (approximately 4%) of high molecular weight gel. The GPC results support the other analytical characterization experiments on the fatty acid-derived coatings which show that the fatty acid-derived biomaterial is comprised of cross-linked glycerides and fatty acids, and that the coating is non-polymeric.

TABLE 5

GPC Analysis of PBS Hydrolysis Solution after Contact with Fish Fatty acid-Derived Biomaterial for 30 days.

| Molecular Weight | % Peak Area | Potential Identity |
| --- | --- | --- |
| >110,000 | 4 | High Molecular Weight Gel |
| >1000 | 1 | Partially Hydrolyzed Gel |
| 1000 | 15 | Glycerides |
| <500 | 80 | Fatty Acids |

Example 6

FTIR Analysis of Fish Fatty Acid-Derived Biomaterials at Various Time Points After Being Implanted In-Vivo In the following example, coated medical devices (e.g., a polypropylene mesh) were cured in a high airflow oven at 200° F. for 24 hours, after which the fish oil was converted into a cross-linked biomaterial gel coating encapsulating the polypropylene mesh by oxidation of the C=C bonds present in the fish oil resulting in the formation of oxidative byproducts (i.e., hydrocarbons, aldehydes, ketones, glycerides, fatty acids) while largely preserving the esters derived from the original oil triglycerides. Volatilization of the byproducts followed by the formation of ester and lactone cross-links result in the solidification of oil into a bioabsorbable hydrophobic cross-linked biomaterial. This example was performed to assess the coating described herein after implantation in a rat abdominal wall defect for various lengths of time. Mesh samples were implanted in a rat abdominal wall defect for 4, 7, 14, 21, and 28 days. At each time point, the entire piece of mesh and some surrounding tissue was explanted, wrapped in saline soaked gauze and placed in specimen containers. Sections of the explanted mesh (approx. 1 cm×1 cm) were dissected, soaked in NERL water overnight in a refrigerator and air dried in a hood overnight. The dried mesh explants were analyzed using a Specac Silvergate HATR Ge accessory to analyze bulk sections of the coating.

Physically, the explants were observed to have increased tissue in-growth on the rough side (peritoneal side) over time. This in-growth was very difficult to remove at the later time points (21 and 28 days). A very thin layer of tissue was noted over the smooth side of the explants at the later time points (21 and 28 days). This layer of tissue was not attached to the coating, but was lying on top of it and was easily removed. In addition, the coating appeared to be absorbed over the course of the example as indicated by a visible thinning of the coating where bare polypropylene fibers were exposed where they are normally buried on the continuous smooth side of the coating prior to implantation.

Figure 23:
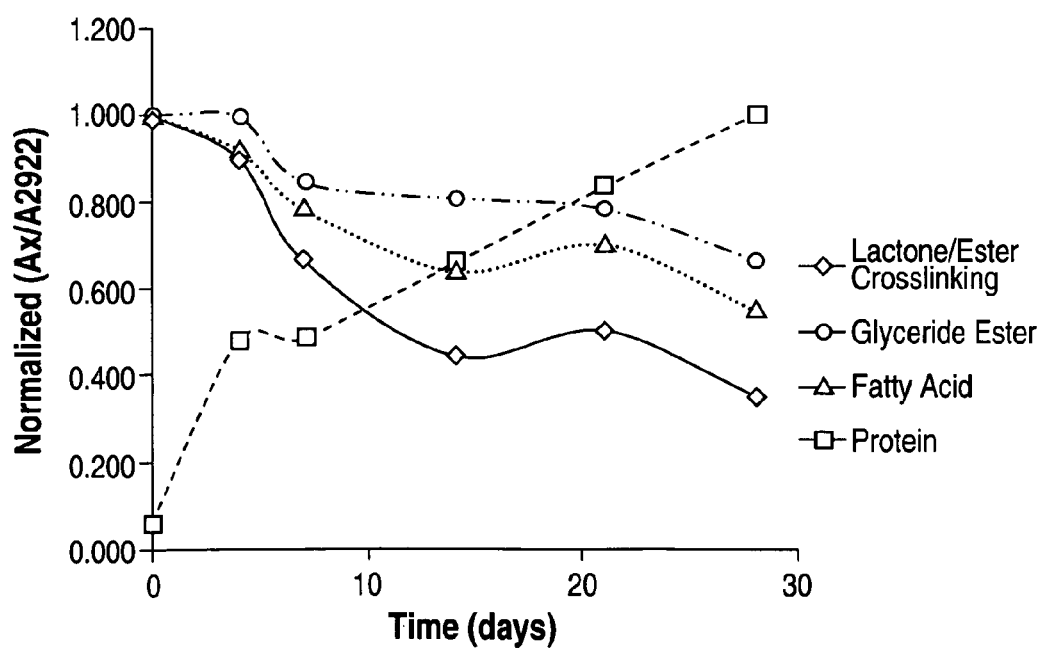
FIG. 23 depicts FTIR data discussed in Example 6.

FIG. 23 shows the plot of the normalized changes in lactone/ester cross-linking (♦), glyceride ester (■), fatty acid (▲), and protein (X) band peak height normalized to the $CH_2$ antisymmetric stretch as a function of time. This data numerically summarizes the changes in peak height observed in the FTIR data. These results show that the mesh coating is being hydrolyzed and absorbed in vivo. Chemically, it appears that it is occurring by the absorption of the short chain fatty acid, ketone, and aldehyde byproducts in addition to the breaking down the aliphatic peroxide, anhydride, and lactone cross-linking bands. From literature studies on the metabolism of triglycerides and fatty acids in the GI tract in vivo, we would expect the shorter chain length byproducts to be absorbed more quickly than the cross-linked glyceride components. The FTIR data appears to be consistent with this result. Without being bound by any particular theory, based on the hydrolysis of the cross-linking bands and prior literature, the FTIR data supports a hydrolysis and/or enzymatic (i.e., lipase) bioabsorption of the coating.

Example 7

GC-FID Fatty Acid Profile Analysis of Fish Fatty Acid-Derived Biomaterials at Various Time Points After Being Implanted In-Vivo In this example, coated medical devices were cured in a high airflow oven at 200° F. for 24 hours, after which the fish oil was converted into a cross-linked biomaterial gel coating encapsulating the polypropylene mesh by oxidation of the C═C bonds present in the fish oil resulting in the formation of oxidative byproducts (i.e., hydrocarbons, aldehydes, ketones, glycerides, fatty acids) while largely preserving the esters derived from the original oil triglycerides. Volatilization of the byproducts followed by the formation of ester and lactone cross-links result in the solidification of oil into a bioabsorbable hydrophobic cross-linked biomaterial. This example was performed to assess the coating described herein after implantation in a rat abdominal wall defect for various lengths of time. Mesh samples were implanted in a rat abdominal wall defect for 4, 7, 14, and 21 days. At each time point, the entire piece of mesh and some surrounding tissue was explanted, placed in specimen containers and frozen at −80° C. until analysis. Sections of the explanted mesh (approx. 2.5 cm×2.5 cm) were dissected from tissue and subjected to GC-FID fatty acid profile analysis using AOCS method Ce 1-89b.

Similar to the FTIR analysis described in Example 4, the explants were observed to have increased tissue in-growth on the rough side (peritoneal side) over time. This in-growth was very difficult to remove at the later time points (21 days). A very thin layer of tissue was noted over the smooth side of the explants at the later time points and there was tissue in-growth through the polypropylene mesh (at 21 days). In addition, the coating appeared to be absorbed over the course of the example as indicated by a visible thinning of the coating.

Figure 24:
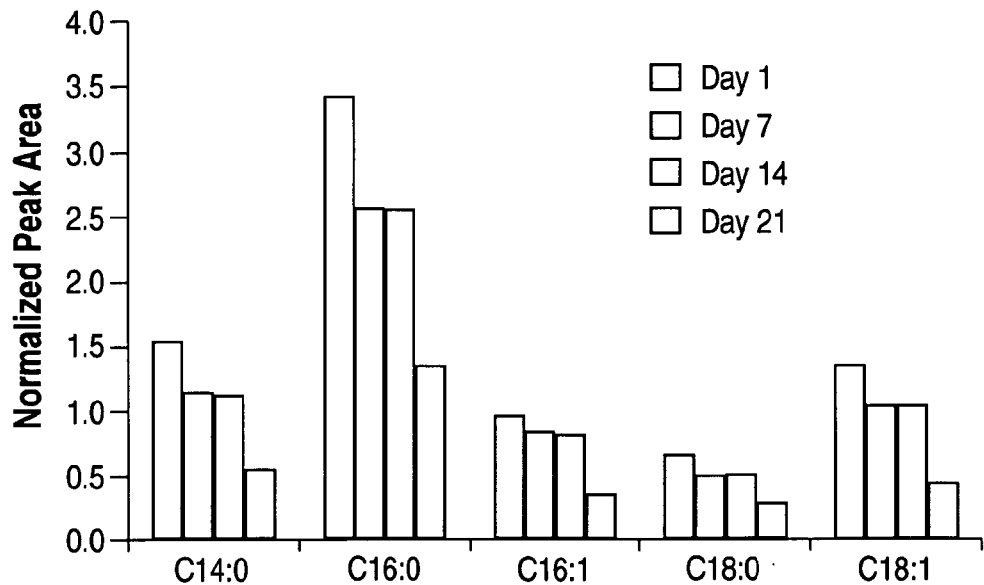
FIG. 24 provides GC-FID fatty acid profile data from a fatty acid-derived biomaterial after explanation at various time points as described in Example 7.

FIG. 24 presents the GC-FID fatty acid profile analysis of the explanted fish-oil derived coatings at various time points and normalized with an internal standard. This data shows that the fatty acids are being absorbed away as the tissue is growing into the coating. The significant drop in fatty acid composition at day 21 correlates with visible tissue in-growth and these findings are consistent with a bioabsorption mechanism of the coating.

Example 8

Biocompatibility Testing of Fatty Acid-Derived Hydrophobic Biomaterials

In this example, coated medical devices were cured in a high airflow oven at 200° F. for 24 hours, after which the fish oil was converted into a cross-linked biomaterial gel coating encapsulating the polypropylene mesh by oxidation of the C═C bonds present in the fish oil resulting in the formation of oxidative byproducts (i.e. hydrocarbons, aldehydes, ketones, glycerides, fatty acids) while largely preserving the esters derived from the original oil triglycerides. Volatilization of the byproducts followed by the formation of ester and lactone cross-links result in the solidification of oil into a bioabsorbable hydrophobic cross-linked biomaterial. This example was performed to assess the biocompatibility and in-vivo performance of the fish fatty acid-derived coating.

The fish-oil derived coating described herein was subjected to ISO 10993 (Biological Evaluation of Medical Device) Testing. The results are summarized in Table 6. Based on the results in Table 6, the novel fish fatty acid-derived biomaterial was demonstrated to be biocompatible. The fish fatty acid-derived biomaterial coating was implanted in a rat abdominal defect model to determine the ability for the coating to reduce adhesion formation in comparison to a polypropylene control. The samples were explanted at 4, 7, 14, 21, and 28 days and given an adhesion score, 0—no adhesions; 1—adhesions freed by gentle blunt dissection; 2—adhesions freed by aggressive blunt dissection; 3—Adhesions requiring sharp dissection (cutting). The results (Table 7) showed that the fish-oil derived biomaterial reduced the incidence and tenacity of the adhesions in addition when compared to the polypropylene mesh control.

TABLE 6

Summary of ISO 10993 Biological Evaluation of Medical Device Testing Results

| Test | Result |
|---|---|
| Sensitization Test | Passed |
| Genotoxicity | Non-Mutagenic |
| Irritation | Passed |
| Cytotoxicity | Non-cytotoxic |
| Pyrogenicity | Non-pyrogenic |
| Acute System Toxicity | Non-Toxic |
| Wound Healing Rate | Normal |
| Chronic Toxicity (13 and 26 weeks) | Passed |

TABLE 7

Summary of Rat Abdominal Defect Study

| Days Implanted | Fish Oil Derived Biomaterial (Mean Adhesion Score) | Bare Polypropylene Control (Mean Adhesion Score) |
|---|---|---|
| 4 day | 0.4 | 1 |
| 7 day | 1.4 | 2.7 |
| 14 day | 1.6 | 2.3 |
| 21 day | 1.5 | 2.8 |
| 28 day | 1.2 | 2.7 |

Example 9

In Vivo Performance of Fish Fatty Acid Derived Biomaterial

The coating prepared as described in Example 7 was implanted in a rat abdominal wall defect model for 30 days to assess the inflammatory response of the coating, as well as its ability to reduce adhesion formation as compared to a bare polypropylene mesh. Histopathology was conducted on the explanted samples using standard H&E staining to determine the amount of inflammation present on the coated samples and the bare polypropylene samples. The results are shown in Table 8, below. Histopathology on the coated samples revealed minimal inflammation associated with the coating itself, as most inflammatory cells present were associated with the polypropylene monofilaments. Histology also confirmed what was seen in the gross adhesion assessment; minimal to no tissue attachment on the visceral surface of the implants. At the 30-day time point, both the bare polypropylene and the coated samples demonstrated good tissue incorporation on the abdominal wall surface of the implants.

TABLE 8

Inflammation Scores, 30-Day Rat Implant Study

| Test Group | Inflammation Score (mean score) | Adhesion Score (mean score) |
|---|---|---|
| Bare Polypropylene | 3.1 | 2.5 |
| Fish Oil Derived Biomaterial | 2.0 | 1.2 |

[Inflammation Scale: 1—no inflammatory cells present; 2—mild, few inflammatory cells present; 3—moderate; 4—severe, intense inflammatory response] [Adhesion Scale: 0—No Adhesions; 1—Adhesions freed by gentle blunt dissection; 2—Adhesions freed by aggressive blunt dissection; 3—Adhesions requiring sharp dissection (cutting)]

Example 10

Ability to Form Fatty acid-Derived Biomaterials with Different Physical Properties and Chemistries by Altering Formation Process In this example, different fish fatty acid-based biomaterial devices were produced. First, a partially cured fish oil gel was produced by taking 1 L of fish oil and curing it in a jacketed glass reactor while bubbling oxygen through it at 200° F. for 20 hours with a final viscosity range of 120 k-130 k cps. The stand-alone film was created using the partially cured fish oil, casting it onto a PTFE lined stainless steel pan, and initially setting the coating by UV lamp exposure using germicidal lamps for 25 min (i.e., photo-oxidation) and then subjecting the film to a final heat curing process at 24 hours at 200° F. Fish oil coated mesh samples were created by coating a piece of bare mesh in pure fish oil and curing using either 150° F. (72 hours) or 200° F. (24 hours) curing conditions. In this example, the effect of curing process on the composition of fish-oil derived biomaterial coatings was studied.

Figure 25:
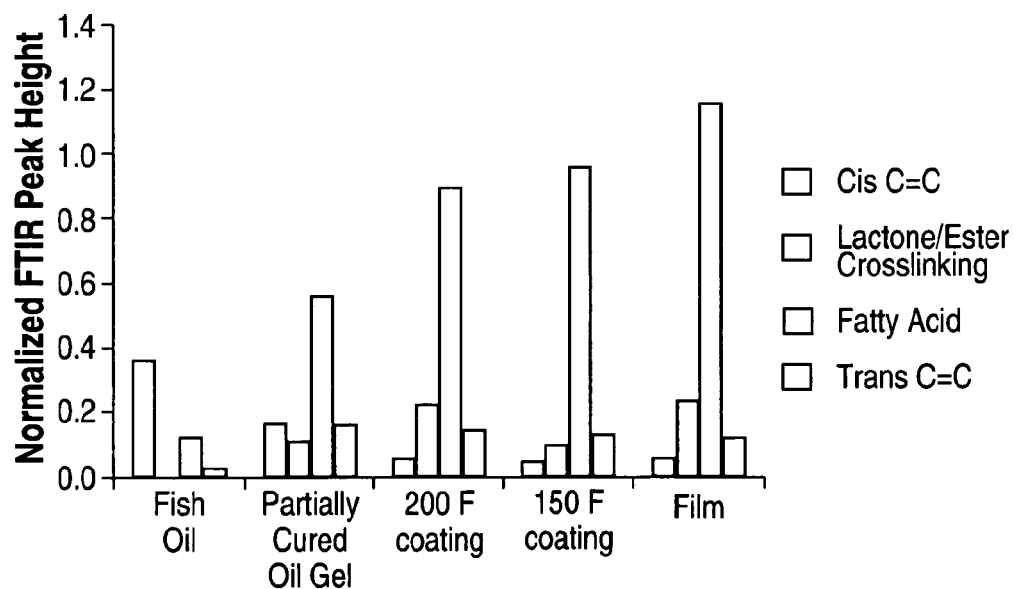
FIGS. 25 and 26 provide the characterization FTIR and GC-FID fatty acid profile data for fatty acid-derived biomaterials produced using different methods of manufacture as described in Example 10.
Figure 26:
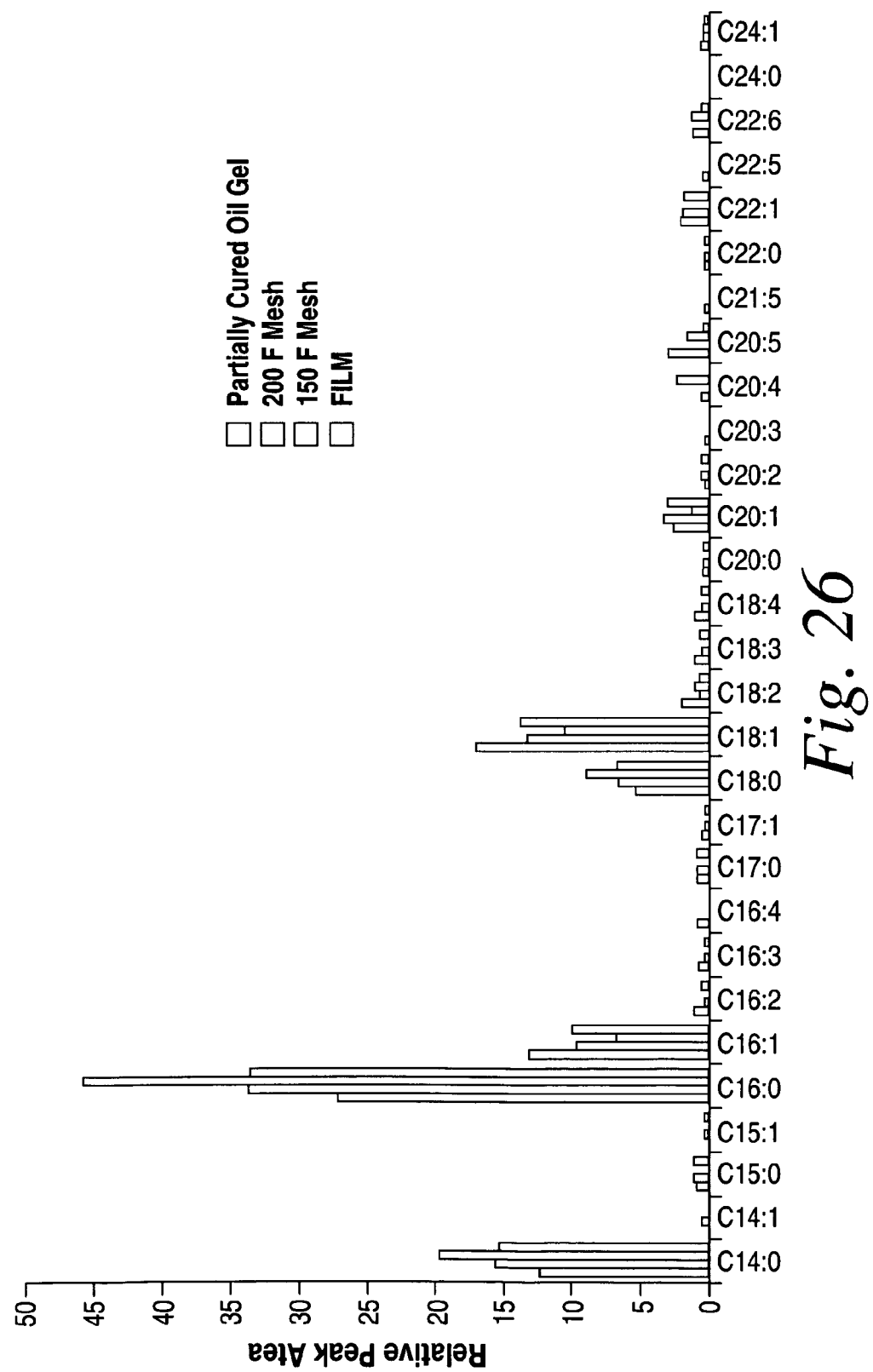

FTIR analysis of the different cured materials (i.e., 150° F. coating, 200° F. coating, film, and partially cured fish oil) is summarized in FIG. 25. The data in FIG. 25 shows that altering curing conditions produces materials with differing amounts of fatty acid byproducts, lactone/ester cross-linking, and cis-trans C=C isomer ratios. These differences are also reflected in the GC-FID fatty acid profiles obtained using the official AOCS Ce 1-89b, (FIG. 26), which shows that by altering the curing process the final fatty acid composition can be altered. The alteration of fatty acid composition can affect both drug delivery release profile and potentially the inflammatory properties of the fatty acid-derived biomaterial.

Example 11

Tailoring Drug Release Profile of Coating

The following examples demonstrate the ability to alter the chemistry and position of the drug-containing layer in cured fish oil mesh coatings. The chemistry of the various coating layers can be adjusted by employing different curing conditions and/or vitamin E composition.

The Effects of Curing Time and Temperature

All coated mesh samples were 1×1" and dissolution was performed in 0.01 M PBS solution. Drug release coated mesh samples were created by mixing the fish oil and drug followed by coating a piece of bare mesh and curing using either 150° F. (72 hours) or 200° F. (24 hours) curing conditions.

Figure 27:
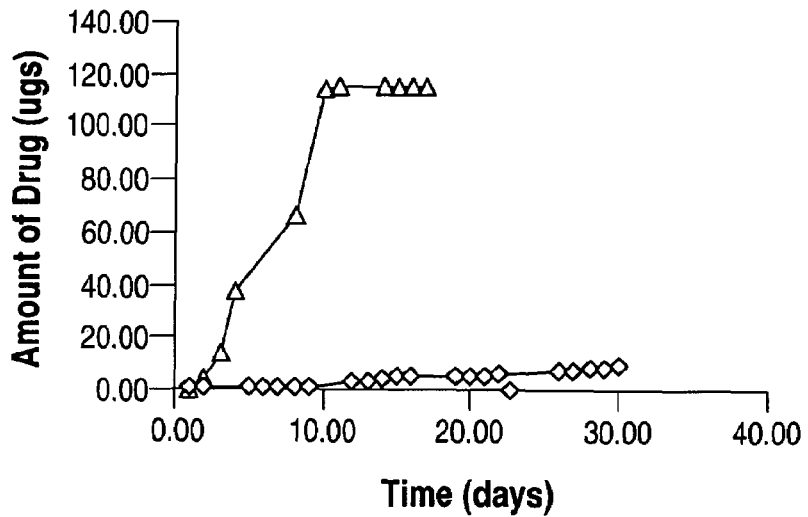
FIGS. 27 and 28 depict drug release data in an aqueous media discussed in Example 11.

FIG. 27 depicts the drug release profile measured for an anti-inflammatory drug. The figure compares two curing conditions, heating for 24 hours at 200° F. or heating for 3 days at 150° F. The starting material comprised 3.29% model anti-inflammatory drug (after nMP solvent was removed) in fish oil (EPAX 3000 TG).

These results show that adjusting curing temperature can alter the release of an anti-inflammatory therapeutic agent. The sample cured at 150° F. (▲), due to the lower amount of cross-linking and final fatty acid composition, releases more rapidly than the more cross-linked 200° F. sample (♦). This illustrates the flexibility of the coating system where the release rate of the therapeutic can be altered based on the chemistry of the fatty acid-derived biomaterial coating chemistry, which can be tailored based on the cure time, type of oil utilized, cure methods, thickness of coating, and/or temperature conditions employed.

Figure 28:
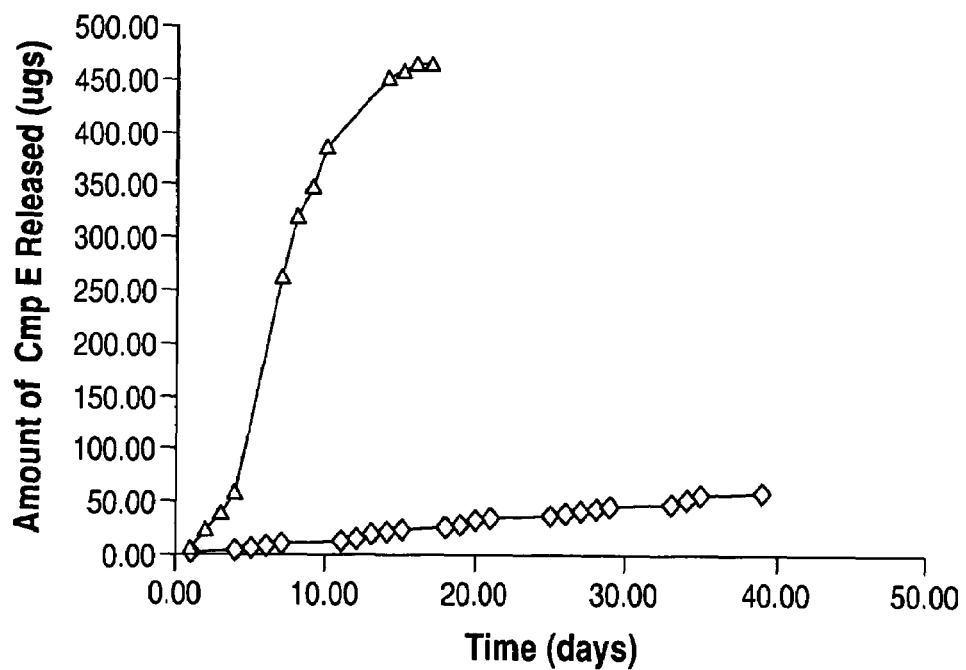

FIG. 28 depicts a further drug release profile measured for an anti-proliferative. The figure compares two curing conditions, heating for 24 hours at 200° F. or heating for 3 days at 150° F. The starting material comprised 2.84% Compound E in fish oil (EPAX 3000 TG). No solvent was used as Compound E was soluble in the fish oil with slight heating at 37° C. The initial drug loading after curing, based on HPLC measurements, was about 478 μg (14.22% recovery, ♦) in the 200° F. cured coating and about 1158 μg (26.00% recovery, ▲) in the 150° F. cured coating. It is to be noted that the percentage amount recovered is dependent on the coating weight and amount of drug detected using HPLC methods after drug extraction from the cured fish oil coating.

These results show that adjusting curing temperature and drug layer coating position can also alter the release of Compound E, an anti-proliferative. The 150° F. samples, due to the lower amount of cross-linking, release more rapidly than the more cross-linked samples cured at 200° F. Finally, the drug extraction results show that the Compound E, which is a peptide, is more stable using the 150° F. curing conditions (i.e. higher HPLC assay recovery).

In Combination with Vitamin E

All coated mesh samples were 1×1" and dissolution was performed in 0.01 M PBS solution. All drug samples were loaded as a cured first layer on the mesh and were created by mixing the liquid fish oil and drug together, with or without solvent, followed by coating a piece of bare mesh and curing at 150° F. for 3 days.

Figure 29:
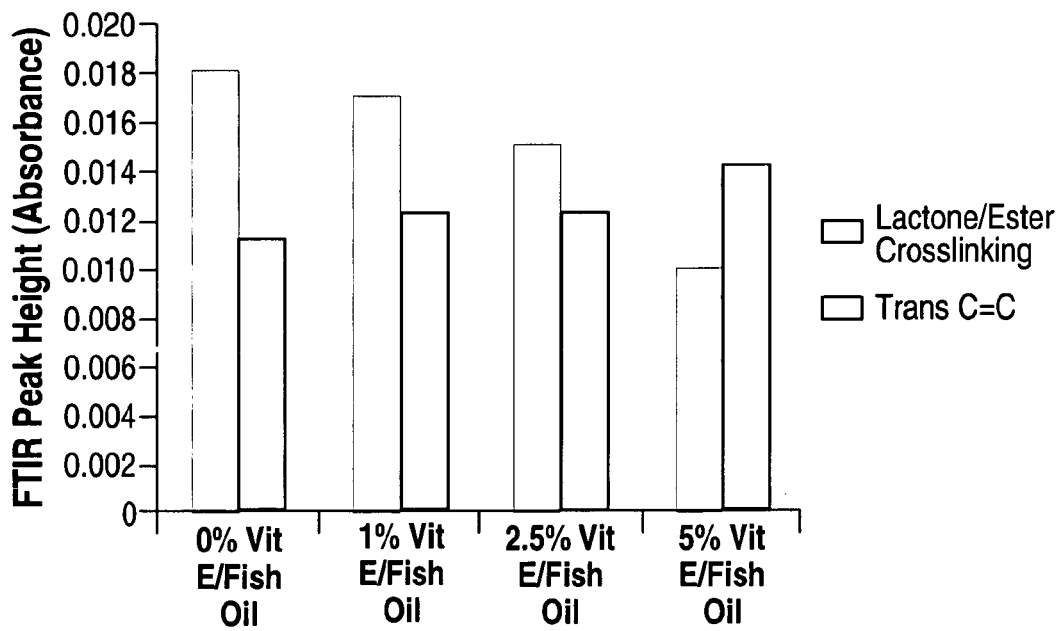
FIG. 29 depicts FTIR data for various vitamin E containing fatty acid-derived biomaterials as discussed in Example 11.
Figure 30:
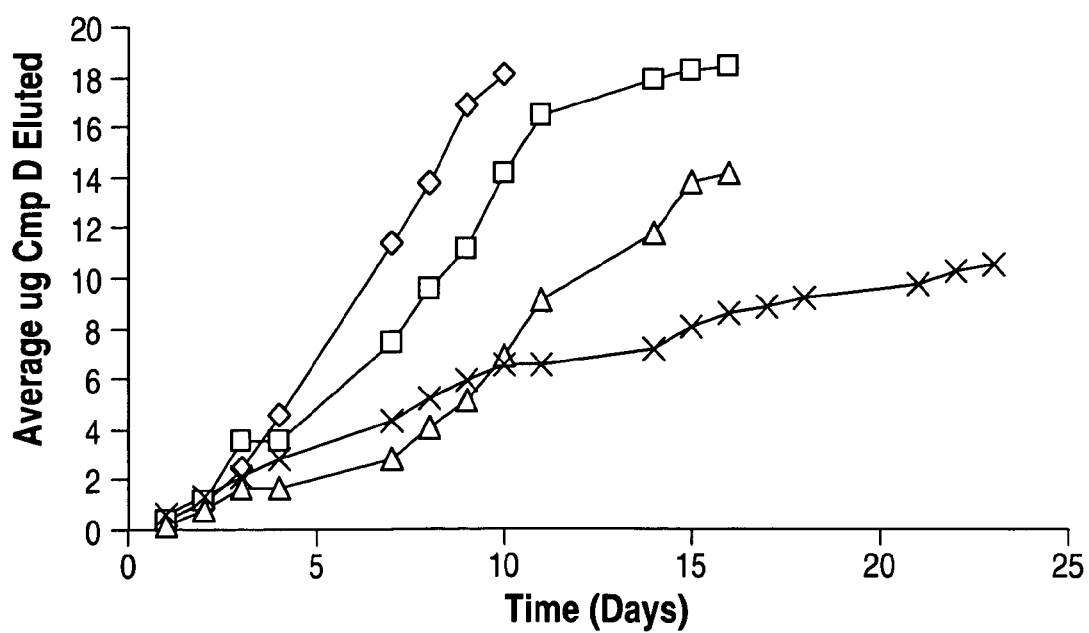
FIG. 30 depicts drug release data in an aqueous media discussed in Example 11.

FIG. 29 shows the effects of vitamin E composition on the cross-linking and trans C═C band as a function of temperature. As the amount of Vitamin E is increased the amount of lactone/ester cross-linking is reduced and the amount of oxidation (as monitored by the trans C═C band) is also reduced. FIG. 30 depicts the drug release profile measured for Compound D. The figure compares varying amounts of vitamin E added to the starting material prior to curing for 3 days at 150° F. The starting materials comprised 4.88% Compound D (after solvent removal) in varying amounts of vitamin E in fish oil coatings (0-5%). The initial drug loading for the 100% fish oil sample (no vitamin E) was after curing, based on HPLC measurements, was about 270 µg (5.5% recovery, ●) in the overlayer, and about 378 µg (16.5% recovery, ♦) in the first coating (underlayer). The initial drug loading for the 5% vitamin E in fish oil sample was after curing, based on HPLC measurements, was about 3584 µg (66.7% recovery, +) in the overlayer, and about 3013 µg (52.2% recovery, ■) in the first coating (underlayer).

These results show that altering the vitamin E composition can alter the release of a therapeutic from the cured fish oil coating. Increasing the amount of vitamin E results in lengthening and slowing the release of Compound D into the dissolution buffer, due to its enhanced solubility and affinity for the vitamin E component in the cured fish oil coating. Additionally, the cured 5% vitamin E/fish oil overlayer coating results in an increase in the amount of drug released when compared to the encapsulated mesh.

Example 12

Cured Oil Coatings Loaded with Therapeutics and Applied to Metallic Stents

Figure 31:
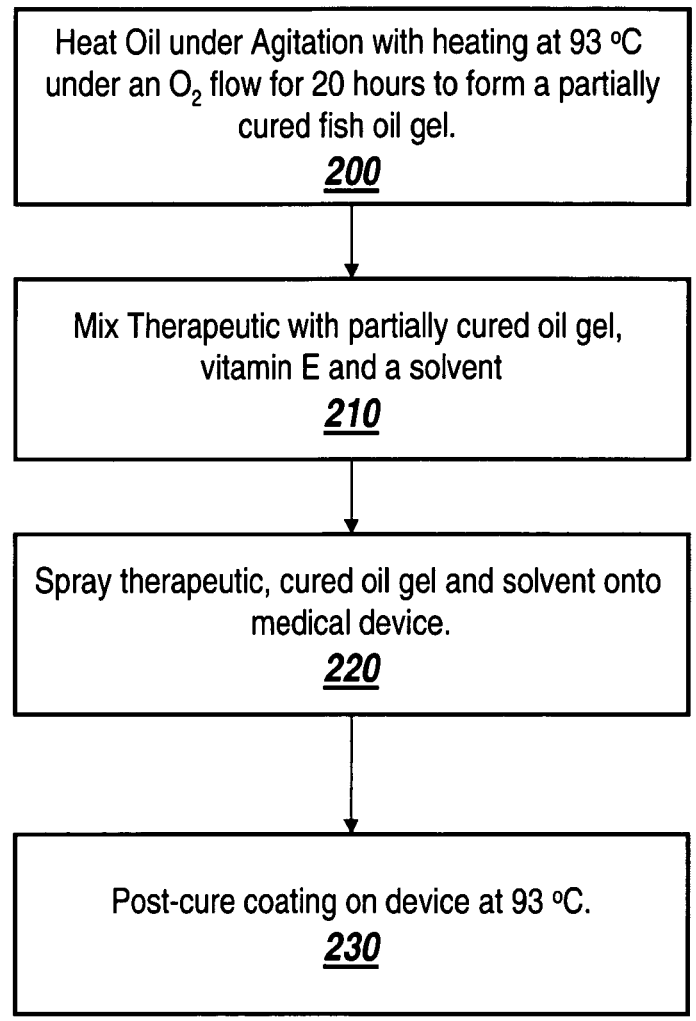
FIG. 31 depicts a flow diagram presenting the process to create a cured coating on a stent loaded with a therapeutic is outlined in Example 12.
Figure 32:
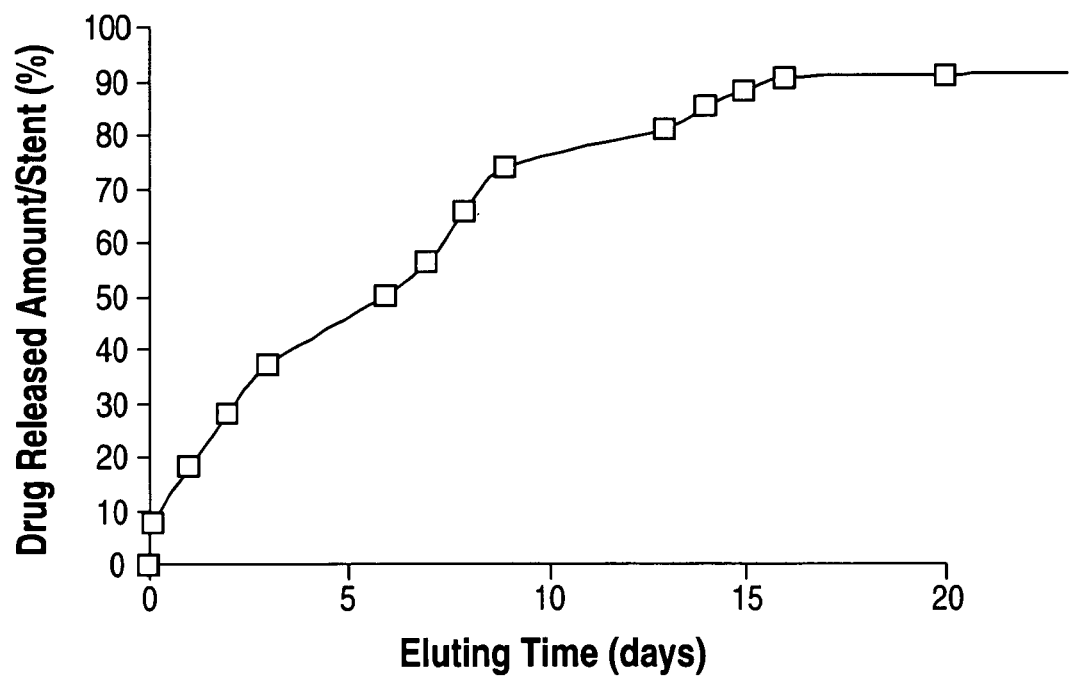
FIG. 32 shows the drug release profile for a cured oil therapeutic coating in 0.01 M PBS buffer as described in Example 12.

In this particular embodiment, the application of cured oil coatings loaded with a therapeutic and applied to a cardiac stent are presented. The flow diagram presenting the process to create a cured coating on a stent loaded with a therapeutic is outlined in FIG. 31. Briefly, a partially cured fish oil coating is created in a reaction vessel under agitation with heating at 200° F. for 20 hours. The fatty acid-derived coating is mixed with the therapeutic of interest, and vitamin E with a solvent and then sprayed onto the stent to create a coating. The coating is annealed to the stent surface by heating at 200° F. for 7 hours to create a uniform coating. A coating with a model anti-inflammatory agent showed that this process allowed for 90% of the drug to be recovered after curing as determined using extraction of the drug from the device with HPLC analysis. FIG. 32 shows the drug release profile for this coating in 0.01 M PBS buffer going out to 20 days with over a 90% recovery of the drug recovered using this process.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the appended claims is reserved. It is intended that the present invention be limited only to the extent required by the appended claims and the applicable rules of law.

All literature and similar material cited in this application, including, patents, patent applications, articles, books, treatises, dissertations and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way.

While the present invention has been described in conjunction with various embodiments and examples, it is not intended that the present teachings be limited to such embodiments or examples. On the contrary, the present invention encompasses various alternatives, modifications, and equivalents, as will be appreciated by those of skill in the art.

The claims should not be read as limited to the described order or elements unless stated to that effect. It should be understood that various changes in form and detail may be made without departing from the scope of the appended claims. Therefore, all embodiments that come within the scope and spirit of the following claims and equivalents thereto are claimed.

The invention claimed is:

1. A coating for a medical device, comprising fatty acids cross-linked directly to each other by ester or lactone bonds; wherein the fatty acids comprise approximately 5-50% $C_{16}$ fatty acids; and wherein the coating hydrolyzes in vivo.

2. The coating of claim 1, wherein the fatty acids comprise 5-25% $C_{14}$ fatty acids.

3. The coating of claim 1, wherein the fatty acids comprise 5-30% $C_{16}$ fatty acids.

4. A coating for a medical device comprising fatty acids cross-linked directly to each other by ester or lactone bonds; wherein the coating hydrolyzes in vivo into free fatty acids, glycerides and glycerol; and wherein the coating is formed from one or more of eicosapentaenoic acid (EPA), docosahexanoic acid (DHA), or alpha-linolenic acid (ALA).

5. A coating for a medical device, comprising fatty acids cross-linked directly to each other by ester or lactone bonds; wherein the fatty acids comprise approximately 5-25% $C_{14}$ fatty acids and 5-50% $C_{16}$ fatty acids; and wherein the coating hydrolyzes in vivo substantially into one or more of free fatty acids, glycerides, or glycerol.

6. A coating for a medical device comprising fatty acids and glycerides; wherein the fatty acids are cross-linked directly to each other by one or more of ester bonds, or lactone bonds; wherein the fatty acids and glycerides have disordered alkyl groups, which cause the coating to be flexible and hydratable; and wherein the coating hydrolyzes in vivo.

7. A coating for a medical device comprising a fatty acid-derived biomaterial; wherein the fatty acid-derived biomaterial comprises fatty acids and glycerides; wherein the fatty acids are cross-linked directly to each other by one or more of ester bonds, or lactone bonds; and wherein the coating hydrolyzes in vivo.

8. The coating of claim 7, wherein the coating has a peak from approximately 1740-1830 $cm^{-1}$, as indicated by an infrared absorption spectrum.

9. The coating of claim 7, wherein the biomaterial comprises approximately 60-90% fatty acids with molecular weights below 500.

10. The coating of claim 7, wherein the fatty acid is stearic acid, oleic acid, linoleic acid, alpha-linolenic acid, or gamma-linolenic acid.

11. The coating of claim 7, wherein the source of the fatty acid is an oil.

12. The coating of claim 11, wherein the oil is a fish oil, olive oil, grape oil, palm oil, or flaxseed oil.

13. A coating for a medical device, comprising a fatty acid-derived biomaterial; wherein the fatty acid-derived biomaterial comprises fatty acids and glycerides; wherein the fatty acids are cross-linked directly to each other by one or more of ester bonds, or lactone bonds; wherein the coating hydrolyzes in vivo; and wherein the coating has a contact angle of approximately 90-110 degrees when initially exposed to 0.1 M PBS solution, and, after approximately one hour of exposure, has a contact angle of 50-70 degrees.

14. The coating of any one of claim 1 or 5, wherein the coating comprises lactone cross-links and ester cross-links.

15. The coating of any one of claim 1, 5, 8-9 or 13, wherein the coating contains disordered hydrocarbon chains as determined by infrared absorption and X-ray diffraction.

16. The coating of any one of claim 1, 8-9 or 13, wherein the coating breaks down in vivo into fatty acids, glycerols, and glycerides.

17. The coating of any one of claim 1, 5, 8-9 or 13, wherein the coating comprises approximately 30-90% saturated fatty acids.

18. The coating of any one of claim 1, 5, 8-9 or 13, wherein the coating comprises approximately 30-80% unsaturated fatty acids.

19. The coating of any one of claim 1, 5, or 8-9, wherein the coating further comprises a glyceride.

20. The coating of any one of claim 1, 5, or 8-9, wherein the coating further comprises one or more of the groups consisting of a glyceride, a glycerol, and a fatty alcohol, any of which can be partially cross-linked.

21. The coating of any one of claim 1, 5, 8-9 or 13, wherein the coating does not contain an external cross-linking agent.

22. The coating of any one of claim 1, 5, 9 or 13, wherein the source of the fatty acids and glycerides is an oil.

23. The coating of claim 22, wherein the oil is a fish oil, olive oil, grape oil, palm oil, or flaxseed oil.

24. The coating of claim 22, wherein the oil is a fish oil.

25. The coating of any one of claim 1, 5, 8-9 or 13, further comprising vitamin E.

26. The coating of any one of claim 1, 5, 8-9 or 13, wherein the coating is associated with a medical device, and the medical device is a stent, a catheter, a surgical mesh or a balloon.

27. The coating of any one of claim 1, 5, 8-9 or 13, further comprising a therapeutic agent.

28. The coating of claim 27, wherein the therapeutic agent is an anti-proliferative drug, an anti-inflammatory agent, an antimicrobial agent or antibiotic agent.

29. The coating of claim 27, wherein the therapeutic agent is Compound A, Compound B, Compound C, Compound n, Compound E, a cyclosporine derivative or rapamycin derivative.

30. A method of preparing a coating for a medical device, comprising heating a fatty acid-containing oil in the presence of oxygen, such that: the double bonds of the oil are oxidized; fatty acids and glycerides are formed; and fatty acids cross-linked directly to each other by one or more of ester bonds or lactone bonds are formed; such that the coating formed hydrolyzes in vivo substantially into one or more of free fatty acids, glycerides, or glycerol.

31. The method of claim 30, wherein the oil is continually heated, without interruption.

32. A method of preparing a coating for a medical device comprising heating a fatty acid-containing oil in the presence of oxygen, such that: the double bonds of the oil are oxidized; water, hydrocarbons and aldehydes are volatilized; and fatty acids cross-linked directly to each other by one or more of ester bonds or lactone bonds are formed; such that the coating formed hydrolyzes in vivo substantially into one or more of free fatty acids, glycerides, or glycerol.

33. The method of claim 32, wherein the oil is continually heated, without interruption.

34. The method of claim 30 or 32, wherein the oil is heated at approximately 140° F. to approximately 300° F.

35. The method of claim 30 or 32, wherein the oil is fish oil.

36. The method of claim 30 or 32, further including adding a therapeutic agent.

37. A non-polymeric, medical device coating produced by the method of claim 30 or 32.

38. The coating of claim 37, further associated with a medical device.

39. The coating of claim 38, wherein the coating is combined with an organic solvent, and sprayed on a medical device.

40. A method of forming a fatty acid-derived biomaterial, comprising: continued heating of a fatty acid, followed by the cleavage of C=C double bonds, which convert the fatty acids into oxidation byproducts, and fatty acids cross-linked directly to each other by one or more of ester bonds or lactone bonds are formed; wherein the fatty acid-derived biomaterial formed hydrolyzes in vivo.

41. The method of claim 40, wherein the oxidation byproducts are one or more of aldehydes, ketones, alcohols, fatty acids, esters, lactones, ethers, or hydrocarbons.

42. The method of claim 40, wherein the byproducts remain within the coating and/or are volatilized during the heating process.

43. The method of claim 40, wherein the cross-links are ester cross-links and lactone cross-links, wherein the ester cross-links and lactone cross-links occur via esterification, alcoholysis, acidolysis, or interesterfication.

44. A method of forming a fatty acid-derived biomaterial, comprising: continued heating of a fatty acid, thereby oxidizing the double bonds of the unsaturated fatty acid chains while predominantly preserving triglyceride ester functional groups; thereby increasing the viscosity of the biomaterial; wherein the fatty acid-derived biomaterial comprises fatty acids cross-linked directly to each other by one or more of ester bonds or lactone bonds; and wherein the fatty acid-derived biomaterial formed hydrolyzes in vivo.

45. A stand-alone film, comprising: a non-polymeric, cross-linked fatty acid, comprising approximately 5-50% $C_{16}$ fatty acids.

46. A method of treating soft tissue damage in a subject in need thereof, comprising administering to the damaged tissue of the subject the stand-alone film of claim 45.

47. A coating for a medical device, comprising fatty acids cross-linked directly to each other by ester or lactone bonds; wherein the fatty acids comprise approximately 5-50% $C_{16}$ fatty acids; wherein the coating hydrolyzes in vivo; and wherein the coating is formed from an oil comprising at least 40% polyunsaturated fatty acids.

48. The coating of claim 7, wherein the fatty acid-derived biomaterial comprises delta lactones.

* * * * *